US006713066B1

(12) United States Patent
Collins et al.

(10) Patent No.: US 6,713,066 B1
(45) Date of Patent: Mar. 30, 2004

(54) PRODUCTION OF ATTENUATED RESPIRATORY SYNCYTIAL VIRUS VACCINES INVOLVING MODIFICATION OF M2 ORF2

(75) Inventors: Peter L. Collins, Rockville, MD (US); Brian R. Murphy, Bethesda, MD (US); Alison Bermingham, Silver Spring, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/611,829

(22) Filed: Jul. 7, 2000

Related U.S. Application Data

(63) Continuation-in-part of application No. 09/291,894, filed on Apr. 13, 1999, which is a continuation-in-part of application No. 08/892,403, filed on Jul. 15, 1997, now Pat. No. 5,993,824.
(60) Provisional application No. 60/143,097, filed on Jul. 9, 1999, provisional application No. 60/047,634, filed on May 23, 1997, provisional application No. 60/046,141, filed on May 9, 1997, and provisional application No. 60/021,773, filed on Jul. 15, 1996.

(51) Int. Cl.$^7$ .................. A61K 39/12; A61K 39/295
(52) U.S. Cl. .................. 424/199.1; 424/202.1; 424/205.1; 424/211.1; 435/69.1
(58) Field of Search .................. 424/199.1, 202.1, 424/205.1, 211.1; 435/69.1

(56) References Cited

FOREIGN PATENT DOCUMENTS

US          WO 99/15631 A1 *   4/1999

* cited by examiner

Primary Examiner—James Housel
Assistant Examiner—Stacy B. Chen
(74) Attorney, Agent, or Firm—Graybeal Jackson Haley LLP

(57) ABSTRACT

Recombinant respiratory syncytial virus (RSV) are provided in which expression of the second translational open reading frame encoded by the M2 gene (M2ORF2) is reduced or ablated to yield novel RSV vaccine candidates. Expression of M2 ORF2 is reduced or ablated by modifying a recombinant RSV genome or antigenome to incorporate a frame shift mutation, or one or more stop codons in M2 ORF2. Alternatively, M2 ORF2 is deleted in whole or in part to render the M2-2 protein partially or entirely non-functional or to disrupt its expression altogether. M2 ORF2 deletion and knock out mutants possess highly desirable phenotypic characteristics for vaccine development. These changes specify one or more desired phenotypic changes in the resulting virus or subviral particle. Vaccine candidates are generated that show a change in mRNA transcription, genomic or antigenomic RNA replication, viral growth characteristics, viral antigen expression, viral plaque size, and/or a change in cytopathogenicity. In addition, M2-2 knock out or deletion virus exhibits increased levels of synthesis of viral proteins in cell culture, providing an enriched source of viral antigen or protein for purification and use as a noninfectious subunit vaccine.

63 Claims, 6 Drawing Sheets

PRODUCTION OF ATTENUATED RESPIRATORY SYNCYTIAL VIRUS VACCINES INVOLVING MODIFICATION OF M2 ORF2

CROSS-REFERENCES TO RELATED APPLICATIONS

This application claims the priority benefit of U.S. Provisional Application No. 60/143,097, filed by Peter L. Collins et al. on Jul. 9, 1999. The present application also claims the benefit of and is a continuation-in-part of U.S. patent application Ser. No. 09/291,894, filed Apr. 13, 1999, which is a continuation-in-part of U.S. patent application Ser. No. 08/892,403, filed Jul. 15, 1997, issued on Nov. 30, 1999 as U.S. Pat. No. 5,993,824, which is entitled to priority from U.S. Provisional Application No. 60/047,634, filed May 23, 1997; No. 60/046,141, filed May 9, 1997; and No. 60/021,773, filed Jul. 15, 1996.

BACKGROUND OF THE INVENTION

Human respiratory syncytial virus (HRSV) is the leading viral agent of serious pediatric respiratory tract disease worldwide (Collins, et al., *Fields Virology* 2:1313–1352, 1996). RSV outranks all other microbial pathogens as a cause of pneumonia and bronchiolitis in infants under one year of age. Virtually all children are infected by two years of age, and reinfection occurs with appreciable frequency in older children and young adults (Chanock et al., in *Viral Infections of Humans*, 3rd ed., A. S. Evans, ed., Plenum Press, N.Y., 1989). RSV is responsible for more than one in five pediatric hospital admissions due to respiratory tract disease, and in the United States alone causes nearly 100,000 hospitalizations and 4,500 deaths yearly. (Heilman, *J. Infect. Dis.* 161:402–6, 1990). In addition, there is evidence that serious respiratory tract infection early in life can initiate or exacerbate asthma (Sigurs, et al., *Pediatrics* 95:500–5, 1995).

While HRSV usually is thought of in the context of the pediatric population, it also is recognized as an important agent of serious disease in the elderly (Falsey, et al.,*J. Infect. Dis.* 172:389–394, 1995). HRSV also causes life-threatening disease in certain immunocompromised individuals, such as bone marrow transplant recipients (Fouillard, et al., *Bone Marrow Transplant* 9:97–100, 1992).

For treatment of HRSV, one chemotherapeutic agent, ribavirin, is available. However, its efficacy and use are controversial. There are also licensed products for RSV intervention which are composed of pooled donor IgG (Groothuis, et al. *N. Engl. J. Med.* 329:1524–30, 1993) or a humanized RSV-specific monoclonal antibody. These are administered as passive immunoprophylaxis agents to high risk individuals. While these products are useful, their high cost and other factors, such as lack of long term effectiveness, make them inappropriate for widespread use. Other disadvantages include the possibility of transmitting blood-borne viruses and the difficulty and expense in preparation and storage. Moreover, the history of the control of infectious diseases, and especially diseases of viral origin, indicates the primary importance of vaccines.

Despite decades of investigation to develop effective vaccine agents against RSV, no safe and effective vaccine has yet been approved to prevent the severe morbidity and significant mortality associated with RSV infection. Failure to develop successful vaccines relates in part to the fact that small infants have diminished serum and secretory antibody responses to RSV antigens. Thus, these individuals suffer more severe infections from RSV, whereas cumulative immunity appears to protect older children and adults against more serious impacts of the virus.

The mechanisms of immunity in RSV infection have recently come into focus. Secretory antibodies appear to be most important in protecting the upper respiratory tract, whereas high levels of serum antibodies are thought to have a major role in resistance to RSV infection in the lower respiratory tract. RSV-specific cytotoxic T cells, another effector arm of induced immunity, are also important in resolving an RSV infection. However, while this latter effector can be augmented by prior immunization to yield increased resistance to virus challenge, the effect is short-lived. The F and G surface glycoproteins are the two major protective antigens of RSV, and are the only two RSV proteins which have been shown to induce RSV neutralizing antibodies and long term resistance to challenge (Collins et al., *Fields Virology*, Fields et al. eds., 2:1313–1352, Lippincott-Raven, Philadelphia, 1996; Connors et al., *J. Virol.* 65(3):1634–7, 1991). The third RSV surface protein, SH, did not induce RSV-neutralizing antibodies or significant resistance to RSV challenge.

An obstacle to developing live RSV vaccines is the difficulty in achieving an appropriate balance between attenuation and immunogenicity. Other obstacles include the genetic instability of some attenuated viruses, the relatively poor growth of RSV in cell culture, and the instability of the virus particle. In addition the immunity which is induced by natural infection is not fully protective against subsequent infection. A number of factors probably contribute to this, including the relative inefficiency of the immune system in restricting virus infection on the luminal surface of the respiratory tract, the short-lived nature of local mucosal immunity, rapid and extensive virus replication, reduced immune responses in the young due to immunological immaturity, immunosuppression by transplacentally derived maternal serum antibodies, and certain features of the virus such as a high degree of glycosylation of the G protein. Also, as will be described below, HRSV exists as two antigenic subgroups A and B, and immunity against one subgroup is of reduced effectiveness against the other.

Although RSV can reinfect multiple times during life, reinfections usually are reduced in severity due to protective immunity induced by prior infection, and thus immunoprophylaxis is feasible. A live-attenuated RSV vaccine would be administered intranasally to initiate a mild immunizing infection. This has the advantage of simplicity and safety compared to a parenteral route. It also provides direct stimulation of local respiratory tract immunity, which plays a major role in resistance to RSV. It also abrogates the immunosuppressive effects of RSV-specific maternally-derived serum antibodies, which typically are found in the very young. Also, while the parenteral administration of RSV antigens can sometimes be associated with immuno-pathologic complications (Murphy et al., *Vaccine* 8(5):497–502, 1990), this has never been observed with a live virus.

A formalin-inactivated virus vaccine was tested against RSV in the mid-1960s, but failed to protect against RSV infection or disease, and in fact exacerbated symptoms during subsequent infection by the virus. (Kim et al.,*Am. J. Epidemiol.*, 89:422–434, 1969; Chin et al., *Am J. Epidemiol.*, 89:449–463, 1969; Kapikian et al., *Am. J. Epidemiol.*, 89:405–421, 1969).

More recently, vaccine development for RSV has focused on attenuated RSV mutants. Friedewald et al., (*J. Amer.*

Med. Assoc. 204:690–694, 1968) reported a cold passaged mutant of RSV (cpRSV) which appeared to be sufficiently attenuated to be a candidate vaccine. This mutant exhibited a slightly increased efficiency of growth at 26° C. compared to its wild-type (wt) parental virus, but its replication was neither temperature sensitive nor significantly cold-adapted. The cold-passaged mutant, however, was attenuated for adults. Although satisfactorily attenuated and immunogenic for infants and children who had been previously infected with RSV (i.e., seropositive individuals), the cpRSV mutant retained a low level virulence for the upper respiratory tract of seronegative infants.

Similarly, Gharpure et al., (J. Virol. 3:414–421, 1969) reported the isolation of temperature sensitive RSV (tsRSV) mutants which also were promising vaccine candidates. One mutant, ts-1, was evaluated extensively in the laboratory and in volunteers. The mutant produced asymptomatic infection in adult volunteers and conferred resistance to challenge with wild-type virus 45 days after immunization. Again, while seropositive infants and children underwent asymptomatic infection, seronegative infants developed signs of rhinitis and other mild symptoms. Furthermore, instability of the ts phenotype was detected. Although virus exhibiting a partial or complete loss of temperature sensitivity represented a small proportion of virus recoverable from vaccinees, it was not associated with signs of disease other than mild rhinitis.

These and other studies revealed that certain cold-passaged and temperature sensitive RSV strains were underattenuated and caused mild symptoms of disease in some vaccinees, particularly seronegative infants, while others were overattenuated and failed to replicate sufficiently to elicit a protective immune response, (Wright et al., Infect. Immun., 37:397–400, 1982). Moreover, genetic instability of candidate vaccine mutants has resulted in loss of their temperature sensitive phenotype, further hindering development of effective RSV vaccines. See generally, (Hodes et al., Proc. Soc. Exp. Biol. Med. 145:1158–1164, 1974; McIntosh et al., Pediatr. Res. 8:689–696, 1974; and Belshe et al., J. Med. Virol., 3:101–110, 1978).

As an alternative to live-attenuated RSV vaccines, investigators have also tested subunit vaccine candidates using purified RSV envelope glycoproteins. The glycoproteins induced resistance to RS virus infection in the lungs of cotton rats, (Walsh et al., J. Infect. Dis. 155:1198–1204, 1987), but the antibodies had very weak neutralizing activity and immunization of rodents with purified subunit vaccine led to disease potentiation (Murphy et al., Vaccine 8:497–502, 1990).

Recombinant vaccinia virus vaccines which express the F or G envelope glycoprotein have also been explored. These recombinants express RSV glycoproteins which are indistinguishable from the authentic viral counterpart, and rodents infected intradermally with vaccinia-RSV F and G recombinants developed high levels of specific antibodies that neutralized viral infectivity. Indeed, infection of cotton rats with vaccinia-F recombinants stimulated almost complete resistance to replication of RSV in the lower respiratory tract and significant resistance in the upper tract. (Olmsted et al., Proc. Natl. Acad. Sci. USA 83:7462–7466, 1986). However, immunization of chimpanzees with vaccinia-F and -G recombinant provided almost no protection against RSV challenge in the upper respiratory tract (Collins et al., Vaccine 8:164–168, 1990) and inconsistent protection in the lower respiratory tract (Crowe et al., Vaccine 11:1395–1404, 1993).

Despite these various efforts to develop an effective RSV vaccine, no licensed vaccine has yet been approved for RSV. The unfulfilled promises of prior approaches underscores a need for new strategies to develop RSV vaccines, and in particular methods for manipulating recombinant RSV to incorporate genetic changes that yield new phenotypic properties in viable, attenuated RSV recombinants. However, manipulation of the genomic RNA of RSV and other non-segmented negative-sense RNA viruses has heretofore proven difficult. Major obstacles in this regard include non-infectivity of naked genomic RNA of these viruses and, in the case of RSV, poor viral growth in tissue culture, lengthy replication cycles, virion instability, a complex genome, and a refractory organization of gene products.

Recombinant DNA technology has made it possible to recover infectious non-segmented negative-stranded RNA viruses from cDNA, to genetically manipulate viral clones to construct novel vaccine candidates, and to rapidly evaluate their level of attenuation and phenotypic stability (for reviews, see Conzelmann, J. Gen. Virol. 77:381–89, 1996; Palese et al., Proc. Natl. Acad. Sci. U.S.A. 93:11354–58, 1996). In this context, recombinant rescue has been reported for infectious respiratory syncytial virus (RSV), parainfluenza virus (PIV), rabies virus (RaV), vesicular stomatitis virus (VSV), measles virus (MeV), rinderpest virus and Sendai virus (SeV) from cDNA-encoded antigenomic RNA in the presence of essential viral proteins (see, e.g., Garcin et al., EMBO J. 14:6087–6094, 1995; Lawson et al., Proc. Natl. Acad. Sci. U.S.A. 92:4477–81, 1995; Radecke et al., EMBO J. 14:5773–5784, 1995; Schnell et al., EMBO J. 13:4195–203, 1994; Whelan et al., Proc. Natl. Acad. Sci. U.S.A. 92:8388–92, 1995; Hoffman et al., J Virol. 71:4272–4277, 1997; Pecters et al., J. Virol. 73:5001–5009, 1999; Kato et al., Genes to Cells 1:569–579, 1996; Roberts et al., Virology 247(1), 1–6, 1998; Baron et al., J Virol. 71:1265–1271, 1997; International Publication No. WO 97/06270; U.S. Provisional Patent Application No. 60/007, 083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. Pat. No. 5,993,824, issued Nov. 30, 1999 (corresponding to International Publication No. WO 98/02530); U.S. patent application Ser. No. 09/291,894, filed by Collins et al. on Apr. 13, 1999; U.S. Provisional Patent Application No. 60/129,006, filed by Murphy et al. on Apr. 13, 1999; Collins, et al., Proc Nat. Acad. Sci. USA 92:11563–11567, 1995; Bukreyev, et al., J. Virol. 70:6634–41, 1996, Juhasz et al., J. Virol. 71(8):5814–5819, 1997; Durbin et al., Virology 235:323–332, 1997; He et al. Virology 237:249–260, 1997; Baron et al. J. Virol. 71:1265–1271, 1997; Whitehead et al., Virology 247(2): 232–9, 1998a; Buchholz et al. J. Virol. 73:251–9, 1999; Whitehead et al., J. Virol. 72(5):4467–4471, 1998b; Jin et al. Virology 251:206–214, 1998; and Whitehead et al., J. Virol. 73:(4)3438–3442, 1999, and Bukreyev, et al., Proc. Nat. Acad. Sci. USA 96:2367–72, 1999; Collins et al., Virology 259:251–255, 1999, each incorporated herein by reference in its entirety for all purposes).

Based on these developments in recombinant DNA technology, it is now possible to recover infectious RSV from cDNA and to design and implement various genetic manipulations to RSV clones to construct novel vaccine candidates. Thereafter, the level of attenuation and phenotypic stability, among other desired phenotypic characteristics, can be evaluated. The challenge which thus presents itself is to develop a broad and diverse menu of genetic manipulations that can be employed, alone or in combination with other types of genetic manipulations, to construct infectious, attenuated RSV clones that are useful for broad vaccine use. In this context, an urgent need remains in the art for additional tools and methods that will allow engineering of safe and effective vaccines to alleviate the serious health problems attributable to RSV. Surprisingly, the present invention fulfills this need by providing additional tools for constructing infectious, attenuated RSV vaccine candidates.

SUMMARY OF THE INVENTION

The present invention provides recombinant RSV (rRSV) in which expression of the second translational open reading frame encoded by the M2 gene (M2ORF2) (Collins and Wertz, *J. Virol.* 54:65–71, 1985; Collins et al., *J. Gen. Virol.* 71:3015–3020, 1990, Collins et al., *Proc. Natl. Acad. Sci. USA* 93:81–85, 1996, each incorporated herein by reference) is reduced or ablated to yield novel RSV vaccine candidates. In preferred aspects of the invention, expression of M2 ORF2 is reduced or ablated by modifying a recombinant RSV genome or antigenome to incorporate a frame shift mutation or one or stop codons in M2 ORF2 yielding a "knock out" viral clone. Alternatively, M2 ORF2 is deleted in whole or in part to render the M2-2 protein partially or entirely non-functional or to disrupt its expression altogether to yield a "deletion mutant" RSV. Alternatively, the M2-2 ORF may be transpositioned in the genome or antigenome to a more promoter-proximal or promoter-distal position compared to the natural gene order position of M2-2 gene to up-regulate or down-regulate expression of the M2-2 ORF. In additional embodiments, the M2-2 ORF is incorporated in the genome or antigenome as a separate gene having a gene start and gene end gene end signal, which modification results in up-regulation of the M2-2 ORF.

The recombinant RSV of the invention having mutations in M2 ORF2 possess highly desirable phenotypic characteristics for vaccine development. The above identified modifications in the recombinant genome or antigenome specify one or more desired phenotypic changes in the resulting virus or subviral particle. Vaccine candidates are thus generated that exhibit one or more characteristics identified as (i) a change in mRNA transcription, (ii) a change in the level of viral protein expression; (iii) a change in genomic or antigenomic RNA replication, (iv) a change in viral growth characteristics, (v), a change in viral plaque size, and/or (vi) a change in cytopathogenicity.

In exemplary RSV recombinants described herein, desired phenotypic changes include attenuation of viral growth compared to growth of a corresponding wild-type or mutant parental RSV strain. In more detailed aspects, viral growth in cell culture may be attenuated by approximately 10-fold or more attributable to mutations in M2 ORF2. Kinetics of viral growth are also shown to be modified in a manner that is beneficial for vaccine development.

Also described herein are recombinant RSV that exhibit delayed kinetics of viral mRNA synthesis compared to kinetics of mRNA synthesis of corresponding wild-type or mutant parental RSV strains. Despite these delayed transcription kinetics, these novel vaccine candidates exhibit an increase in cumulative mRNA synthesis compared to parental virus. These phenotypic changes typically are associated with an increase in viral protein accumulation in infected cells compared to protein accumulation in cells infected with wild-type or other parental RSV strains. At the same time, viral RNA replication is reduced in M2 ORF2 mutants compared to that of a parental RSV strain, whereby accumulation of genomic or antigenomic RNA is reduced.

Within preferred aspects of the invention, recombinant M2 ORF2 deletion and "knock out" RSV are engineered to express undiminished or, more typically, increased levels of viral antigen(s) while also exhibiting an attenuated phenotype. Immunogenic potential is thus preserved due to the undiminished or increased mRNA transcription and antigen expression, while attenuation is achieved through concomitant reductions in RNA replication and virus growth. This novel suite of phenotypic traits is highly desired for vaccine development. Other useful phenotypic changes that are observed in M2 ORF2 deletion and knock out mutants include a large plaque phenotype and altered cytopathogenicity compared to corresponding wild-type or mutant parental RSV strains.

In related aspects of the invention, a method for producing one or more purified RSV protein(s) is provided which involves infecting a host cell permissive of RSV infection with a recombinant, M2-ORF 2 deletion or knock out mutant RSV under conditions that allow for RSV propagation in the infected cell. After a period of replication in culture, the cells are lysed and recombinant RSV is isolated therefrom: One or more desired RSV protein(s) is purified after isolation of the virus, yielding one or more RSV protein(s) for vaccine, diagnostic and other uses.

In combination with the phenotypic effects provided in recombinant RSV bearing M2 ORF2 deletion or knock out mutations, it is often desirable to adjust the attenuation phenotype by introducing additional mutations that increase or decrease attenuation of the recombinant virus. Thus, candidate vaccine strains can be further attenuated by incorporation of at least one, and preferably two or more different attenuating mutations, for example mutations identified from a panel of known, biologically derived mutant RSV strains. Preferred human mutant RSV strains are cold passaged (cp) and/or temperature sensitive (ts) mutants, for example the mutants designated "cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579)" (each deposited under the terms of the Budapest Treaty with the American Type Culture Collection (ATCC) of 10801 University Boulevard, Manassas, Va. 20110-2209, U.S.A., and granted the above identified accession numbers). From this exemplary panel of biologically derived mutants, a large "menu" of attenuating mutations is provided, each of which can be combined with any other mutation(s) within the panel for calibrating the level of attenuation and other desirable phenotypes in M2 ORF2 deletion and knock out mutants for vaccine use. Additional mutations which can be thus adopted or transferred to M2 ORF2 deletion and knock out mutants within the invention may be identified in various temperature sensitive (ts), cold passaged (cp), small plaque (sp), cold-adapted (ca) or host-range restricted (hr) mutant RSV strains. Additional attenuating mutations may be identified in non-RSV negative stranded RNA viruses and incorporated in RSV mutants of the invention by mapping the mutation to a corresponding, homologous site in the recipient RSV genome or antigenome and mutating the existing sequence in the recipient to the mutant genotype (either by an identical or conservative mutation), as described in U.S. Provisional Patent Application Serial No. 60/129,006, filed Apr. 13, 1999. Additional useful mutations can be determined empirically by mutational analysis using recombinant minigenome systems and infectious virus as described in the references incorporated herein.

M2 ORF2 deletion and knock out mutants of the invention selected for vaccine use often have at least two and sometimes three or more attenuating mutations to achieve a satisfactory level of attenuation for broad clinical use. In one embodiment, at least one attenuating mutation occurs in the RSV polymerase gene L (either in the donor or recipient gene) and involves one or more nucleotide substitution(s) specifying an amino acid change in the polymerase protein specifying an attenuation phenotype which may or may not involve a temperature-sensitive (ts) phenotype. Recombinant RSV of the invention may incorporate a ts mutation in any additional RSV gene besides L, for example in the M2 gene. However, preferred vaccine candidates in this context incorporate one or more nucleotide substitutions in the large polymerase gene L resulting in an amino acid change at amino acid Asn43, Cys319, Phe521, Gln831, Met1169, Tyr1321 and/or His1690, as exemplified by the changes, Ile for Asn43, Leu for Phe521, Leu for Gln831, Val for Met1169, and Asn for Tyr1321. Other alternative amino acid changes, particularly conservative changes with respect to identified mutant residues, at these positions can of course be made to yield a similar effect as the identified, mutant substitution. Additional desired mutations for incorporation into recombinant RSV of the invention include attenuating mutations specifying an amino acid substitution at Val267 in the RSV N gene, Glu218 and/or Thr523 in the RSV F gene, and a nucleotide substitution in the gene-start sequence of gene M2. Any combination of one or more of the attenuating mutations identified herein, up to and including a full complement of these mutations, may be incorporated in M2 ORF2 deletion or knock out RSV to yield a suitably attenuated recombinant virus for use in selected populations or broad populations of vaccine recipients.

Attenuating mutations may be selected in coding portions of an M2 ORF2 deletion or knock out mutant genome or antigenome or in non-coding regions such as a cis-regulatory sequence. Exemplary non-coding mutations include single or multiple base changes in a gene start sequence, as exemplified by a single or multiple base substitution in the M2 gene start sequence at nucleotide 7605 (nucleotide 7606 in an exemplary recombinant sequence).

In addition to the above described mutations, infectious M2 ORF2 deletion and knock out mutants according to the invention can incorporate heterologous, coding or non-coding nucleotide sequences from any RSV or RSV-like virus, e.g., human, bovine, ovine, murine (pneumonia virus of mice), or avian (turkey rhinotracheitis virus) pneumovirus, or from another enveloped virus, e.g., parainfluenza virus (PIV). Exemplary heterologous sequences include RSV sequences from one human RSV strain combined with sequences from a different human RSV strain in an M2 ORF2 deletion or knock out mutants. For example, recombinant RSV of the invention may incorporate sequences from two or more wild-type or mutant RSV strains, for example mutant strains selected from cpts RSV 248, cpts 248/404, cpts 248/955, cpts RSV 530, cpts 530/1009, or cpts 530/1030. Alternatively, M2 ORF2 deletion and knock out RSV mutants may incorporate sequences from two or more, wild-type or mutant human RSV subgroups, for example a combination of human RSV subgroup A and subgroup B sequences (see, International Application No. PCT/US/08802 and related U.S. patent application Nos. 60/021,773, 60/046,141, 60/047,634, Ser. Nos. 08/892,403, 09/291,894, each incorporated herein by reference). In yet additional aspects, one or more human RSV coding or non-coding polynucleotides are substituted with a counterpart sequence from a heterologous RSV or non-RSV virus, alone or in combination with one or more selected attenuating mutations, e.g., cp and/or ts mutations, to yield novel attenuated vaccine strains.

In related aspects of the invention, the disclosed modifications relating to M2-2 are incorporated within chimeric human-bovine RSV, which are recombinantly engineered to incorporate nucleotide sequences from both human and bovine RSV strains to produce an infectious, chimeric virus or subviral particle. Exemplary human-bovine chimeric RSV of the invention incorporate a chimeric RSV genome or antigenome comprising both human and bovine polynucleotide sequences, as well as a major nucleocapsid (N) protein, a nucleocapsid phosphoprotein (P), a large polymerase protein (L), and a RNA polymerase elongation factor. Additional RSV proteins may be included in various combinations to provide a range of infectious subviral particles, up to a complete viral particle or a viral particle containing supernumerary proteins, antigenic determinants or other additional components.

Chimeric human-bovine RSV for use within the invention are generally described in U.S. Patent Application entitled PRODUCTION OF ATTENUATED, HUMAN-BOVINE CHIMERIC RESPIRATORY SYNCYTIAL VIRUS VACCINES, filed by Bucholz et al. on Jun. 23, 2000, and in its priority U.S. Provisional Patent Application Serial No. 60/143,132 (each incorporated herein by reference). These chimeric recombinant RSV include a partial or complete "background" RSV genome or antigenome derived from or patterned after a human or bovine RSV strain or subgroup virus combined with one or more heterologous gene(s) or genome segment(s) of a different RSV strain or subgroup virus to form the human-bovine chimeric RSV genome or antigenome. In certain aspects of the invention, chimeric RSV incorporate a partial or complete bovine RSV background genome or antigenome combined with one or more heterologous gene(s) or genome segment(s) from a human RSV. In alternate aspects of the invention M2 ORF2 deletion and knock out RSV incorporate a partial or complete human RSV background genome or antigenome combined with one or more heterologous gene(s) or genome segment(s) from a bovine RSV.

Yet additional aspects of the invention involve changing the position of a gene or altering gene order to create or modify a M2 ORF2 deletion or knock out mutant RSV. In this context, a number of the foregoing incorporated references have focused on modification of the naturally-occurring order in RSV and other viruses. For example, in RSV the NS1, NS2, SH and G genes were deleted individually, and the NS1 and NS2 gene were deleted together, thereby shifting the position of each downstream gene relative to the viral promoter. For example, when NS1 and NS2 are deleted together, N is moved from position 3 to position 1, P from position 4 to position 2, and so on. Alternatively, deletion of any other gene within the gene order will affect the position (relative to the promoter) only of those genes which are located further downstream. For example, SH occupies position 6 in wild type virus, and its deletion does not affect M at position 5 (or any other upstream gene) but moves G from position 7 to 6 relative to the promoter. It should be noted that gene deletion also can occur (rarely) in a biologically-derived mutant virus. For example, a subgroup B RSV that had been passaged extensively in cell culture spontaneously deleted the SH and G genes (Karron et al., Proc. Natl. Acad. Sci. USA 94:13961–13966, 1997; incorporated herein by reference). Note that "upstream" and "downstream" refer to the promoter-proximal and promoter-distal directions, respectively (the promoter is at the 3' leader end of negative-sense genomic RNA).

Gene order shifting modifications (i.e., positional modifications moving one or more genes to a more promoter-proximal or promoter-distal location in the recombinant viral genome) to create or modify M2 ORF2 deletion and knock out RSV of the invention result in viruses with altered biological properties. For example, RSV lacking NS1, NS2, SH, G, NS1 and NS2 together, or SH and G together, have been shown to be attenuated in vitro, in vivo, or both. It is likely that this phenotype was due primarily to the loss of expression of the specific viral protein. However, the altered gene map also likely contributed to the observed phenotype. This effect is well-illustrated by the SH-deletion virus, which grew more efficiently than wild type in some cell types, probably due to an increase in the efficiency of transcription, replication or both resulting from the gene deletion and resulting change in gene order and possibly genome size. In other viruses, such as RSV in which NS1 and/or NS2 were deleted, altered growth that might have occurred due to the change in gene order likely was obscured by the more dominant phenotype due to the loss of expression of the RSV protein(s).

Yet additional changes will be introduced to change the gene order of M2 ORF2 deletion and knock out RSV in an effort to improve its properties as a live-attenuated vaccine (see, U.S. Provisional Patent Application Ser. No. 60/213, 708 entitled RESPIRATORY SYNCYTIAL VIRUS VACCINES EXPRESSING PROTECTIVE ANTIGENS FROM PROMOTOR-PROXIMAL GENES, filed by Krempl et al., Jun. 23, 2000, incorporated herein by reference). In particular, the G and F genes may be shifted, singly and in tandem, to a more promoter-proximal position relative to their wild-type gene order. These two proteins normally occupy positions 7 (G) and 8 (F) in the RSV gene order (NS1-NS2-N-P-M-SH-G-F-M2-L). In order to increase the possibility of successful recovery, exemplary shifting manipulations have been performed in a version of RSV in which the SH gene had been deleted (Whitehead et al., *J. Virol.,* 73:3438–42 (1999), incorporated herein by reference). This facilitates recovery because this virus makes larger plaques in vitro (Bukreyev et al., *J. Virol.,* 71:8973–82 (1997), incorporated herein by reference). G and F were then moved individually to position 1, or were moved together to positions 1 and 2, respectively. Surprisingly, recombinant RSV were readily recovered in which G or F were moved to position 1, or in which G and F were moved to positions 1 and 2, respectively.

Similarly extensive modifications in gene order also have been achieved with two highly attenuated vaccine candidates in which the NS2 gene was deleted on its own, or in which the NS1 and NS2 genes were deleted together. In these two vaccine candidates, the G and F glycoproteins were moved together to positions 1 and 2 respectively, and the G, F and SH glycoproteins were deleted from their original downstream position. Thus, the recovered viruses G1F2ΔNS2ΔSH and G1F2/ΔNS1ΔNS2ΔSH had two and three genes deleted respectively in addition to the shift of the G and F genes. To illustrate the extent of the changes involved, the gene orders of wild type RSV (NS1-NS2-N-P-M-SH-G-F-M2-L) and the G1F2/ΔNS2ΔSH virus (G-F-NS1-N-P-M-M2-L) or the ΔNS1ΔNS2ΔSH (G-F-N-P-M-M2-L) can be compared. This shows that the positions of most or all of the genes relative to the promoter were changed. Nonetheless, these highly attenuated derivatives retained the capacity to be grown in cell culture.

In other detailed aspects of the invention, M2 ORF2 deletion and knock out mutants are employed as "vectors" for protective antigens of other pathogens, particularly respiratory tract pathogens such as parainfluenza virus (PIV). For example, recombinant RSV having a M2 ORF2 deletion or knock out may be engineered which incorporate sequences that encode protective antigens from PIV to produce infectious, attenuated vaccine virus. The cloning of PIV cDNA and other disclosure supplemental to the instant invention is provided in United States Patent Application entitled PRODUCTION OF PARAINFLUENZA VIRUS VACCINES FROM CLONED NUCLEOTIDE SEQUENCES, filed May 22, 1998, Ser. No. 09/083,793 (corresponding to International Publication No. WO 98/53078) and its priority, provisional application filed May 23, 1997, Serial No. 60/047,575, U.S. Provisional Patent Application Ser. No. 60/143,134 entitled ATTENUATED HUMAN-BOVINE CHIMERIC PARAINFLUENZA VIRUS VACCINES, filed by Baily et al. on Jul. 9, 1999 and U.S. Provisional Patent Application Ser. No. 09/350,821 entitled RECOMBINANT PARAINFLUENZA VIRUS VACCINES ATTENUATED BY DELETION OR ABLATION OF A NON-ESSENTIAL GENE, filed by Durbin et al. on Jul. 9, 1999; each incorporated herein by reference. This disclosure includes description of the following plasmids that may be employed to produce infectious PIV viral clones or to provide a source of PIV genes or genome segments for use within the invention: p3/7(131) (ATCC 97990); p3/7(131)2G (ATCC 97989); and p218(131) (ATCC 97991); each deposited under the terms of the Budapest Treaty with the American Type Culture Collection (ATCC) of 10801 University Boulevard, Manassas, Va. 20110-2209, U.S.A., and granted the above identified accession numbers.

According to this aspect of the invention, M2 ORF2 deletion and knock out mutants RSV are provided which incorporate at least one PIV sequence, for example a polynucleotide containing sequences from either or both PIV1 and PIV2 or PIV1 and PIV3. Individual genes of RSV may be replaced with counterpart genes from human PIV, such as the F glycoprotein genes of PIV1, PIV2, or PIV3. Alternatively, a selected, heterologous genome segment, such as a cytoplasmic tail, transmembrane domain or ectodomain of substituted for a counterpart genome segment in, e.g., the same gene in RSV, within a different gene in RSV, or into a non-coding sequence of the RSV genome or antigenome. In one embodiment, a genome segment from an F gene of HPIV3 is substituted for a counterpart human RSV genome segment to yield constructs encoding chimeric proteins, e.g. fusion proteins having a cytoplasmic tail and/or transmembrane domain of RSV fused to an ectodomain of PIV to yield a novel attenuated virus, and/or a multivalent vaccine immunogenic against both PIV and RSV. Alternatively, one or more PIV3 gene(s) or genome segment(s) can be added to a partial or complete, chimeric or non-chimeric RSV genome or antigenome.

To construct chimeric RSV, heterologous genes may be added or substituted in whole or in part to the background genome or antigenome. In the case of chimeras generated by substitution, a selected gene or genome segment encoding a protein or protein region (e.g., a cytoplasmic tail, transmembrane domain or ectodomain, an epitopic site or region, a binding site or region, an active site or region containing an active site, etc.) from a human or bovine RSV is substituted for a counterpart gene or genome segment in the background RSV genome or antigenome to yield novel recombinants having desired phenotypic changes compared to one or both of the respective wild-type (or mutant parent) RSV strains.

As used herein, "counterpart" genes or, genome segments refer to counterpart polynucleotides from different RSV sources that encode homologous or equivalent proteins or protein domains, epitopes, or amino acid residues, or which represent homologous or equivalent cis-acting signals which may include but are not limited to species and allelic variants among different RSV subgroups or strains.

In other alternate embodiments, M2 ORF2 deletion and knock out RSV designed as vectors for carrying heterologous antigenic determinants incorporate one or more antigenic determinants of a non-RSV pathogen, such as a human parainfluenza virus (HPIV). In one exemplary embodiment, one or more HPIV1, HPIV2, or HPIV3 gene(s) or genome segment(s) encoding one or more HN and/or F glycoprotein(s) or antigenic domain(s), fragment(s) or epitope(s) thereof is/are added to or incorporated within the partial or complete HRSV vector genome or antigenome. In more detailed embodiments, a transcription unit comprising an open reading frame (ORF) of an HPIV1, HPIV2, or HPIV3 HN or F gene is added to or incorporated within the chimeric HRSV vector genome or antigenome.

Mutations incorporated within cDNAs, vectors and viral particles of the invention can be introduced individually or in combination into a full-length M2 ORF2 deletion or knock out mutant and the phenotypes of rescued virus containing the introduced mutations can be readily determined. In exemplary embodiments, amino acid changes displayed by attenuated, biologically-derived viruses versus a wild-type RSV, for example changes exhibited by cpRSV or tsRSV, are incorporated in combination within a recombinant M2 ORF2 deletion or knock out mutant RSV to yield a desired level of attenuation for vaccine use.

The present invention thus provides M2 ORF2 deletion and knock out mutant RSV clones, vectors and particles which may incorporate multiple, phenotype-specific mutations introduced in selected combinations into the recombinant genome or antigenome to produce a suitably attenuated, infectious virus or subviral particle. This process, coupled with routine phenotypic evaluation, provides M2 ORF2 deletion and knock out mutants having such desired characteristics as attenuation, temperature sensitivity, altered immunogenicity, cold-adaptation, small plaque size, host range restriction, etc. Mutations thus identified are compiled into a "menu" and introduced in various combinations to calibrate a vaccine virus to a selected level of attenuation, immunogenicity and stability.

In yet additional aspects of the invention, M2 ORF2 deletion and knock out mutants, with or without additional attenuating mutations, are constructed to have a nucleotide modification to yield a desired phenotypic, structural, or functional change. Typically, the selected nucleotide modification will specify a phenotypic change, for example a change in growth characteristics, attenuation, temperature-sensitivity, cold-adaptation, plaque size, host range restriction, or immunogenicity. Structural changes in this context include introduction or ablation of restriction sites into RSV encoding cDNAs for ease of manipulation and identification.

In preferred embodiments, nucleotide changes within the genome or antigenome of an M2 ORF2 deletion or knock out mutant include modification of an additional viral gene by partial or complete deletion of the gene or reduction or ablation (knock-out) of its expression. Target genes for mutation in this context include the attachment (G) protein, fusion (F) protein, small hydrophobic (SH), RNA binding protein (N), phosphoprotein (P), the large polymerase protein (L), the transcription elongation factor (M2 ORF1), the matrix (M) protein, and two nonstructural proteins, NS1 and NS2. Each of these proteins can be selectively deleted, substituted or rearranged, in whole or in part, alone or in combination with other desired modifications, to achieve novel RSV recombinants.

In one aspect of the invention, an SH, NS1, NS2, or G gene is modified in an M2 ORF2 deletion or knock out mutant RSV. For example, each of these genes may be deleted in whole or in part or its expression reduced or ablated (e.g., by introduction of a stop codon or frame shift mutation or alteration of a transcriptional or translational start site) to alter the phenotype of the resultant recombinant clone to improve growth, attenuation, immunogenicity or other desired phenotypic characteristics. For example, deletion of the SH gene in the recombinant genome or antigenome will yield a vaccine candidate having novel phenotypic characteristics such as enhanced growth in vitro and/or attenuation in vivo. In a related aspect, an SH gene deletion, or deletion of another selected non-essential gene or genome segment such as a NS1 or NS2 gene, is constructed in an M2 ORF2 deletion or knock out mutant, alone or in combination with one or more different mutations specifying an attenuated phenotype, e.g., a point mutation adopted directly (or in modified form, e.g., by introducing multiple nucleotide changes in a codon specifying the mutation) from a biologically derived attenuated RSV mutant. For example, the SH, NS1, NS2 or G gene may be deleted in combination with one or more cp and/or ts mutations adopted from cpts248/404, cpts530/1009, cpts530/030 or another selected mutant RSV strain, to yield a recombinant RSV exhibiting increased yield of virus, enhanced attenuation, improved immunogenicity and genetic resistance to reversion from an attenuated phenotype due to the combined effects of the different mutations.

Alternative nucleotide modifications in M2 ORF2 deletion and knock out RSV mutants of the invention can include a deletion, insertion, addition or rearrangement of a cis-acting regulatory sequence for a selected gene in the recombinant genome or antigenome. In one example, a cis-acting regulatory sequence of one RSV gene is changed to correspond to a heterologous regulatory sequence, which may be a counterpart cis-acting regulatory sequence of the same gene in a different RSV or a cis-acting regulatory sequence of a different RSV gene. For example, a gene end signal may be modified by conversion or substitution to a gene end signal of a different gene in the same RSV strain. In other embodiments, the nucleotide modification may comprise an insertion, deletion, substitution, or rearrangement of a translational start site within the recombinant genome or antigenome, e.g., to ablate an alternative translational start site for a selected form of a protein. In one example, the translational start site for a secreted form of the RSV G protein is ablated to modify expression of this form of the G protein and thereby produce desired in vivo effects.

In addition, a variety of other genetic alterations can be produced in a RSV genome or antigenome having a deletion or knock-out of M2 ORF2, alone or together with one or more attenuating mutations adopted from a biologically derived mutant RSV. For example, genes or genome segments from non-RSV sources may be inserted in whole or in part. Alternatively, the order of genes can be changed, gene overlap removed, or an RSV genome promoter replaced with its antigenome counterpart. Different or additional modifications in the recombinant genome or antigenome can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences. In yet additional aspects, polynucleotide molecules or vectors encoding the recombinant RSV genome or antigenome can be modified to encode non-RSV sequences, e.g., a cytokine, a T-helper epitope, a restriction site marker, or a protein of a microbial pathogen (e.g., virus, bacterium or fungus) capable of eliciting a protective immune response in an intended host. Non-RSV genes of interest include those encoding cytokines (e.g., IL-2 through IL-18, especially IL-2, IL-4, IL-6 and IL-12, IL-18, etc.), gamma-interferon, GM-CSF, chemokines and proteins rich in T helper cell epitopes (see, e.g., U.S. Provisional Patent Application Serial No. 60/143,425, incorporated herein by reference). This provides the ability to modify and improve the immune responses against RSV both quantitatively and qualitatively.

All of the foregoing modifications within a recombinant RSV genome or antigenome, including nucleotide insertions, rearrangements, deletions or substitutions yielding point mutations, site-specific nucleotide changes, and changes involving entire genes or genome segments, may be made to either a heterologous donor gene or genome segment, or in a partial or complete recipient or background genome or antigenome. In each case, these alterations will preferably specify one or more phenotypic change(s) in the resulting recombinant RSV, such as a phenotypic change that results in attenuation, temperature-sensitivity, cold-adaptation, small plaque size, host range restriction, alteration in gene expression, or a change in an immunogenic epitope.

In related aspects of the invention, compositions (e.g., isolated polynucleotides and vectors incorporating an RSV-encoding cDNA) and methods are provided for producing an isolated infectious recombinant RSV bearing an attenuating, M2 ORF2 deletion or knock out mutation. Included within these aspects of the invention are novel, isolated polynucleotide molecules and vectors incorporating such molecules that comprise a RSV genome or antigenome which is modified by a partial or complete deletion of M2 ORF2 or one or more nucleotide changes that reduce or ablate expression of M2 ORF2. Also provided is the same or different expression vector comprising one or more isolated polynucleotide molecules encoding N, P, L and RNA polymerase elongation factor proteins. These proteins also can be expressed directly from the genome or antigenome cDNA. The vector(s) is/are preferably expressed or coexpressed in a cell or cell-free lysate, thereby producing an infectious M2 ORF2 deletion or knock out mutant RSV particle or subviral particle.

The above methods and compositions for producing M2 ORF2 deletion and knock out mutant RSV yield infectious viral or subviral particles, or derivatives thereof. An infectious virus is comparable to the authentic RSV virus particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, L and M2(ORF1) proteins is an example of a subviral particle which can initiate an infection if introduced into the cytoplasm of cells. Subviral particles provided within the invention include viral particles which lack one or more protein(s), protein segment(s), or other viral component(s) not essential for infectivity.

In other embodiments the invention provides a cell or cell-free lysate containing an expression vector which comprises an isolated polynucleotide molecule encoding an M2 ORF2 deletion or knock out mutant RSV genome or antigenome as described above, and an expression vector (the same or different vector) which comprises one or more isolated polynucleotide molecules encoding the N, P, L and RNA polymerase elongation factor proteins of RSV. One or more of these proteins also can be expressed from the genome or antigenome cDNA. Upon expression the genome or antigenome and N, P, L, and RNA polymerase elongation factor proteins combine to produce an infectious RSV viral or subviral particle.

The recombinant RSV of the invention are useful in various compositions to generate a desired immune response against RSV in a host susceptible to RSV infection. Attenuated M2 ORF2 deletion and knock out mutant RSVs of the invention are capable of eliciting a protective immune response in an infected human host, yet are sufficiently attenuated so as to not cause unacceptable symptoms of severe respiratory disease in the immunized host. The attenuated virus or subviral particle may be present in a cell culture supernatant, isolated from the culture, or partially or completely purified. The virus may also be lyophilized, and can be combined with a variety of other components for storage or delivery to a host, as desired.

The invention further provides novel vaccines comprising a physiologically acceptable carrier and/or adjuvant and an isolated attenuated M2 ORF2 deletion or knock out mutant RSV particle or subviral particle. In preferred embodiments, the vaccine is comprised of an M2 ORF2 deletion or knock out mutant RSV having at least one, and preferably two or more attenuating mutations or other nucleotide modifications as described above to achieve a suitable balance of attenuation and immunogenicity. The vaccine can be formulated in a dose of $10^3$ to $10^6$ PFU or more of attenuated virus. The vaccine may comprise attenuated M2 ORF2 deletion or knock out virus that elicits an immune response against a single RSV strain or antigenic subgroup, e.g. A or B, or against multiple RSV strains or subgroups. In this regard, M2 ORF2 deletion and knock out mutant RSV can be combined in vaccine formulations with other RSV vaccine strains or subgroups having different immunogenic characteristics for more effective protection against one or multiple RSV strains or subgroups.

In related aspects, the invention provides a method for stimulating the immune system of an individual to elicit an immune response against RSV in a mammalian subject. The method comprises administering a formulation of an immunologically sufficient amount of an attenuated, M2 ORF2 deletion or knock out mutant RSV in a physiologically acceptable carrier and/or adjuvant. In one embodiment, the immunogenic composition is a vaccine comprised of an M2 ORF2 deletion or knock out mutant RSV having at least one, and preferably two or more attenuating mutations or other nucleotide modifications specifying a desired phenotype as described above. The vaccine can be formulated in a dose of $10^3$ to $10^6$ PFU or more of attenuated virus. The vaccine may comprise attenuated M2 ORF2 deletion or knock out mutant RSV virus that elicits an immune response against a single RSV strain or antigenic subgroup, e.g. A or B, or against multiple RSV strains or subgroups. M2 ORF2 deletion and knock out mutants can be combined with RSV having different immunogenic characteristics in a vaccine mixture, or administered separately in a coordinated treatment protocol, to elicit more effective protection against one RSV strain, or against multiple RSV strains or subgroups. Preferably the immunogenic composition is administered to the upper respiratory tract, e.g., by spray, droplet or aerosol.

Often, the composition will be administered to an individual seronegative for antibodies to RSV or possessing transplacentally acquired maternal antibodies to RSV.

DESCRIPTION OF THE SPECIFIC EMBODIMENTS

Figure 1:
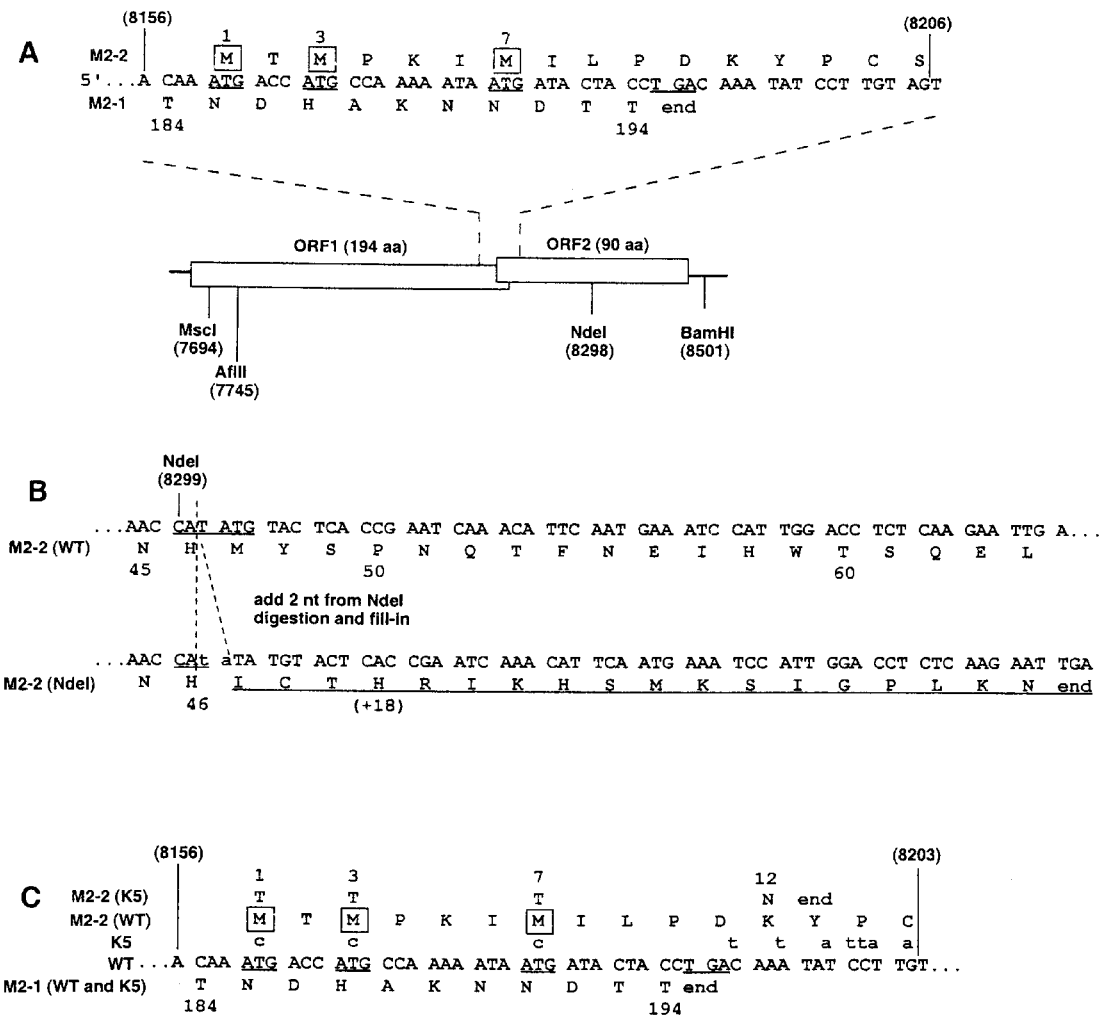
FIG. 1 depicts construction of the NdeI and KS mutations, which interrupt M2 ORF2. Nt sequences are in positive-sense and blocked in triplets according to amino acid coding in ORF2. Nt positions relative to the complete 15,223-nt recombinant antigenome are in parentheses. Other numbers refer to amino acid positions in the 194-amino acid M2-1 protein or 90-amino acid M2-2 protein. Panel A is a diagram of the two overlapping M2 ORFs. In the sequence at the top, the three potential translational start sites for M2-2 are underlined and their encoded methionine residues are boxed. The termination codon for ORF1 is also underlined. In the diagram, restriction sites used for mutagenesis and cloning are indicated. (SEQ ID NO. 3): ACAAATGACCATGC-CAAAAATAATGATACTACCTGA-CAAATATCCTTGTAGT. (SEQ ID NO. 6): TNDHAKNNDTT. Panel B depicts construction of the NdeI mutation. The NdeI site at position 8299 in the middle of the M2-2 ORF was opened, filled in and relegated, which added two nt (lower case) to codon 47 of M2-2. This shifted the register to another reading frame, which was open for 18 additional codons encoding non-M2-2 amino acids (underlined). (SEQ ID NO. 4): AACCATATGTACTCAC-CGAATCAAACATTCAATGAAATCCATTG-GACCTCTCAAGAATTGA. (SEQ ID NO. 7): NHMYSP-NQTFNEIHWTSQEL. (SEQ ID NO. 5): AACCATATATGTACTCACCGAATCAAA-CATTCAATGAAATCCATTGGACCTCTCA AGAAT-TGA. (SEQ ID NO. 8): NHICTHRIKHSMKSIGPLKN. Panel C depicts construction of the K5 mutation. The sequence shows the junction between ORF1 and ORF2, as in Panel A. Potential ORF2 initiation codons in the wt parent are underlined, as is the ORF1 termination codon. Nt changes in K5 are indicated above their wt counterparts. The three potential initiation codons for ORF2, codons 1, 3 and 7, were changed to ACG, which had no effect on amino acid coding in ORF 1. The next potential methionyl start site in ORF2 is at codon 30. In addition, stop codons were introduced into all three frames immediately downstream of the M2-1 termination codon. In combination, these mutations had the effect of changing M2-2 amino acid 12 from K to N and terminating at codon 13.

The present invention provides recombinant RSV (rRSV) in which expression of M2ORF2 gene, newly characterized herein to encode a transcription/replication regulatory factor M2-2, is reduced or ablated to yield an assemblage of novel RSV vaccine candidates. Expression of M2 ORF2 is reduced or ablated by modifying a recombinant RSV genome or antigenome to incorporate a frame shift mutation, or one or more stop codons in M2 ORF2. Other alterations to achieve disruption of M2 ORF2 expression or M2-2 protein expression or function to generate attenuated RSV vaccine candidates include partial or complete deletion of the M2 ORF2 coding sequence, in whole or in part, to render the M2-2 protein partially or entirely non-functional or terminate its expression. Alternatively, expression of the M2-2 gene can be up-regulated or down-regulated in a recombinant RSV, for example by placing the M2-2 ORF in a more promoter-proximal or promoter-distal position, respectively in the recombinant genome or antigenome. Upregulation of M2-2 can also be achieved by constructing the genome or antigenome to include the M2-2 ORF as a separate gene with its own gene start end gene end signals.

RSV is generally characterized as an enveloped nonsegmented negative strand RNA virus of the paramyxovirus family (Collins, et al., *Fields Virology* 2:1313–1352, 1996, incorporated herein by reference). Its genome, which is 15,222 nucleotides (nt) in length for the well known strain A2, is transcribed into 10 messenger RNAs that were previously shown to encode 10 proteins (Collins, et al., *Fields Virology* 2:1313–1352, 1996; Atreya, et al., *J. Virol.* 72:1452–61, 1998; Bukreyev, et al., *J. Virol.* 71:8973–82, 1997; Collins, et al., *Proc. Natl. Acad. Sci. USA* 93:81–5, 1996; Teng and Collins, *J. Virol.* 72:5707–16, 1998; Teng and Collins, *J. Virol.* 73:466–473, 1999; Whitehead, et al., *J. Virol.* 73:3438–42, 1999, each incorporated herein by reference).

As used herein, "RSV gene" generally refers to a portion of the RSV genome encoding an mRNA and typically begins at the upstream end with the 10-nucleotide gene-start (GS) signal and ends at the downstream end with the 12 to 13-nucleotide gene-end (GE) signal. Ten such genes for use within the invention are known for RSV, namely NS1, NS2, N, P, M, SH, G, F, M2 and L. The term "gene" is also used herein to refer to a "translational open reading frame" (ORF). ORF is more specifically defined as a translational open reading frame encoding a significant RSV protein, of which 11 are currently recognized: NS1, NS2, N, P, M, SH, G, F, M2-1 (alternatively, M2(ORF1)), M2-2 (alternatively, M2(ORF2)), and L. Thus, the term "gene" interchangeably refers to a genomic RNA sequence that encodes a subgenomic RNA, and to a ORF (the latter term applies particularly in a situation such as in the case of the RSV M2 gene, where a single mRNA contains two overlapping ORFs that encode distinct proteins). Collins et al., *J. Gen. Virol.* 71:3015–3020, 1990; Bermingham and Collins, *Proc. Natl. Acad. Sci. USA* 96:11259–11264, 1999; Ahmadian et al., *EMBO J.* 19:2681–2689, 2000; Jin et al., *J. Virol.* 74:74–82, 2000 (each incorporated herein by reference). When the term "gene" is used in the context of determining gene position relative to a promoter position, the term ordinarily refers strictly to an mRNA-encoding sequence bordered by transcription gene-start and gene-end signal motifs (Collins et al., *Proc. Natl. Acad. Sci. USA* 83:4594–4598, 1986; Kuo et al., *J. Virol.* 70:6892–6901, 1996; each incorporated herein by reference).

By "genome segment" is meant any length of continuous nucleotides from the RSV genome, which may be part of an ORF, a gene, or an extragenic region, or a combination thereof.

Four of the RSV proteins presently identified are nucleocapsid/polymerase proteins, namely the major nucleocapsid N protein, the phosphoprotein P, and polymerase protein L, and the transcription antitermination protein M2-1 encoded by a first open reading frame (ORF) in the M2 gene. Three of these proteins are surface glycoproteins, namely the attachment G protein, the fusion F glycoprotein responsible for penetration and syncytium formation, and the small hydrophobic SH protein of unknown function. The matrix M protein is an internal virion protein involved in virion formation. There are two nonstructural proteins NS1 and NS2 of unknown function. Finally, there is a second open reading frame (ORF) in the M2 mRNA which encodes an RNA regulatory factor M2-2.

The G and F proteins are the major neutralization and protective antigens (Collins, et al., *Fields Virology* 2:1313–1352, 1996; Connors, et al., *J. Virol.* 66:1277–81, 1992). Resistance to reinfection by RSV is largely mediated by serum and mucosal antibodies specific against these proteins. RSV-specific cytotoxic T cells are also induced by RSV infection and can be directed against a number of different proteins, but this effector has not yet been shown to be an important contributor to long term resistance to reinfection. However, both CD8+ and CD4+ cells can be important in regulating the immune response, and both may be involved in viral pathogenesis (Johnson, et al., *J. Virol.* 72:2871–80, 1998; Srikiatkhachom and Braciale, *J. Exp. Med.* 186:421–32, 1997). Thus, F and G are the most important antigenic determinants, but other proteins can also play important roles in the immune response.

The M2 ORF2 mRNA encodes an RNA regulatory factor M2-2. The M2-2 mRNA, not found in other paramyxoviruses or rhabdoviruses, contains two overlapping translational open reading frames (ORFs) which each express a protein (FIG. 1A) (Collins et al., *J. Gen. Virol.* 71:3015–20, 1990, incorporated herein by reference). The upstream ORF1 encodes the 194-amino acid M2-1 protein, which is a structural component of the virion (Peeples et al., *Virology* 95:137–45, 1979, incorporated herein by reference) and is an anti-termination factor that promotes transcriptional chain elongation and also increases the frequency of read through at gene junctions (Collins et al., *Proc. Nat. Acad. Sci. USA* 93:81–5, 1996; Feams and Collins, *J. Virol.* 73:5852–5864, 1999; Collins et al. *Virology* 259:251–255, 1999; Hardy et al., *J. Virol.* 72:520–6, 1998, each incorporated herein by reference). ORF2 of strain A2 has 3 potential start site at codons 1, 3 and 7, all of which overlap with ORF1 (FIG. 1A). Initiation at the first of these would give an M2-2 protein of 90 amino acids. M2 ORF2 is present in all pneumoviruses examined to date (Collins et al., *J. Gen. Virol.* 71:3015–20, 1990; Ling et al., *J. Gen. Virol.* 73:1709–15, 1992; Zamora et al., *J. Gen. Virol.* 73:737–41, 1992, each incorporated herein by reference). Translation of M2 mRNA in a cell-free system yielded the M2-1 protein and a second, 11 kDa protein which was of the appropriate size to be the M2-2 protein (Collins et al., *J. Gen. Virol.* 71:3015–20, 1990). Coexpression of M2-2 in a model minireplicon system was found to have a very potent down-regulatory effect on RNA synthesis (Collins et al., *Proc. Nat. Acad. Sci. USA* 93:81–5, 1996; Hardy et al., *J. Virol.* 72:520–6, 1998). More recently, the RSV M2-2 protein was detected as a minor species in RSV-infected cells. Thus, several lines of evidence indicate that the M2-2 ORF is an eleventh RSV gene. However, definitive evidence that an ORF encodes a significant viral protein includes identification of a biological effect mediated by expression of the ORF in an infectious virus. This is demonstrated for M2-2 according to the methods of the present invention by ablating or deleting all or part of the M2-2 ORF and thereafter identifying phenotypic changes—including a shift in the balance of RNA transcription and replication. Although previous studies suggested that the M2-2 protein generally down-regulates transcription and RNA replication, the instant disclosure demonstrates that M2-2 unexpectedly shifts the balance of RNA synthesis from transcription to replication.

Expression of M2 ORF2 is preferably reduced or ablated by modifying the recombinant RSV genome or antigenome to incorporate a frame shift mutation or one or more stop codons in M2 ORF2. In more detailed aspects of the invention, M2 ORF2 is subjected to mutagenesis to generate a specific frame-shift mutation, hereafter called the NdeI mutation (FIG. 1B). The restriction enzyme site within ORF2 for the NdeI mutation was identified at genome position 8299, and the frame-shift mutation (2 nts added) was at codon 47 of the predicted 90 amino acid protein (FIG. 1B). Accordingly, the NdeI mutant (exemplified by recombinant strain rA2-NdeI) encodes the N-terminal 46 amino acids of M2-2 fused to 18 heterologous amino acids encoded by the frame-shift. Optional frame shift mutations to generate M2 ORF2 knock out mutants are readily identified.

In other more detailed aspects of the invention, a second exemplary M2-2 knock-out mutation is described below, the K5 mutation, which ablates expression of M2 ORF2 by altering three potential initiation codons within M2 ORF2 (FIGS. 1A and 1C) to ACG stop codons. A stop codon may also be added in each register following the ORF1 termination codon, terminating M2 ORF2 at codon 13 (FIG. 1C) to minimize the possibility of reversion or non-AUG initiation. An exemplary M2 ORF2 knock out mutant in this context is the recombinant strain rA2-K5 (also referred to as rA2ΔM2-2), described below. Other alterations to achieve disruption of M2 ORF2 expression or M2-2 protein expression or function to generate attenuated RSV vaccine candidates include partial or complete deletion of the M2 ORF2 coding sequence, in whole or in part, to render the M2-2 protein partially or entirely non-functional or terminate its expression. Yet another method for changing the level of expression of M2-ORF2 is to alter its translational start site or its spacing relative to the upstream ORF1. For example, M2-ORF2 can be expressed as a separate gene at any locus in the genome or antigenome, e.g., by insertion of the M2-ORF2 with its own gene start and gene end signals into an intergenic or other non-coding region of the genome or antigenome.

As noted above, the recombinant RSV of the invention bearing one or more mutations in M2 ORF2 possess highly desirable phenotypic characteristics for vaccine development (see also, Bermingham et al., Proc. Natl. Acad. Sci. USA 96:11259–11264, 1999; and Jin et al., J. Virol. 74:74–82, 2000, each incorporated herein by reference). The modifications described herein that delete M2 ORF2, in whole or in part, or reduce or ablate expression of M2 ORF2 specify a range of desired phenotypic changes in the resulting virus or subviral particle. In preferred embodiments, M2 ORF2 deletion and knock out mutants exhibit attenuated viral growth compared to growth of a corresponding wild-type or mutant parental RSV strain. Growth, for example in cell cultures, may be reduced by about two-fold, more often about 5-fold, and preferably about 10-fold or greater overall (e.g., as measured after a 7–8 day period in culture) compared to growth of the corresponding wild-type or mutant parental RSV strain. In more detailed aspects, recombinant RSV of the invention exhibit delayed kinetics of viral growth, wherein growth during an initial 2–5 day period is reduced by about 100-fold and up to 1,000-fold or more compared to kinetics of growth in the corresponding wild-type or mutant parental RSV strain. These desirable effects are specified by reduction or ablation of M2-2 ORF2 expression. Intermediate effects are achieved by reduction of M2-2 protein synthesis. Furthermore, as M2-2 is a regulatory protein, alterations in virus growth and the pattern of gene expression can also be achieved by increasing rather than decreasing M2-ORF2 expression. As described above, this can be readily achieved by expressing M2-ORF2 as a separate gene and, if necessary, moving the gene to a more promoter-proximal or promoter-distal location.

Recombinant vaccine viruses bearing M2 ORF2 deletion and knock out mutations also preferably exhibit a change in mRNA transcription. One aspect of this change is delayed kinetics of viral mRNA synthesis compared to kinetics of mRNA synthesis of a corresponding wild-type or mutant parental RSV strain. However, after time (e.g., at 24 hours post-infection) the M2 ORF2 deletion and knock out mutants exhibit an increase in cumulative mRNA synthesis. This increase of cumulative mRNA synthesis can be achieved to levels of about 50–100%, 100–200%, 200–300% or greater compared to mRNA accumulation in the corresponding wild-type or mutant parental RSV strain.

Also provided within the invention are M2 ORF2 deletion and knock out mutants which exhibit a reduction in viral RNA replication compared to viral RNA replication (synthesis of genome/antigenome) of the corresponding wild-type or mutant parental RSV strain. Thus, accumulation of genomic RNA (e.g., after a post-infection period of 24 hours) is about 25–30%, 15–25%, 10–15% or lower compared to genomic RNA accumulation in the corresponding wild-type or mutant parental RSV strain.

In preferred M2 ORF2 deletion and knock out mutants of the invention, both of the foregoing changes in mRNA and genomic RNA synthesis are observed. Thus, a cumulative molar ratio of mRNA to genomic RNA is increased 2- to 5-fold, 5-to 10-fold, 10- to 20-fold or greater compared to a cumulative molar ratio of mRNA to genomic RNA observed for the corresponding wild-type or mutant parental RSV strain.

Also provided herein are M2 ORF2 deletion and knock out mutants exhibiting increased viral protein accumulation in infected cells compared to viral protein accumulation in cells infected with a corresponding wild-type or mutant parental RSV strain. Increased viral protein levels (e.g., at 36 hours post-infection) may be 50–100%, 100–200%, 200–300% or greater. This is particularly desirable in M2 ORF2 deletion and knock out mutants which exhibit wherein the phenotypic change comprises increased expression of one or more viral antigens compared to expression of the antigen(s) in the corresponding wild-type or mutant parental RSV strain. This is a particularly desirable phenotype considering that other attenuating mutations for RSV typically result in reduced antigen expression and immunogenicity.

In summary, preferred M2 ORF2 deletion and knock out mutants are engineered to express undiminished or increased levels of selected viral antigens while also exhibiting an attenuated phenotype. These recombinants thus maintain immunogenic potential due to the increased mRNA transcription and antigen expression, while attenuation is maintained through concomitant reductions in replication and growth. This surprising assemblage of phenotypic traits is highly desired for vaccine development because the vaccine candidates can be suitably attenuated without sacrificing immunogenic potential, and may indeed exhibit increased immunogenic activity.

The instant invention provides for development of live-attenuated RSV vaccine candidates incorporating M2 ORF2 deletion or knock out mutations. These recombinant viruses are constructed through a cDNA intermediate and cDNA-based recovery system. Recombinant viruses which are made from cDNA replicate independently and are propagated in the same manner as if they were biologically-derived. M2 ORF2 deletion and knock out mutants can be further modified to incorporate specific attenuating mutations, as well as a variety of other mutations and nucleotide modifications, to yield desired structural or phenotypic affects.

Detailed descriptions of the materials and methods for producing recombinant RSV from cDNA, and for making and testing the full range of mutations and nucleotide modifications disclosed herein as supplemental aspects of the present invention, are set forth in, e.g., U.S. Provisional Patent Application No. 60/007,083, filed Sep. 27, 1995; U.S. Patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. Pat. No. 5,993,824, issued Nov. 30, 1999 (corresponding to International Publication No. WO 98/02530); U.S. patent application Ser. No. 09/291,894, filed by Collins et al. on Apr. 13, 1999; U.S. Provisional Patent Application No. 60/129,006, filed by Murphy et al. on Apr. 13, 1999; Crowe et al., *Vaccine* 12: 691–699, 1994; and Crowe et al., *Vaccine* 12: 783–790, 1994; Collins, et al., *Proc Nat. Acad. Sci. USA* 92:11563–11567, 1995; Bukreyev, et al., *J Virol* 70:6634–41, 1996, Juhasz et al., *J. Virol.* 71(8):5814–5819, 1997; Durbin et al., *Virology* 235:323–332, 1997; Karron et al., *J. Infect. Dis.* 176:1428–1436, 1997); He et al. *Virology* 237:249–260, 1997; Baron et al. *J. Virol.* 71:1265–1271, 1997; Whitehead et al., *Virology* 247(2):232–9, 1998a; Whitehead et al., *J. Virol.* 72(5):4467–4471, 1998b; Jin et al. *Virology* 251:206–214, 1998; Bukreyev, et al., *Proc. Nat. Acad. Sci. USA* 96:2367–2372, 1999; Bermingham and Collins, *Proc. Natl. Acad. Sci. USA* 96:11259–11264, 1999 Juhasz et al., *Vaccine* 17:1416–1424, 1999; Juhasz et al., *J. Virol.* 73:5176–5180, 1999; Teng and Collins, *J. Virol.* 73:466–473, 1999; Whitehead et al., *J. Virol.* 73:9773–9780, 1999; Whitehead et al., *J. Virol.* 73:871–877, 1999; and Whitehead et al., *J. Virol.* 73:3438–3442, 1999. Exemplary methods for producing recombinant RSV from cDNA involve intracellular coexpression, typically from plasmids cotransfected into tissue culture cells, of an RSV antigenomic RNA and the RSV N, P, M2-1 and L proteins. This launches a productive infection that results in the production of infectious cDNA-derived virus, which is termed recombinant virus. Once generated, recombinant RSV is readily propagated in the same manner as biologically-derived virus, and a recombinant virus and a counterpart biologically-derived virus cannot be distinguished unless the former had been modified to contain one or more introduced changes as markers.

The ability to generate infectious RSV from cDNA provides a method for introducing predetermined changes into infectious virus via the cDNA intermediate. This method has been demonstrated to produce a wide range of infectious, attenuated derivatives of RSV, for example recombinant vaccine candidates containing one or more amino acid substitutions in a viral protein, deletion of one or more genes or ablation of gene expression, and/or one or more nucleotide substitutions in cis-acting RNA signals yielding desired effects on viral phenotype (see, e.g., Bukreyev et al., *J. Virol.* 71:8973–8982, 1997; Whitehead et al., *J. Virol.* 72:4467–4471, 1998; Whitehead et al., *Virology,* 247:232–39, 1998; Bermingham and Collins, *Proc. Natl. Acad. Sci. USA* 96:11259–11264,1999; Juhasz et al., *Vaccine* 17:1416–1424, 1999; Juhasz et al., *J. Virol.* 73:5176–5180, 1999; Teng and Collins, *J. Virol.* 73:466–473, 1999; Whitehead et al., *J. Virol.* 73:871–877, 1999; Whitehead et al., *J. Virol.* 73:3438–3442, 1999; and Collins et al., *Adv. Virus Res.* 54:423–451, 1999, each incorporated herein by reference).

Exemplary of the foregoing teachings are methods and procedures useful within the invention for mutagenizing, isolating and characterizing RSV to obtain attenuated mutant strains (e.g., temperature sensitive (ts), cold passaged (cp) cold-adapted (ca), small plaque (sp) and host-range restricted (hr) mutant strains) and for identifying the genetic changes that specify the attenuated phenotype. In conjunction with these methods, the foregoing documents detail procedures for determining replication, immunogenicity, genetic stability and protective efficacy of biologically derived and recombinantly produced attenuated human RSV, including human RSV A and B subgroups, in accepted model systems, including murine and non-human primate model systems. In addition, these documents describe general methods for developing and testing immunogenic compositions, including monovalent and bivalent vaccines, for prophylaxis and treatment of RSV infection.

Methods for producing infectious recombinant RSV by construction and expression of cDNA encoding an RSV genome or antigenome coexpressed with essential RSV proteins are also described in the above-incorporated documents (see, e.g., U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. patent application Ser. No. 08/892, 403, filed Jul. 15, 1997 (corresponding to International Publication No. WO 98/02530)).

Also disclosed are methods for constructing and evaluating infectious recombinant RSV that are modified to incorporate phenotype-specific mutations identified in biologically-derived RSV mutants, e.g., cp and ts mutations adopted in recombinant RSV from biologically derived RSV mutants designated cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579). The recombinant RSV thus provided may incorporate one, two, or more ts mutations from the same, or different, biologically derived RSV mutant(s), for example one or more of the 248/404, 248/955, 530/1009, or 530/1030 biological mutants. In the latter context, multiply attenuated recombinants may have a combination of attenuating mutations from two, three or more biological mutants, e.g., a combination of attenuating mutations from the RSV mutants 530/1009/404, 248/404/1009, 248/404/1030, or 248/404/1009/1030 mutants. In exemplary embodiments, one or more attenuating mutations specify a temperature-sensitive substitution at amino acid Asn43, Phe521, Gln831, Met1169, or Tyr1321 in the RSV polymerase gene or a temperature-sensitive nucleotide substitution in the gene-start sequence of gene M2. Preferably, these mutations involve identical or conservative changes with the following changes identified in biologically derived mutant RSV; Ile for Asn43, Leu for Phe521, Leu for Gln831, Val for Met1169, and Asn for Tyr1321.

In one recent exemplary embodiment of the invention, the sequence of RSV mutant cpts248/955 was determined, with the exception of the first 29 nucleotides (3'-end of the genome) and the last 33 nucleotides (5'-end) of the genome. The sequence was then compared to that of parental virus cpts248. Mutant virus cpts248/955 contained all the mutations previously identified in cspts248, as well as the following mutations: 1. Insertion of an A residue in the P gene-end signal at nucleotide 3236. This increases the poly-A tract from 7 A's to 8 A's. The is the same insertion observed previously in recombinant RSV rA2 virus preparations, which did not effect replication levels in mice. 2. An Asn to Ile mutation of amino acid 43 of the L polymerase due to A to U mutation at cpRSV nucleotide (nt) 8626. It is therefore considered that the cpts248/955 phenotype is attributed to the missense mutation at nt 8626. This is consistent with previous findings for the RSV 530, 1030, 1009, and 248 mutants.

Yet additional mutations that may be incorporated in M2 ORF2 deletion and knock out RSV mutants of the invention are mutations, e.g., attenuating mutations, identified in heterologous RSV or more distantly related negative stranded RNA viruses. In particular, attenuating and other desired mutations identified in one negative stranded RNA virus may be "transferred", e.g., copied, to a corresponding position within the genome or antigenome of the M2 ORF2 deletion and knock out mutants. Briefly, desired mutations in one heterologous negative stranded RNA virus are transferred to the RSV recipient (e.g., bovine or human RSV, respectively). This involves mapping the mutation in the heterologous virus, thus identifying by sequence alignment the corresponding site in the recipient RSV, and mutating the native sequence in the RSV recipient to the mutant genotype (either by an identical or conservative mutation), as described in International Application No. PCT/US00/09695 filed Apr. 12, 2000 and corresponding priority U.S. Provisional Patent Application Serial No. 60/129,006, each incorporated herein by reference. As this disclosure teaches, it is preferable to modify the recipient genome or antigenome to encode an alteration at the subject site of mutation that corresponds conservatively to the alteration identified in the heterologous mutant virus. For example, if an amino acid substitution marks a site of mutation in the mutant virus compared to the corresponding wild-type sequence, then a similar substitution should be engineered at the corresponding residue(s) in the recombinant virus. Preferably the substitution will involve an identical or conservative amino acid to the substitute residue present in the mutant viral protein. However, it is also possible to alter the native amino acid residue at the site of mutation non-conservatively with respect to the substitute residue in the mutant protein (e.g., by using any other amino acid to disrupt or impair the function of the wild-type residue). Negative stranded RNA viruses from which exemplary mutations are identified and transferred into a recombinant RSV of the invention include other RSVs (e.g., murine), PIV, Sendai virus (SeV), Newcastle disease virus (NDV), simian virus 5 (SV5), measles virus (MeV), rindepest virus, canine distemper virus (CDV), rabies virus (RaV) and vesicular stomatitis virus (VSV). A variety of exemplary mutations are disclosed, including but not limited to an amino acid substitution of phenylalanine at position 521 of the RSV L protein (corresponding to a substitution of phenylalanine at position 456 of the HPIV3 L protein). In the case of mutations marked by deletions or insertions, these can be introduced as corresponding deletions or insertions into the recombinant virus, however the particular size and amino acid sequence of the deleted or inserted protein fragment can vary.

A variety of additional types of mutations are also disclosed in the foregoing incorporated references and can be readily engineered into a recombinant RSV of the invention to calibrate attenuation, immunogenicity or provide other advantageous structural and/or phenotypic effects. For example, restriction site markers are routinely introduced within the M2 ORF2 deletion or knock out mutant antigenome or genome to facilitate cDNA construction and manipulation. Also described in the incorporated references are a wide range of nucleotide modifications other than point or site-specific mutations that are useful within the instant invention. For example, methods and compositions are disclosed for producing recombinant RSV expressing an additional foreign gene, e.g., a chloramphenicol acetyl transferase (CAT) or luciferase gene. Such recombinants generally exhibit reduced growth associated with the inserted gene. This attenuation appears to increase with increasing length of the inserted gene. The finding that insertion of a foreign gene into recombinant RSV reduces level of replication and is stable during passage in vitro provides another effective method for attenuating RSV for vaccine use. Similar or improved effects can thus be achieved by insertion of other desired genes, for example cytokines such as interferon-γ, interleukin-2, interleukin-4 and GM-CSF, among others.

Additional nucleotide modifications disclosed in the foregoing references for incorporation into M2 ORF2 deletion and knock out RSV of the invention include partial or complete deletion or ablation of a different RSV gene outside of M2 ORF2. Thus, additional RSV genes or genome segments within recombinant RSV of the invention may be deleted, including partial or complete deletions of open reading frames and/or cis-acting regulatory sequences of the RSV NS1, NS2, N, P, M, G, F, SH, M2(ORF1), and/or L genes. Within this aspect of the invention nucleotide modifications may be engineered to delete or silence a selected gene to achieve a recombinant vaccine candidate that replicates well in vitro but which is attenuated for replication in vivo (Bukreyev et al., *J. Virol.* 71:8973–8982, 1997; 23] Teng et al., *J. Virol.* 73:466–473, 1999; each incorporated herein by reference). For example, deletion of the SH gene results in a virus, exemplified by rA2ΔSH, that replicates in vitro with an efficiency equal to or slightly better than that of wild-type rRSV (rA2) and which is moderately attenuated in mice and chimpanzees (Bukreyev et al., *J. Virol.* 71:8973–8982, 1997; Whitehead et al., *J. Virol.* 73:3438–3442, 1999; each incorporated herein by reference). Recombinant RSV from which the NS2 gene is deleted, designated rA2ΔNS2, exhibits reduced growth kinetics and reduced yield of infectious virus in vitro and is markedly attenuated in mice and chimpanzees (Teng et al., *J. Virol.* 73:466–473, 1999; Whitehead et al., *J. Virol.* 73:3438–3442, 1999; each incorporated herein by reference). Similar in vitro properties are disclosed for a recombinant bovine RSV from which the NS2 gene is deleted (Buchholz et al., *J. Virol.* 73:251–259, 1999; incorporated herein by reference).

In one example, a recombinant RSV was generated in which expression of the SH gene was ablated by removal of a polynucleotide sequence encoding the SH mRNA and protein. Deletion of the SH gene yielded not only recoverable, infectious RSV, but one which exhibited substantially improved growth in tissue culture based on both yield of infectious virus and plaque size. This improved growth in tissue culture specified by the SH deletion provides useful tools for developing M2 ORF2 deletion and knock out mutant RSV vaccines, for example by overcoming problems of poor RSV yields in culture. Moreover, these deletions are highly stable against genetic reversion, rendering RSV clones derived therefrom particularly useful as vaccine agents.

SH-minus RSV recombinants also exhibit site-specific attenuation in the upper respiratory tract of mice, which presents novel advantages for vaccine development. Certain of the current RSV strains under evaluation as live virus vaccines, for example cp mutants, do not exhibit significantly altered growth in tissue culture. These are host range mutations and they restrict replication in the respiratory tract of chimpanzees and humans approximately 100-fold in the lower respiratory tract. Another exemplary type of mutation, ts mutations, tend to preferentially restrict virus replication in the lower respiratory tract due to the gradient of increasing body temperature from the upper to the lower respiratory tract. In contrast to these cp and ts mutants, SH-minus RSV mutants have distinct phenotypes of greater restriction in the upper respiratory tract. This is particularly desirable for vaccine viruses for use in very young infants, because restriction of replication in the upper respiratory tract is required to ensure safe vaccine administration in this vulnerable age group whose members breathe predominantly through the nose. Further, in any age group, reduced replication in the upper respiratory tract will reduce morbidity from otitis media. In addition to these advantages, the nature of SH deletion mutations, involving e.g., nearly 400 nt and ablation of an entire mRNA, represents a type of mutation which will be highly refractory to reversion.

Also discussed in the context of SH gene modifications is a comparison of SH genes among different RSVs, including human and bovine RSVs, and other pneumoviruses to provide additional tools and methods for generating useful RSV recombinant vaccines. For example, the two RSV antigenic subgroups, A and B, exhibit a relatively high degree of conservation in certain SH domains. In two such domains, the N-terminal region and putative membrane-spanning domains of RSV A and B display 84% identity at the amino acid level, while the C-terminal putative ectodomains are more divergent (approx. 50% identity). Comparison of the SH genes of two human RSV subgroup B strains, 8/60 and 18537, identified only a single amino acid difference (Anderson et al., supra). The SH proteins of human versus bovine RSV are approximately 40% identical, and share major structural features including (i) an asymmetric distribution of conserved residues; (ii) very similar hydrophobicity profiles; (iii) the presence of two N-linked glycosylation sites with one site being on each side of the hydrophobic region; and (iv) a single cysteine residue on the carboxy-terminal side of the central hydrophobic region of each SH protein. (Anderson et al., supra). By evaluating these and other sequence similarities and differences, selections can be made of heterologous sequence(s) that can be substituted or inserted within infectious M2 ORF2 deletion and knock out mutant RSV clones, for example to yield vaccines having multi-specific immunogenic effects or, alternatively or in addition, desirable effects such as attenuation.

Also disclosed in the context of gene deletions are the effects of changing gene position. For example, deletion of the SH gene results in an effective change in downstream gene position to a more promoter proximal position. This may be associated with an increase in transcription of downstream genes in the recombinant virus. Alternatively, the position of any gene can be changed to alter expression, for example by insertion or transpostioning of the gene to an upstream or downstream intergenic or other noncoding region. Thus, methods are provided for altering levels of RSV gene expression by changing gene order or position in the genome or antigenome. Decreased levels of expression of downstream genes are expected to specify attenuation phenotypes, whereas increased expression can achieve the opposite effects in recombinant RSV in permissive hosts, e.g., chimpanzees and humans.

In another example described in the above-incorporated references, expression of the NS2. gene is ablated by introduction of stop codons into the translational open reading frame (ORF). The rate of release of infectious virus was reduced for this NS2 knock-out virus compared to wild-type. In addition, comparison of the plaques of the mutant and wild-type viruses showed that those of the NS2 knockout were greatly reduced in size. This type of mutation can thus be incorporated within viable recombinant RSV to yield altered phenotypes, in this case reduced rate of virus growth and reduced plaque size in vitro. These and other knock-out methods and mutants will therefore provide for yet additional recombinant RSV vaccine agents, based on the correlation between reduced plaque size in vitro and attenuation in vivo. Expression of the NS2 gene also was ablated by complete removal of the NS2 gene, yielding a virus with a similar phenotype.

Other RSV genes which have been successfully deleted include the NS1 and G genes. The former was deleted by removal of the polynucleotide sequence encoding the respective protein, and the latter by introducing a frame-shift or altering translational start sites and introducing stop codons. Specifically, the NS1 gene was deleted by removal of nucleotides 122 to 630 in the antigenomic cDNA, thereby joining the upstream nontranslated region of NS1 to the translational initiation codon of NS2. This virus, designated rA2ΔNS1, exhibited reduced RNA replication, plaque size, growth kinetics and approximately 10-fold lower yield of infectious virus in vitro. Interestingly, recovered NS1-minus virus produce small plaques in tissue culture albeit not as small as those of the NS2 deletion virus. The fact that the NS1-minus virus can grow, albeit with reduced efficiency, identifies the NS1 protein as an accessory protein, one that is dispensable to virus growth. The plaque size of the NS1-minus virus was similar to that of NS2 knock-out virus in which expression of the NS2 protein was ablated by introducing translational stop codons into its coding sequence. The small plaque phenotype is commonly associated with attenuating mutations. This type of mutation can thus be incorporated within viable recombinant RSV to yield altered phenotypes. These and other knock out methods and mutants will therefore provide for yet additional recombinant RSV vaccine agents, based on the known correlation between plaque size in vitro and attenuation in vivo. The NS2 knock-out mutant exhibited a moderately attenuated phenotype in the upper respiratory tract and a highly attenuated phenotype in the lower respiratory tract in naive chimpanzees. This mutant also elicited greatly reduced disease symptoms in chimps while stimulating significant resistance to challenge by the wild-type virus (Whitehead et al., *J. Virol.* 73:3438–3442, 1999, incorporated herein by reference).

Yet additional methods and compositions provided within the incorporated references and useful within the invention involve different nucleotide modifications within M2 ORF2 deletion and knock out mutants that alter different cis-acting regulatory sequences within the recombinant genome or antigenome. For example, a translational start site for a secreted form of the RSV G glycoprotein can be deleted to disrupt expression of this form of the G glycoprotein. The RSV G protein is synthesized in two forms: as an anchored type II integral membrane protein and as a N-terminally resected form which lacks essentially all of the membrane anchor and is secreted (Hendricks et al., *J. Virol.* 62:2228–2233, 1988). The two forms have been shown to be derived by translational initiation at two different start sites: the longer form initiates at the first AUG of the G ORF, and the second initiates at the second AUG of the ORF at codon 48 and is further processed by proteolysis (Roberts et al., *J. Virol.* 68: 4538–4546 1994). The presence of this second start site is highly conserved, being present in all strains of human, bovine and ovine RSV sequenced to date. It has been suggested that the soluble form of the G protein might mitigate host immunity by acting as a decoy to trap neutralizing antibodies. Also, soluble G has been implicated in preferential stimulation of a Th2-biased response, which in turn appears to be associated with enhanced immunopathology upon subsequent exposure to RSV. With regard to an RSV vaccine virus, it is highly desirable to minimize antibody trapping or imbalanced stimulation of the immune system, and so it would be desirable to ablate expression of the secreted form of the G protein. This has been achieved in recombinant virus. Thus, this mutation is particularly useful to qualitatively and/or quantitatively alter the host immune response elicited by the recombinant virus, rather than to directly attenuate the virus. Also the G protein gene may be deleted altogether. The resulting virus exhibits a host range effect, growing inefficiently on HEp-2 cells but growing as efficiently as wild type virus on Vero cells. Presumably, attachment function can also be provided by another protein or can be dispensed with altogether. Thus, the invention also provides live-attenuated RSV vaccine virus lacking the G protein.

The incorporated references also describe modulation of the phenotype of recombinant RSV by altering cis-acting transcription signals of exemplary genes, e.g., NS1 and NS2. The results of these nucleotide modifications are consistent with modification of gene expression by altering cis-regulatory elements, for example to decrease levels of read through mRNAs and increase expression of proteins from downstream genes. The resulting recombinant viruses will preferably exhibit increased growth kinetics and increased plaque size. Exemplary modifications to cis-acting regulatory sequences include modifications to gene end (GE) and gene start (GS) signals associated with RSV genes. In this context, exemplary changes include alterations of the GE signals of the NS1 and NS2 genes rendering these signals identical to the naturally-occurring GE signal of the RSV N gene. The resulting recombinant virus exhibits increased growth kinetics and plaque size and therefore provide yet additional means for beneficially modifying phenotypes of M2 ORF2 deletion and knock out mutant RSV vaccine candidates.

Also useful within the instant invention are methods and compositions provided in the above-incorporated references that allow production of attenuated M2 ORF2 deletion and knock out mutant RSV vaccine virus comprising sequences from both RSV subgroups A and B, e.g., to yield a RSV A or B vaccine or a bivalent RSV A/B vaccine. Thus, methods and compositions provided in the above-incorporated references that allow production of attenuated M2 ORF2 deletion and knock out RSV vaccine viruses comprising sequences from both RSV subgroups A and B, e.g., to yield a RSV A or B vaccine or a bivalent RSV A/B vaccine (see, e.g., U.S. patent application Ser. No. 09/291,894, filed by Collins et al. on Apr. 13, 1999, incorporated herein by reference). In one example a RSV subgroup B-specific vaccine virus is provided in which an attenuated subgroup A virus is used to express the F and/or G glycoproteins of a subgroup B RSV. Because the F and G proteins are the major protective antigens and confer most of the RSV subgroup specificity, this chimeric virus will stimulate a strong immune response against subgroup B. This strategy may be implemented using two alternative approaches. One is to insert the G glycoprotein gene of a subgroup B virus into the subgroup A background (or vice-versa) as an additional gene. However, since the F protein also exhibits significant subgroup-specificity, it would be preferable to express both subgroup B glycoproteins in a subgroup B-specific vaccine. Moreover, it is desirable to further modify a subgroup B virus to achieve proper attenuation and immunogenicity in accordance with the teachings herein. Thus, the second, more desirable strategy to achieve an RSV subgroup B vaccine is to remove the G and F genes from a subgroup A recombinant cDNA background genome or antigenome, and replace them with the G and F genes of a subgroup B RSV. The resulting A/B chimeric RSV contains the internal proteins of subgroup A and the external protective antigens of subgroup B. This virus can then be attenuated to a desired level by systematic incorporation of attenuating mutations as described above. For example, specific attenuating mutations that have been incorporated into chimeric RSV A/B viruses include: (i) three of the five cp mutations, namely the mutation in N (V267I) and the two in L (C319Y and H1690Y), but not the two in F since these are removed by substitution with the B1 F gene; (ii) the 248 (Q831L), 1030 (Y1321N) and, optionally, 404-L (D1183E) mutations which have been identified in attenuated strain A2 viruses; (iii) the single nucleotide substitution at position 9 in the gene-start signal of the M2 gene, and (iv) deletion of the SH gene. Other immediately available mutations in chimeric RSV A/B include, but are not limited to, NS1, NS2, SH, or G gene deletions, and the 530 and 1009 mutations, alone or in combination.

Desired phenotypic changes that are engineered into M2 ORF2 deletion and knock out mutant RSV of the invention include, but are not limited to, attenuation in cell culture or in a selected host environment, resistance to reversion from the attenuated phenotype, enhanced immunogenic characteristics (e.g., as determined by enhancement, or diminution, of an elicited immune response), upregulation or downregulation of transcription and/or translation of selected viral products, etc. In preferred aspects of the invention, attenuated, M2 ORF2 deletion and knock out mutant RSV are produced in which the recombinant genome or antigenome is further modified by introducing one or more attenuating mutations specifying an attenuating phenotype. These mutations may be generated de novo and tested for attenuating effects according to a rational design mutagenesis strategy as described in the above-incorporated references. Alternatively, the attenuating mutations can be identified in a biologically derived mutant RSV and thereafter incorporated into the M2 ORF2 deletion and knock out mutant RSV of the invention.

Attenuating mutations in biologically derived RSV for incorporation within an M2 ORF2 deletion or knock out mutant RSV vaccine strain may occur naturally or may be introduced into wild-type RSV strains by well known mutagenesis procedures. For example, incompletely attenuated parental RSV strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) or exhibit temperature sensitive (ts) phenotypes in cell culture, as generally described herein and in U.S. Pat. No. 5,922,326, incorporated herein by reference.

By "biologically derived RSV" is meant any RSV not produced by recombinant means. Thus, biologically derived RSV include naturally occurring RSV of all subgroups and strains, including, e.g., naturally occurring RSV having a wild-type genomic sequence and RSV having genomic variations from a reference wild-type RSV sequence, e.g., RSV having a mutation specifying an attenuated phenotype. Likewise, biologically derived RSV include RSV mutants derived from a parental RSV strain by, inter alia, artificial mutagenesis and selection procedures (see, e.g., International Publication WO 93/21310, incorporated herein by reference).

The level of temperature sensitivity of replication in exemplary attenuated RSV for use within the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of RSV correlate with the mutant's shutoff temperature. Replication of mutants with a shutoff temperature of 39° C. is moderately restricted, whereas mutants with a shutoff of 38° C. replicate less well and symptoms of illness are mainly restricted to the upper respiratory tract. A virus with a shutoff temperature of 35° C. to 37° C. will typically be fully attenuated in chimpanzees and substantially attenuated in humans. Thus, attenuated biologically derived mutant and M2 ORF2 deletion and knock out mutant RSV of the invention which are ts will have a shutoff temperature in the range of about 35° C. to 39° C., and preferably from 35° C. to 38° C. The addition of a ts mutation into a partially attenuated strain produces a multiply attenuated virus useful within vaccine compositions of the invention.

A number of attenuated RSV strains as candidate vaccines for intranasal administration have been developed using multiple rounds of chemical mutagenesis to introduce multiple mutations into a virus which had already been attenuated during cold-passage (e.g., Connors et al., *Virology* 208: 478–484, 1995; Crowe et al., *Vaccine* 12: 691–699, 1994; and Crowe et al., *Vaccine* 12: 783–790, 1994, incorporated herein by reference). Evaluation in rodents, chimpanzees, adults and infants indicate that certain of these candidate vaccine strains are relatively stable genetically, are highly immunogenic, and may be satisfactorily attenuated. Nucleotide sequence analysis of some of these attenuated viruses indicates that each level of increased attenuation is associated with specific nucleotide and amino acid substitutions. The above-incorporated references also disclose how to routinely distinguish between silent incidental mutations and those responsible for phenotype differences by introducing the mutations, separately and in various combinations, into the genome or antigenome of infectious RSV clones. This process coupled with evaluation of phenotype characteristics of parental and derivative virus identifies mutations responsible for such desired characteristics as attenuation, temperature sensitivity, cold-adaptation, small plaque size, host range restriction, etc.

Mutations thus identified are compiled into a "menu" and are then introduced as desired, singly or in combination, to adjust an M2 ORF2 deletion or knock out mutant RSV vaccine virus to an appropriate level of attenuation, immunogenicity, genetic resistance to reversion from an attenuated phenotype, etc., as desired. Preferably, the chimeric RSV of the invention are attenuated by incorporation of at least one, and more preferably two or more, attenuating mutations identified from such a menu, which may be defined as a group of known mutations within a panel of biologically derived mutant RSV strains. Preferred panels of mutant RSV strains described herein are cold passaged (cp) and/or temperature sensitive (ts) mutants, for example a panel comprised of RSV mutants designated cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579) (each deposited under the terms of the Budapest Treaty with the American Type Culture Collection (ATCC) of 10801 University Boulevard, Manassas, Va. 20110-2209, U.S.A., and granted the above identified accession numbers).

From this exemplary panel of biologically derived mutants, a large menu of attenuating mutations are provided which can each be combined with any other mutation(s) within the panel for calibrating the level of attenuation in a recombinant, M2 ORF2 deletion or knock out mutant RSV for vaccine use. Additional mutations may be derived from RSV having non-ts and non-cp attenuating mutations as identified, e.g., in small plaque (sp), cold-adapted (ca) or host-range restricted (hr) mutant strains. Attenuating mutations may be selected in coding portions of a donor or recipient RSV gene or in non-coding regions such as a cis-regulatory sequence. For example, attenuating mutations may include single or multiple base changes in a gene start sequence, as exemplified by a single or multiple base substitution in the M2 gene start sequence at nucleotide 7605.

M2 ORF2 deletion and knock out mutants RSV designed and selected for vaccine use often have at least two and sometimes three or more attenuating mutations to achieve a satisfactory level of attenuation for broad clinical use. In one embodiment, at least one attenuating mutation occurs in the RSV polymerase gene and involves a nucleotide substitution specifying an amino acid change in the polymerase protein specifying a temperature-sensitive (ts) phenotype. Exemplary M2 ORF2 deletion and knock out mutants in this context incorporate one or more nucleotide substitutions in the large polymerase gene L resulting in an amino acid change at amino acid Asn43, Phe521, Gln831, Met1169, or Tyr1321, as exemplified by the changes, Ile for Asn43, Leu for Phe521, Leu for Gln831, Val for Met1169, and Asn for Tyr1321. Alternately or additionally, M2 ORF2 deletion and knock out mutant RSV of the invention may incorporate a ts mutation in a different RSV gene, e.g., in the M2 gene. Preferably, two or more nucleotide changes are incorporated in a codon specifying an attenuating mutation, e.g., in a codon specifying a ts mutation, thereby decreasing the likelihood of reversion from an attenuated phenotype.

In accordance with the methods of the invention, M2 ORF2 deletion and knock out mutant RSV can be readily constructed and characterized that incorporate at least one and up to a full complement of attenuating mutations present within a panel of biologically derived mutant RSV strains. Thus, mutations can be assembled in any combination from a selected panel of mutants, for example, cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579). In this manner, attenuation of vaccine candidates can be finely adjusted for use in one or fewer classes of patients, including seronegative infants.

In more specific embodiments, M2 ORF2 deletion and knock out mutant RSV for vaccine use incorporate at least one and up to a full complement of attenuating mutations specifying a temperature-sensitive and/or attenuating amino acid substitution at Asn43, Phe521, Gln831, Met1169 or Tyr1321 in the RSV polymerase gene L, or a temperature-sensitive nucleotide substitution in the gene-start sequence of gene M2. Alternatively or additionally, the recombinant RSV of the invention may incorporate at least one and up to a full complement of mutations from cold-passaged attenuated RSV, for example one or more mutations specifying an amino acid substitution at Val267 in the RSV N gene, Glu218 or Thr523 in the RSV F gene, Cys319 or His1690 in the RSV polymerase gene L.

In other detailed embodiments, the M2 ORF2 deletion and knock out mutant RSV of the invention is further modified to incorporate attenuating mutations selected from (i) a panel of mutations specifying temperature-sensitive amino acid substitutions Gln831 to Leu, and Tyr1321 to Asn in the RSV polymerase gene L; (ii) a temperature-sensitive nucleotide substitution in the gene-start sequence of gene M2; (iii) an attenuating panel of mutations adopted from cold-passaged RSV specifying amino acid substitutions Val267 Ile in the RSV N gene, and Cys319 to Tyr and His1690 Tyr in the RSV polymerase gene L; or (iv) deletion or ablation of expression of one or more of the RSV SH, NS1, NS2, G and M2-2 genes. Preferably, these and other examples of M2 ORF2 deletion and knock out mutant RSV incorporate at least two attenuating mutations adopted from biologically derived mutant RSV, which may be derived from the same or different biologically derived mutant RSV strains. Also preferably, these exemplary mutants have one or more of their attenuating mutations stabilized by multiple nucleotide changes in a codon specifying the mutation.

In accordance with the foregoing description, the ability to produce infectious RSV from cDNA permits introduction of specific engineered changes within M2 ORF2 deletion and knock out mutants. In particular, infectious, recombinant RSV are employed for identification of specific mutation(s) in biologically derived, attenuated RSV strains, for example mutations which specify ts, ca, att and other phenotypes. Desired mutations are thus identified and introduced into recombinant, M2 ORF2 deletion and knock out mutant RSV vaccine strains. The capability of producing virus from cDNA allows for routine incorporation of these mutations, individually or in various selected combinations, into a full-length cDNA clone, whereafter the phenotypes of rescued recombinant viruses containing the introduced mutations can be readily determined.

By identifying and incorporating specific, biologically derived mutations associated with desired phenotypes, e.g., a cp or ts phenotype, into infectious RSV clones, the invention provides for other, site-specific modifications at, or within close proximity to, the identified mutation. Whereas most attenuating mutations produced in biologically derived RSV are single nucleotide changes, other "site specific" mutations can also be incorporated by recombinant techniques into biologically derived or recombinant RSV. As used herein, site-specific mutations include insertions, substitutions, deletions or rearrangements of from 1 to 3, up to about 5–15 or more altered nucleotides (e.g., altered from a wild-type RSV sequence, from a sequence of a selected mutant RSV strain, or from a parent recombinant RSV clone subjected to mutagenesis). Such site-specific mutations may be incorporated at, or within the region of, a selected, biologically derived mutation. Alternatively, the mutations can be introduced in various other contexts within an RSV clone, for example at or near a cis-acting regulatory sequence or nucleotide sequence encoding a protein active site, binding site, immunogenic epitope, etc.

Site-specific RSV mutants typically retain a desired attenuating phenotype, but may additionally exhibit altered phenotypic characteristics unrelated to attenuation, e.g., enhanced or broadened immunogenicity, and/or improved growth. Further examples of desired, site-specific mutants include recombinant RSV designed to incorporate additional, stabilizing nucleotide mutations in a codon specifying an attenuating mutation. Where possible, two or more nucleotide substitutions are introduced at codons that specify attenuating amino acid changes in a parent mutant or recombinant RSV clone, yielding a biologically derived or recombinant RSV having genetic resistance to reversion from an attenuated phenotype. In other embodiments, site-specific nucleotide substitutions, additions, deletions or rearrangements are introduced upstream (N-terminal direction) or downstream (C-terminal direction), e.g., from 1 to 3, 5–10 and up to 15 nucleotides or more 5' or 3', relative to a targeted nucleotide position, e.g., to construct or ablate an existing cis-acting regulatory element.

In addition to single and multiple point mutations and site-specific mutations, changes to M2 ORF2 deletion and knock out mutant RSV disclosed herein include deletions, insertions, substitutions or rearrangements of whole genes or genome segments. These mutations may alter small numbers of bases (e.g., from 15–30 bases, up to 35–50 bases or more), large blocks of nucleotides (e.g., 50–100, 100–300, 300–500, 500–1,000 bases), or nearly complete or complete genes (e.g., 1,000–1,500 nucleotides, 1,500–2,500 nucleotides, 2,500–5,000, nucleotides, 5,00–6,5000 nucleotides or more) in the donor or recipient genome or antigenome, depending upon the nature of the change (i.e., a small number of bases may be changed to insert or ablate an immunogenic epitope or change a small genome segment, whereas large block(s) of bases are involved when genes or large genome segments are added, substituted, deleted or rearranged.

In additional aspects, the invention provides for supplementation of mutations adopted into a recombinant RSV clone from biologically derived RSV, e.g., cp and ts mutations, with additional types of mutations involving the same or different genes in a further modified M2-2 deletion or ablation mutant. RSV encodes ten mRNAs and ten or eleven proteins. Three of these are transmembrane surface proteins, namely the attachment G rotein, fusion F protein involved in penetration, and small hydrophobic SH protein. G and F are the major viral neutralization and protective antigens. Four additional proteins are associated with the viral nucleocapsid, namely the RNA binding protein N, the phosphoprotein P, the large polymerase protein L, and the transcription elongation factor M2 ORF 1. A second ORF in M2, the M2-2 ORF encodes an important RNA regulatory factor. The matrix M protein is part of the inner virion and probably mediates association between the nucleocapsid and the envelope. Finally, there are two nonstructural proteins, NS1 and NS2, of unknown function. Each of these proteins can be selectively altered in terms of expression levels, or can be added deleted, substituted or rearranged, in whole or in part, alone or in combination with other desired modifications, to yield an M2 ORF2 deletion or knock out mutant RSV exhibiting novel vaccine characteristics.

Thus, in addition to or in combination with attenuating mutations adopted from biologically derived RSV mutants, the present invention also provides a range of additional methods for attenuating or otherwise modifying the phenotype of M2 ORF2 deletion and knock out mutant RSV based on recombinant engineering of infectious RSV clones. A variety of alterations can be produced in an isolated polynucleotide sequence encoding the donor gene or genome segment or the background genome or antigenome for incorporation into infectious clones. More specifically, to achieve desired structural and phenotypic changes in recombinant RSV, the invention allows for introduction of modifications which delete, substitute, introduce, or rearrange a selected nucleotide or plurality of nucleotides from a parent genome or antigenome, as well as mutations which delete, substitute, introduce or rearrange whole gene(s) or genome segment(s), within an M2 ORF2 deletion or knock out mutant RSV clone.

Desired modifications of infectious RSV according to the invention are typically selected to specify a desired phenotypic change, e.g., a change in viral growth, temperature sensitivity, ability to elicit a host immune response, attenuation, etc. These changes can be brought about either in a donor or recipient genome or antigenome by, e.g., mutagenesis of a parent RSV clone to ablate, introduce or rearrange a specific gene(s) or genome region(s) (e.g., a genome segment that encodes a protein structural domain, such as a cytoplasmic, transmembrane or extracellular domain, an immunogenic epitope, binding region, active site, etc. or a cis-acting signal). Genes of interest in this regard include all of the genes of the RSV genome: 3'-NS1-NS2-N-P-M-SH-G-F-M21/M2-2-L-5', as well as heterologous genes from other RSV, other viruses and a variety of other non-RSV sources as indicated herein.

Also provided are modifications in M2 ORF2 deletion and knock out mutant RSV which simply alter or ablate expression of a selected gene, e.g., by introducing a termination codon within a selected RSV coding sequence, changing the position of an RSV gene relative to an operably linked promoter, introducing or removing an upstream start codon to alter rates of expression, modifying (e.g., by changing position, altering an existing sequence, or substituting an existing sequence with a heterologous sequence) GS and/or GE transcription signals to alter phenotype (e.g., growth, temperature restrictions on transcription, etc.), and various other deletions, substitutions, additions and rearrangements that specify quantitative or qualitative changes, e.g., in viral replication, transcription of selected gene(s), or translation of selected protein(s).

The ability to analyze and incorporate other types of attenuating mutations into M2 ORF2 deletion and knock out mutants for vaccine development extends to a broad assemblage of targeted changes in RSV clones. For example, deletion of the SH gene yields a recombinant RSV having novel phenotypic characteristics, including enhanced growth. In the present invention, an SH, NS1, NS2 or G gene (or any other selected, non-essential gene or genome segment) is deleted in a recombinant RSV, which may also have one or more additional mutations specifying an attenuated phenotype, e.g., one or more mutation(s) adopted from a biologically derived attenuated RSV mutant. In exemplary embodiments, an SH, NS1, NS2 or G gene is deleted in combination with one or more cp and/or ts mutations adopted from cpts248/404, cpts530/1009, cpts530/1030, or another selected mutant RSV strain or with other changes determined empirically, to yield a recombinant RSV having increased yield of virus, enhanced attenuation, and resistance to phenotypic reversion, due to the combined effects of the different mutations.

Any RSV gene which is not essential for growth, for example the SH, NS1 NS2 or G genes, can be ablated or otherwise modified in a recombinant RSV to yield desired effects on virulence, pathogenesis, immunogenicity and other phenotypic characters. For example, ablation by deletion of a non-essential gene such as SH results in enhanced viral growth in culture. Without wishing to be bound by theory, this effect is likely due in part to a reduced nucleotide length of the viral genome. In the case of one exemplary SH-minus clone, the modified viral genome is 14,825 nt long, 398 nucleotides less than wild-type. By engineering similar mutations that decrease genome size, e.g., in other coding or noncoding regions elsewhere in the RSV genome, such as in the P, M, F and M2 genes, the invention provides several readily obtainable methods and materials for improving RSV growth.

In addition, a variety of other genetic alterations can be produced in a RSV genome or antigenome for incorporation into infectious M2 ORF2 deletion and knock out mutant RSV, alone or together with one or more attenuating mutations adopted from a biologically derived mutant RSV. Additional heterologous genes and genome segments (e.g. from different RSV genes, different RSV strains or types, or non-RSV sources) may be inserted in whole or in part, the order of genes changed, gene overlap removed, an RSV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Also provided within the invention are genetic modifications in an M2 ORF2 deletion or knock out mutant RSV which alter or ablate the expression of a selected gene or genome segment without removing the gene or genome segment from the RSV clone. For example, this can be achieved by introducing a frame shift mutation or termination codon within a selected coding sequence, changing the position of a gene or introducing an upstream start codon to alter its rate of expression, or changing GS and/or GE transcription signals to alter phenotype (e.g., growth, temperature restrictions on transcription, etc.). In more detailed aspects of the invention, M2 ORF2 deletion and knock out mutant RSV are provided in which expression of the NS2 gene is ablated at the translational level without deletion of the gene or of a segment thereof, by, e.g., introducing two tandem translational termination codons into a translational open reading frame (ORF). This yields viable virus in which a selected gene has been silenced at the level of translation without deleting its gene. These forms of knock-out virus will often exhibit reduced growth rates and small plaque sizes in tissue culture. Thus, these methods provide yet additional, novel types of attenuating mutations which ablate expression of a viral gene that is not one of the major viral protective antigens. In this context, knock-out virus phenotypes produced without deletion of a gene or genome segment can be alternatively produced by deletion mutagenesis, as described herein, to effectively preclude correcting mutations that may restore synthesis of a target protein. Several other gene knock-outs for M2 ORF2 deletion and knock out mutants can be made using alternate designs and methods that are well known in the art (as described, for example, in (Kretschmer et al., *Virology* 216:309–316, 1996; Radicle et al., *Virology* 217:418–412, 1996; and Kato et al., *EMBOSS J.* 16:178–587, 1987; and Schneider et al., *Virology* 277:314–322, 1996, each incorporated herein by reference).

Other mutations for incorporation into M2 ORF2 deletion and knock out mutant RSV of the invention include mutations directed toward cis-acting signals, which can be identified, e.g., by mutational analysis of RSV minigenomes. For example, insertional and deletional analysis of the leader and trailer and flanking sequences identifies viral promoters and transcription signals and provides a series of mutations associated with varying degrees of reduction of RNA replication or transcription. Saturation mutagenesis (whereby each position in turn is modified to each of the nucleotide alternatives) of these cis-acting signals also has identified many mutations which reduced (or in one case increased) RNA replication or transcription. Any of these mutations can be inserted into an M2 ORF2 deletion or knock out mutant RSV antigenome or genome as described herein. Evaluation and manipulation of trans-acting proteins and cis-acting RNA sequences using the complete antigenome cDNA is assisted by the use of RSV minigenomes (see, e.g., Grosfeld et al., *J. Virol.* 69: 5677–5686, 1995, incorporated herein by reference), whose helper-dependent status is useful in the characterization of those mutants which are too inhibitory to be recovered in replication-independent infectious virus.

Additional mutations within M2 ORF2 deletion and knock out mutant RSV involve replacement of the 3' end of genome with its counterpart from antigenome, which is associated with changes in RNA replication and transcription. In addition, the intergenic regions (Collins et al., *Proc. Natl. Acad. Sci. USA* 83:4594–4598, 1986, incorporated herein by reference) can be shortened or lengthened or changed in sequence content, and the naturally-occurring gene overlap (Collins et al., *Proc. Natl. Acad. Sci. USA* 84:5134–5138, 1987, incorporated herein by reference) can be removed or changed to a different intergenic region by the methods described herein. In one exemplary embodiment, the level of expression of specific RSV proteins, such as the protective F and G antigens, can be increased by substituting the natural sequences with ones which have been made synthetically and designed to be consistent with efficient translation. In this context, it has been shown that codon usage can be a major factor in the level of translation of mammalian viral proteins (Haas et al., *Current Biol.* 6:315–324, 1996, incorporated herein by reference). Examination of the codon usage of the mRNAs encoding the F and G proteins of RSV, which are the major protective antigens, shows that the usage is consistent with poor expression. Thus, codon usage can be improved by the recombinant methods of the invention to achieve improved expression for selected genes. In another exemplary embodiment, a sequence surrounding a translational start site (preferably including a nucleotide in the -3 position) of a selected RSV gene is modified, alone or in combination with introduction of an upstream start codon, to modulate RSV gene expression by specifying up- or down-regulation of translation.

Alternatively, or in combination with other RSV modifications disclosed herein, M2 ORF2 deletion and knock out mutant RSV gene expression can be modulated by altering a transcriptional GS signal of a selected gene(s) of the virus. In one exemplary embodiment, the GS signal of NS2 is modified to include a defined mutation (e.g., the 404(M2) mutation described herein) to superimpose a ts restriction on viral replication.

In alternative embodiments, levels of gene expression in the M2 ORF2 deletion and knock out mutants are modified at the level of transcription. In one aspect, the position of a selected gene in the RSV gene map can be changed to a more promoter-proximal or promoter-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels often attended by a commensurate decrease in expression levels for reciprocally, positionally substituted genes. In one example, the NS2 gene (second in order in the RSV gene map) is substituted in position for the SH gene (sixth in order), yielding a predicted decrease in expression of NS2. In other exemplary embodiments, the F and G genes are transpositioned singly or together to a more promoter-proximal or promoter-distal site within the RSV gene map to achieve higher or lower levels of gene expression, respectively. These and other transpositioning changes yield novel M2 ORF2 deletion and knock out mutants of RSV having attenuated phenotypes, for example due to decreased expression of selected viral proteins involved in RNA replication, or having other desirable properties such as increased antigen expression.

Infectious M2 ORF2 deletion and knock out mutant RSV clones of the invention can also be engineered according to the methods and compositions disclosed herein to enhance immunogenicity and induce a level of protection greater than that provided by infection with a wild-type RSV or a parent RSV. For example, an immunogenic epitope from a heterologous RSV strain or type, or from a non-RSV source such as PIV, can be added to a recombinant clone by appropriate nucleotide changes in the polynucleotide sequence encoding the genome or antigenome. Alternatively, RSV can be engineered to add or ablate (e.g., by amino acid insertion, substitution or deletion) immunogenic proteins, protein domains, or forms of specific proteins (such as the secreted form of G) associated with desirable or undesirable immunological reactions.

Within the methods of the invention, additional genes or genome segments may be inserted into or proximate to the M2 ORF2 deletion and knock out mutant RSV genome or antigenome. These genes may be under common control with recipient genes, or may be under the control of an independent set of transcription signals. Genes of interest include the RSV genes identified above, as well as non-RSV genes. Non-RSV genes of interest include those encoding cytokines (e.g., IL-2 through IL-18, especially IL-2, IL-4, IL-6 and IL-12, IL-18, etc.), gamma-interferon, GM-CSF, chemokines and proteins rich in T helper cell epitopes. These additional proteins can be expressed as a separate protein, or as a chimera engineered from a second copy of one of the RSV proteins, such as SH. This provides the ability to modify and improve the immune responses against RSV both quantitatively and qualitatively.

In exemplary embodiments of the invention, insertion of foreign genes or genome segments, and in some cases of noncoding nucleotide sequences, within an M2 ORF2 deletion or knock out mutant RSV genome results in a desired increase in genome length causing yet additional, desired phenotypic effects. Increased genome length results in attenuation of the resultant RSV, dependent in part upon the length of the insert. In addition, the expression of certain proteins, e.g. a cytokine, from a non-RSV gene inserted into M2 ORF2 deletion and knock out mutant RSV will result in attenuation of the virus due to the action of the protein. Exemplary cytokines that yield an infectious, attenuated viral phenotype and high level cytokine expression from RSV transfected cells include interleukin-2 (IL-2), IL-4, GM-CSF, and γ-interferon. Additional effects including augmentation of cellular and humoral immune responses will also attend introduction of cytokines into recombinant RSV of the invention.

Deletions, insertions, substitutions and other mutations involving changes of whole viral genes or genome segments within an M2 ORF2 deletion or knock out mutants yield genetically stable vaccine candidates, which are particularly important in the case of immunosuppressed individuals. Many of these changes will result in attenuation of resultant vaccine strains, whereas others will specify different types of desired phenotypic changes. For example, accessory (i.e., not essential for in vitro growth) genes are excellent candidates to encode proteins that specifically interfere with host immunity (see, e.g., Kato et al., *EMBO. J.* 16:578–87, 1997, incorporated herein by reference). Ablation of such genes in vaccine viruses is expected to reduce virulence and pathogenesis and/or improve immunogenicity.

In alternative aspects of the invention, the infectious M2 ORF2 deletion and knock out mutant RSV produced from a cDNA-expressed genome or antigenome can be any of the RSV or RSV-like strains, e.g., human, bovine, murine, etc., or of any pneumovirus, e.g., pneumonia virus of mice avian pneumovirus (previously called turkey rhinotracheitis virus). To engender a protective immune response, the RSV strain may be one which is endogenous to the subject being immunized, such as human RSV being used to immunize humans. The genome or antigenome of endogenous RSV can be modified, however, to express RSV genes or genome segments from a combination of different sources, e.g., a combination of genes or genome segments from different RSV species, subgroups, or strains, or from an RSV and another respiratory pathogen such as PIV.

In certain embodiments of the invention, M2 ORF2 deletion and knock out mutant RSV are provided wherein genes or genome segments within a human or bovine RSV (e.g., a human RSV background genome or antigenome) are replaced with counterpart heterologous genes or genome segments from a non-human, non-bovine RSV, e.g., a murine pneumonia virus. Substitutions, deletions, and additions of RSV genes or genome segments in this context can include part or all of one or more of the NS1, NS2, N, P, M, SH, M2(ORF1), M2(ORF2) and L genes, or part or all of the G and F genes which preferably does not include the major neutralization and protective epitopes. Also, human or bovine RSV cis-acting sequences, such as promoter or transcription signals, can be replaced with non-human, non-bovine counterpart sequences. Thus, infectious M2 ORF2 deletion and knock out mutant RSV intended for administration to humans can be a human RSV that has been modified to contain genes from a murine RSV in addition to bovine RSV.

Replacement of a human RSV coding sequence (e.g., of NS1, NS2, SH, or G) or non-coding sequence (e.g., a promoter, gene-end, gene-start, intergenic or other cis-acting element) with a counterpart bovine RSV sequence yields chimeric RSV having a variety of possible attenuating and other phenotypic effects. In particular, host range and other desired effects arise from substituting a bovine RSV gene imported within a human RSV background, wherein the bovine gene does not function efficiently in a human cell, e.g., from incompatibility of the heterologous sequence or protein with a biologically interactive human RSV sequence or protein (i.e., a sequence or protein that ordinarily cooperates with the substituted sequence or protein for viral transcription, translation, assembly, etc.) or, more typically in a host range restriction, with a cellular protein or some other aspect of the cellular milieu which is different between the permissive and less permissive host. In one such embodiment, a chimeric bovine-human RSV incorporates a substitution of the human RSV NP gene or genome segment with a counterpart bovine NP gene or genome segment, which chimera can optionally be constructed to incorporate additional genetic changes, e.g., point mutations or gene deletions. In exemplary embodiments, bovine RSV sequences are selected for introduction into human RSV based on known aspects of bovine RSV structure and function, as provided in, e.g., Pastey et al., *J. Gen. Viol.* 76:193–197, 1993; Pastey et al., *Virus Res.* 29:195–202, 1993; Zamora et al., *J. Gen. Virol.* 73:737–741, 1992; Mallipeddi et al., *J. Gen. Virol.* 74:2001–2004, 1993; Mallipeddi et al., *J. Gen. Virol.* 73:2441–2444, 1992; and Zamora et al., *Virus Res.* 24:115–121, 1992, each incorporated herein by reference, and in accordance with the teachings disclosed herein.

In other embodiments of the invention mutations of interest for introduction within M2 ORF2 deletion and knock out mutant RSV are modeled after a tissue culture-adapted nonpathogenic strain of pneumonia virus of mice (the murine counterpart of human RSV) which lacks a cytoplasmic tail of the G protein (Randhawa et al., *Virology* 207:240–245, 1995). Accordingly, in one aspect of the invention the cytoplasmic and/or transmembrane domains of one or more of the human RSV glycoproteins, F, G and SH, are added, deleted, modified, or substituted within a chimeric RSV using a heterologous counterpart sequence (e.g., a sequence from a cytoplasmic, or transmembrane domain of a F, G, or SH protein of a murine pneumonia virus) to achieve a desired attenuation. As another example, a nucleotide sequence at or near the cleavage site of the F protein, or the putative attachment domain of the G protein, can be modified by point mutations, site-specific changes, or by alterations involving entire genes or genome segments to achieve novel effects on viral growth in tissue culture and/or infection and pathogenesis.

In related aspects of the invention, the disclosed modifications relating to M2-2 are incorporated within chimeric human-bovine RSV, which are recombinantly engineered to incorporate nucleotide sequences from both human and bovine RSV strains to produce an infectious, chimeric virus or subviral particle. Exemplary human-bovine chimeric RSV of the invention incorporate a chimeric RSV genome or antigenome comprising both human and bovine polynucleotide sequences, as well as a major nucleocapsid (N) protein, a nucleocapsid phosphoprotein (P), a large polymerase protein (L), and a RNA polymerase elongation factor. Additional RSV proteins may be included in various combinations to provide a range of infectious subviral particles, up to a complete viral particle or a viral particle containing supernumerary proteins, antigenic determinants or other additional components.

Chimeric human-bovine RSV for use within the invention are generally described in U.S. Patent Application entitled PRODUCTION OF ATTENUATED, HUMAN-BOVINE CHIMERIC RESPIRATORY SYNCYTIAL VIRUS VACCINES, filed by Bucholz et al. on Jun. 23, 2000, and in its priority U.S. Provisional Patent Application Serial No. 60/143,132 (each incorporated herein by reference). These chimeric recombinant RSV include a partial or complete "background" RSV genome or antigenome derived from or patterned after a human or bovine RSV strain or subgroup virus combined with one or more heterologous gene(s) or genome segment(s) of a different RSV strain or subgroup virus to form the human-bovine chimeric RSV genome or antigenome. In certain aspects of the invention, chimeric RSV incorporate a partial or complete bovine RSV background genome or antigenome combined with one or more heterologous gene(s) or genome segment(s) from a human RSV. In alternate aspects of the invention chimeric RSV incorporate a partial or complete human RSV background genome or antigenome combined with one or more heterologous gene(s) or genome segment(s) from a bovine RSV.

In exemplary embodiments, the invention is directed to an infectious M2 ORF2 deletion or knock out respiratory syncytial viruses (RSVs) that comprise a major nucleocapsid (N) protein, a nucleocapsid phosphoprotein (P), a large polymerase protein (L), a RNA polymerase elongation factor, and a partial or complete RSV background genome or antigenome of a human or bovine RSV combined with one or more heterologous gene(s) and/or genome segment(s) of a different RSV to form a human-bovine chimeric RSV genome or antigenome. The heterologous gene(s) and/or genome segment(s) that are useful within the invention include one or more RSV NS1, NS2, N, P, M, SH, M2(ORF1), M2(ORF2), L, F or G gene(s) or genome segment(s). Alternatively, heterologous genes and genome segments for incorporation within human-bovine chimeric RSV may include a leader, trailer or intergenic region of the RSV genome, or a segment thereof. Various modifications to the M2-2 gene, including partial or complete deletions and other modifications that reduce or eliminate M2-2 expression can be incorporated within the chimeric genome or antigenome.

Within more detailed embodiments, human-bovine chimeric RSV of the invention incorporate one or more heterologous genes and/or genome segments that encode a RSV F, G and/or SH glycoprotein or an immunogenic domain or epitope thereof. Alternatively, the human-bovine chimeric RSV may incorporate a chimeric glycoprotein having both human and bovine glycoprotein domains or immunogenic epitopes. For example, the latter type of chimera may be constructed by incorporation into a bovine background genome or antigenome a heterologous genome segment encoding a glycoprotein ectodomain in proper reading frame with a genome segment encoding a functional remaining portion of the corresponding glycoprotein in the bovine genome or antigenome, whereby the resultant chimeric virus expresses a functional chimeric glycoprotein.

In other alternative embodiments of the invention, human-bovine chimeric RSV are provided wherein a human RSV is attenuated by incorporation of a selected bovine gene, genome segment, or plurality of genes or genome segments. In certain embodiments selected heterologous gene sets from BRSV are coordinately transferred into a HRSV background genome or antigenome. Exemplary bovine RSV genes from which individual or coordinately transferred groups of genes may be selected include the RSV N, P, NS1, NS2, M2-1 and M genes, which may be replaced singly or in any combination in a human RSV background genome or antigenome by one or more heterologous gene(s) from a bovine RSV to yield an attenuated chimeric derivative. In more detailed aspects, both N and P genes of a human RSV are replaced coordinately by counterpart N and P genes from a bovine RSV. This coordinate gene replacement is facilitated by functional cooperativity between certain genes in the RSV genome, which often arises in the case of neighboring gene pairs in the genome. Thus, in other alternative embodiments, both NS1 and NS2 genes of a human RSV are replaced by counterpart NS1 and NS2 genes from a bovine RSV. In yet additional embodiments, two or more of the M2-1, M2-2 and L genes of a HRSV are replaced by counterpart genes from a bovine RSV. For certain vaccine candidates within the invention for which a high level of host-range restriction is desired, each of the N, P, NS1, NS2, M2-1 and M genes of a human RSV are replaced by counterpart N, P, NS1, NS2, M2-1 and M genes from a bovine RSV. Within these various constructs, any selected modification to the M2-2 gene disclosed herein, including partial or complete deletion of the gene or other modification of the gene (e.g., altering or ablating a cis-acting regulatory sequence or rearranging the position of M2-2), can be incorporated in the chimeric genome or antigenome.

Within a different aspect of the invention, human-bovine chimeric RSV having a modification involving M2-2 as disclosed herein are constructed wherein the chimeric genome or antigenome comprises a partial or complete bovine RSV background genome or antigenome combined with one or more heterologous gene(s) and/or genome segment(s) from a human RSV. In certain embodiments, one or more human RSV glycoprotein genes selected from F, G and SH, or one or more genome segment(s) encoding cytoplasmic domain, transmembrane domain, ectodomain or immunogenic epitope portion(s) of F, G, and/or SH is/are added or substituted within a partial or complete bovine RSV background genome or antigenome. For example, one or both human RSV glycoprotein genes F and G may be substituted to replace one or both counterpart F and G glycoprotein genes in a partial bovine RSV background genome or antigenome. Within these and related embodiments, the human-bovine chimeric genome or antigenome can incorporate antigenic determinants from one or both subgroup A and subgroup B human RSV. In more detailed aspects, both human RSV glycoprotein genes F and G are substituted to replace counterpart F and G glycoprotein genes in the bovine RSV background genome or antigenome. An exemplary human-bovine chimeric RSV bearing these features in the examples below is rBRSV/A2. In combination with one or more of the modifications provided in this chimeric virus, the invention will incorporate a selected modification involving M2-2 as disclosed herein.

Yet additional human-bovine chimeric RSV of the invention having a modification of M2-2 incorporate one or more human RSV glycoprotein genes selected from F, G and SH which are added or substituted at a position that is more promoter-proximal compared to a wild-type gene order position of a counterpart gene or genome segment within a partial or complete bovine RSV background genome or antigenome. In one such embodiment, both human RSV glycoprotein genes G and F are substituted at gene order positions 1 and 2, respectively, to replace counterpart G and F glycoprotein genes deleted at wild type positions 7 and 8, respectively in a partial bovine RSV background genome or antigenome. An exemplary human-bovine chimeric RSV bearing these features described in the above-incorporated disclosures is rBRSV/A2-G1F2.

Coordinate gene transfers within human-bovine chimeric RSV are also directed to introduction of human antigenic genes within a bovine background genome or antigenome. In certain embodiments, one or more human RSV envelope-associated genes selected from F, G, SH, and M is/are added or substituted within a partial or complete bovine RSV background genome or antigenome. For example, one or more human RSV envelope-associated genes selected from F, G, SH, and M may be added or substituted within a partial bovine RSV background genome or antigenome in which one or more envelope-associated genes selected from F, G, SH, and M is/are deleted. In more detailed aspects, one or more genes from a gene set defined as human RSV envelope-associated genes F, G, and M are added within a partial bovine RSV background genome or antigenome in which envelope-associated genes F, G, SH, and M are deleted. An exemplary human-bovine chimeric RSV bearing these features described in the incorporated references is rBRSV/A2-MGF. In combination with one or more of the modifications provided in this chimeric virus, the invention will incorporate a selected modification involving M2-2 as disclosed herein.

In yet additional aspects of the invention, M2 ORF2 deletion and knock out RSV can be readily designed as "vectors" to incorporate antigenic determinants from different pathogens, including more than one RSV strain or group (e.g., both human RSV A and RSV B subgroups), human parainfluenza virus (HPIV) including HPIV3, HPIV2 and HPIV1, measles virus and other pathogens (see, e.g., U.S. Provisional Patent Application Serial No. 60/170,195; U.S. patent application Ser. No. 09/458,813; and U.S. patent application Ser. No. 09/459,062, each incorporated herein by reference). Within various embodiments, the recombinant genome or antigenome comprises a partial or complete RSV "vector genome or antigenome" combined with one or more heterologous genes or genome segments encoding one or more antigenic determinants of one or more heterologous pathogens. The heterologous pathogen may be a heterologous RSV (i.e., a RSV of a different strain or subgroup), and the heterologous gene or genome segment may encode a RSV NS1, NS2, N, P, M, SH, M2(ORF1), M2(ORF2), L, F or G protein or fragment (e.g., a immunogenic domain or epitope) thereof. For example, the vector genome or antigenome may be a partial or complete RSV A genome or antigenome and the heterologous gene(s) or genome segment(s) may encode antigenic determinant(s) of a RSV B subgroup virus.

In alternative embodiments, the RSV vector genome or antigenome is a partial or complete bovine RSV (BRSV) genome or antigenome and the heterologous gene(s) or genome segment(s) encoding the antigenic determinant(s) is/are of one or more human RSVs (HRSVs). For example, the partial or complete BRSV genome or antigenome may incorporate one or more gene(s) or genome segment(s) encoding one or more HRSV glycoprotein genes selected from F, G and SH, or one or more genome segment(s) encoding cytoplasmic domain, transmembrane domain, ectodomain or immunogenic epitope portion(s) of F, G, and/or SH of HRSV.

In other alternate embodiments, M2 ORF2 deletion and knock out RSV designed as "vectors" for carrying heterologous antigenic determinants incorporate one or more antigenic determinants of a non-RSV pathogen, such as a human parainfluenza virus (HPIV). In one exemplary embodiment, one or more HPIV1, HPIV2, or HPIV3 gene(s) or genome segment(s) encoding one or more HN and/or F glycoprotein(s) or antigenic domain(s), fragment(s) or epitope(s) thereof is/are added to or incorporated within the partial or complete HRSV vector genome or antigenome. In more detailed embodiments, a transcription unit comprising an open reading frame (ORF) of an HPIV1, HPIV2, or HPIV3 HN or F gene is added to or incorporated within the chimeric HRSV vector genome or anti genome.

In yet additional alternate embodiments, the M2 ORF2 deletion or knock out vector genome or antigenome comprises a partial or complete HRSV or BRSV genome or antigenome and the heterologous pathogen is selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses. Based on this exemplary list of candidate pathogens, the selected heterologous antigenic determinant(s) may be selected from measles virus HA and F proteins, subgroup A or subgroup B respiratory syncytial virus F, G, SH and M2 proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein; filovirus G protein, bunyavirus G protein, Flavivirus E and NS1 proteins, and alphavirus E protein, and antigenic domains, fragments and epitopes thereof. In one embodiment, the heterologous pathogen is measles virus and the heterologous antigenic determinant(s) is/are selected from the measles virus HA and F proteins and antigenic domains, fragments and epitopes thereof. To achieve such a chimeric construct, a transcription unit comprising an open reading frame (ORF) of a measles virus HA gene may be added to or incorporated within a HRSV vector genome or antigenome.

In all embodiments of the invention that involve construction of a chimeric RSV, the addition or substitution of a heterologous or "donor" polynucleotide to a recipient or "background" genome or antigenome can involve only a portion of a donor gene of interest. Commonly, non-coding nucleotides such as cis-acting regulatory elements and intergenic sequences need not be transferred with the donor gene coding region. Thus, a coding sequence (e.g., a partial or complete open reading frame (ORF)) of a particular gene may be added or substituted to the partial or complete background genome or antigenome under control of a heterologous promoter (e.g., a promoter existing in the background genome or antigenome) of a counterpart gene or different gene as compared to the donor sequence. A variety of additional genome segments provide useful donor polynucleotides for inclusion within a chimeric genome or antigenome to express chimeric RSV having novel and useful properties. For example, heterologous genome segments may encode part or all of a glycoprotein cytoplasmic tail region, transmembrane domain or ectodomain, an epitopic site or region, a binding site or region containing a binding site, an active site or region containing an active site, etc., of a selected protein from a human or bovine RSV. These and other genome segments can be added to a complete background genome or antigenome or substituted therein for a counterpart genome segment to yield novel chimeric RSV recombinants. Certain recombinants will express a chimeric protein, e.g., a protein having a cytoplasmic tail and/or transmembrane domain of one RSV fused to an ectodomain of another RSV.

In other detailed aspects of the invention, M2 ORF2 deletion and knock out viruses are created or modified by shifting a relative gene order or spatial position of one or more genes or genome segments within a recombinant RSV genome or antigenom—to generate a recombinant vaccine virus that is infectious, attenuated and immunogenic in humans and other mammals (see, U.S. Provisional Patent Application Ser. No. 60/213,708 entitled RESPIRATORY SYNCYTIAL VIRUS VACCINES EXPRESSING PROTECTIVE ANTIGENS FROM PROMOTOR-PROXIMAL GENES, filed by Krempl et al., Jun. 23, 2000, incorporated herein by reference). These recombinant RSVs of the invention typically comprise a major nucleocapsid (N) protein, a nucleocapsid phosphoprotein (P), a large polymerase protein (L), a RNA polymerase elongation factor, and a partial or complete recombinant RSV genome or antigenome having one or more positionally shifted RSV genes or genome segments within the recombinant genome or antigenome. In certain aspects of the invention, the recombinant RSV features one or more positionally shifted genes or genome segments that may be shifted to a more promoter-proximal or promoter-distal position by insertion, deletion, or rearrangement of one or more displacement polynucleotides within the partial or complete recombinant RSV genome or antigenome. Displacement polynucleotides may be inserted or rearranged into a non-coding region (NCR) of the recombinant genome or antigenome, or may be incorporated in the recombinant RSV genome or-antigenome as a separate gene unit (GU).

In exemplary embodiments of the invention, isolated infectious recombinant RSV are constructed by addition, deletion, or rearrangement of one or more displacement polynucleotides that may be selected from one or more RSV gene(s) or genome segment(s) selected from RSV NS1, NS2, N, P, M, SH, M2(ORF1), M2(ORF2), L, F and G genes and genome segments and leader, trailer and intergenic regions of the RSV genome and segments thereof. In more detailed embodiments, polynucleotide inserts, and deleted or rearranged elements within the recombinant RSV genome or antigenome are selected from one or more bovine RSV (BRSV) or human RSV (HRSV) gene(s) or genome segment(s) selected from RSV NS1, NS2, N, P, M, SH, M2(ORF1), M2(ORF2), L, F and G gene(s) or genome segment(s) and leader, trailer and intergenic regions of the RSV genome or segments thereof.

In certain aspects of the invention, displacement polynucleotides are deleted to form the recombinant RSV genome or antigenome, to create or supplement the M2 ORF2 deletion or knock out mutation. Deletion of a displacement polynucleotide in this manner causes a positional shift of one or more "shifted" RSV genes or genome segments within the recombinant genome or antigenome to a more promoter-proximal position relative to a position of the shifted gene(s) or genome segment(s) within a wild type RSV (e.g., HRSV A2 or BRSV kansas strain) genome or antigenome. Exemplary displacement polynucleotides that may be deleted in this manner to form the recombinant RSV genome or antigenome may be selected from one or more RSV NS1, NS2, SH, M2(ORF2), or G gene(s) or genome segment(s) thereof.

In more detailed embodiments of the invention, a displacement polynucleotide comprising a RSV NS1 gene is deleted to form the recombinant RSV genome or antigenome. Alternatively, a displacement polynucleotide comprising a RSV NS2 gene may be deleted to form the recombinant RSV genome or antigenome. Alternatively, a displacement polynucleotide comprising a RSV SH gene may be deleted to form the recombinant RSV genome or antigenome. Alternatively, a displacement polynucleotide comprising RSV M2(ORF2) can be deleted to form the recombinant RSV genome or antigenome. Alternatively, a displacement polynucleotide comprising a RSV G gene may be deleted to form the recombinant RSV genome or antigenome or antigenome.

In yet additional embodiments, multiple displacement polynucleotides comprising RSV genes or genome segments may be deleted to create or modify a M2 ORF2 deletion or knock out mutant RSV. For example, RSV F and G genes may both be deleted to further modify the recombinant RSV genome or antigenome or antigenome having an M2-2 deletion or knock out mutation. Alternatively, the RSV NS1 and NS2 genes may both be deleted to form the recombinant RSV genome or antigenome or antigenome. Alternatively, the RSV SH and NS2 genes may both be deleted in the recombinant RSV genome or antigenome or antigenome. Alternatively, the RSV SH, NS1 and NS2 genes can all be deleted in the recombinant RSV genome or antigenome or antigenome.

In different embodiments of the invention, isolated infectious recombinant RSV having a M2 ORF2 deletion or knock out mutation are provided wherein one or more displacement polynucleotides is/are added, substituted, or rearranged within the recombinant RSV genome or antigenome to cause a positional shift of one or more shifted RSV gene(s) or genome segment(s). Among these modifications, gene and genome segment insertions and rearrangements may introduce or rearrange the subject genes or genome segments to a more promoter-proximal or promoter-distal position relative to a respective position of each subject (inserted or rearranged) gene or genome segment within a corresponding (e.g., bovine or human) wild type RSV genome or antigenome. Displacement polynucleotides which may be added, substituted, or rearranged within the recombinant RSV genome or antigenome can be selected from one or more of the RSV NS1, NS2, SH, M2(ORF2), F, and/or G gene(s) or genome segment(s) thereof.

In more detailed embodiments, displacement polynucleotides are selected for insertion or rearrangement within the M2 ORF2 deletion or knock out RSV genome or antigenome which comprises one or more RSV genes or genome segments that encode one or more RSV glycoproteins or immunogenic domains or epitopes of RSV glycoproteins. In exemplary embodiments, these displacement polynucleotides are selected from genes or genome segments encoding RSV F, G, and/or SH glycoproteins or immunogenic domains or epitopes thereof. For example, one or more RSV glycoprotein gene(s) selected from F, G and SH may be added, substituted or rearranged within the recombinant RSV genome or antigenome to a position that is more promoter-proximal or promoter-distal compared to the wild type gene order position of the gene(s).

In exemplary embodiments, the RSV glycoprotein gene G is rearranged within the recombinant RSV genome or antigenome to a gene order position that is more promoter-proximal compared to the wild type gene order position of G. In more detailed aspects, the RSV glycoprotein gene G is shifted to gene order position 1 within said recombinant RSV genome or antigenome. In other exemplary embodiments, the RSV glycoprotein gene F is rearranged within the recombinant RSV genome or antigenome to a more promoter-proximal position, for example by shifting the F gene to gene order position 1 within the recombinant genome or antigenome. In yet additional exemplary embodiments, both RSV glycoprotein genes G and F are rearranged within the recombinant RSV genome or antigenome to gene order positions that are more promoter-proximal compared to their respective wild type gene order positions. In more detailed aspects, the RSV glycoprotein gene G is shifted to gene order position 1 and the RSV glycoprotein gene F is shifted to gene order position 2.

In yet additional constructs featuring glycoprotein gene shifts, recombinant M2 ORF2 deletion and knock out RSV are produced having one or more RSV glycoprotein gene(s) selected from F, G and SH, or a genome segment thereof, added, substituted or rearranged within the recombinant RSV genome or antigenome, wherein one or more RSV NS1, NS2, SH, M2(ORF2), or G gene(s) or genome segment(s) thereof is/are deleted. Thus, a gene or genome segment of RSV F, G, or SH may be added, substituted or rearranged in a background wherein a displacement polynucleotide comprising a RSV NS1 gene is deleted to form the recombinant RSV genome or antigenome. Alternatively, a gene or genome segment of RSV F, G, or SH may be added, substituted or rearranged in a background wherein a displacement polynucleotide comprising a RSV NS2 gene is deleted to form the recombinant RSV genome or antigenome. Alternatively, a gene or genome segment of RSV F, G, or SH may be added, substituted or rearranged in a background wherein a displacement polynucleotide comprising a RSV SH gene is deleted to form the recombinant RSV genome or antigenome.

In one embodiment, the RSV glycoprotein gene G is rearranged within a recombinant RSV genome or antigenome having an SH gene deletion to a gene order position that is more promoter-proximal compared to the wild type gene order position of G. In more detailed aspects, the RSV glycoprotein gene G is shifted to gene order position 1 within the recombinant RSV genome or antigenome, as exemplified by the recombinant vaccine candidate G1/ΔSH. In another embodiment, the RSV glycoprotein gene F is rearranged within a recombinant RSV genome or antigenome having an SH gene deletion to a more promoter-proximal proximal position. In more detailed aspects, the F gene is shifted to gene order position 1, as exemplified by the recombinant F1ΔSH. In yet another embodiment, both RSV glycoprotein genes G and F are rearranged within a ΔSH recombinant RSV genome or antigenome to gene order positions that are more promoter-proximal compared to the wild type gene order positions of G and F. In more detailed aspects, the RSV glycoprotein gene G is shifted to gene order position 1 and the RSV glycoprotein gene F is shifted to gene order position 1 within the recombinant RSV genome or antigenome, as exemplified by the recombinant G1F1/ΔSH.

Yet additional examples of gene position-shifted RSV are provided for use within the invention featuring shifts of glycoprotein gene(s) selected from F, G and SH, which are produced within a recombinant RSV genome or antigenome having multiple genes or genome segments selected from RSV NS1, NS2, SH, M2(ORF2), and G gene(s) or genome segment(s) deleted (see, U.S. Patent Application Ser. No. 60/213,708 entitled RESPIRATORY SYNCYTIAL VIRUS VACCINES EXPRESSING PROTECTIVE ANTIGENS FROM PROMOTOR-PROXIMAL GENES, filed by Krempl et al., Jun. 23, 2000 incorporated herein by reference). In one example, the RSV SH and NS2 genes are both deleted to form the recombinant RSV genome or antigenome or antigenome, and one or both RSV glycoprotein genes G and F are rearranged within the recombinant RSV genome to more promoter-proximal gene order positions. In more detailed aspects, G is shifted to gene order position 1 and F is shifted to gene order position 2, as exemplified by the recombinant G1F1/ΔNS2ΔSH. In another example, all of the RSV SH, NS1 and NS2 genes are deleted to form the recombinant RSV genome or antigenome or antigenome, and one or both RSV glycoprotein genes G and F are rearranged within the recombinant RSV genome or antigenome to more promoter-proximal positions, as exemplified by the recombinant vaccine candidate G1F1/ΔNS2ΔNS2ΔSH.

In yet additional aspects of the invention, gene position-shifted RSV having a M2 ORF2 deletion or knock out mutations are combined with or incorporated within human-bovine chimeric RSV (see, U.S. Patent Application entitled PRODUCTION OF ATTENUATED, HUMAN-BOVINE CHIMERIC RESPIRATORY SYNCYTIAL VIRUS VACCINES, filed by Bucholz et al. on Jun. 23, 2000, and in its priority U.S. Provisional Patent Application Serial No. 60/143,132 (each incorporated herein by reference). Within these aspects, the recombinant genome or antigenome comprises a partial or complete human RSV (HRSV) or bovine RSV (BRSV) background genome or antigenome combined with one or more heterologous gene(s) or genome segment(s) from a different RSV to for a human-bovine chimeric RSV genome or antigenome. The heterologous gene or genome segment of the different, HRSV or BRSV may be added or substituted at a position that is more promoter-proximal or promoter-distal compared to a wild type gene order position of a counterpart gene or genome segment within the partial or complete HRSV or BRSV background genome or antigenome. In one such example, both human RSV glycoprotein genes G and F are substituted at gene order positions 1 and 2, respectively, to replace counterpart G and F glycoprotein genes deleted at wild type positions 7 and 8, respectively in a partial bovine RSV background genome or antigenome, as exemplified by the recombinant virus rBRSV/A2-G1F2. In other embodiments, one or more human RSV envelope-associated genes selected from F, G, SH, and M is/are added or substituted within a partial or complete bovine RSV background genome or antigenome. In more detailed aspects, one or more human RSV envelope-associated genes selected from F, G, SH, and M is/are added or substituted within a partial bovine RSV background genome or antigenome in which one or more envelope-associated genes selected from F, G, SH, and M is/are deleted. In one embodiment, human RSV envelope-associated genes F, G, and M are added within a partial bovine RSV background genome or antigenome in which all of the envelope-associated genes F, G, SH, and M are deleted, as exemplified by the recombinant virus rBRSV/A2-MGF.

In another alternate embodiment of the invention, isolated infectious recombinant RSV having a M2 ORF2 deletion or knock out are provided in which the RSV M2(ORF1) is shifted to a more promoter-proximal position within the recombinant RSV genome or antigenome. The result of this gene shift is to upregulate transcription of the recombinant virus.

In addition to the above described modifications to M2 ORF2 deletion and knock out mutant RSV, different or additional modifications in RSV clones can be made to facilitate manipulations, such as the insertion of unique restriction sites in various intergenic regions (e.g., a unique StuI site between the G and F genes) or elsewhere. Non-translated gene sequences can be removed to increase capacity for inserting foreign sequences.

In another aspect of the invention, compositions (e.g., isolated polynucleotides and vectors incorporating an M2 ORF2 deletion or knock out-encoding cDNA) are provided for producing an isolated infectious RSV. Using these compositions and methods, infectious RSV are generated from a RSV genome or antigenome, a nucleocapsid (N) protein, a nucleocapsid phosphoprotein (P), a large (L) polymerase protein, and an RNA polymerase elongation factor. In related aspects of the invention, compositions and methods are provided for introducing the aforementioned structural and phenotypic changes into a recombinant RSV to yield infectious, attenuated vaccine viruses.

Introduction of the foregoing defined mutations into an infectious, M2 ORF2 deletion and knock out mutant RSV clone can be achieved by a variety of well known methods. By "infectious clone" with regard to DNA is meant cDNA or its product, synthetic or otherwise, which can be transcribed into genomic or antigenomic RNA capable of serving as template to produce an infectious virus or subviral particle. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA as described herein has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. This can be through the intermediate of a single-stranded phagemid form, such as using the Muta-gene® kit of Bio-Rad Laboratories (Richmond, Calif.) or a method using a double-stranded plasmid directly as template such as the Chameleon mutagenesis kit of Stratagene (La Jolla, Calif.), or by the polymerase chain reaction employing either an oligonucleotide primer or template which contains the mutation(s) of interest. A mutated subfragment can then be assembled into the complete antigenome or genome cDNA. A variety of other mutagenesis techniques are known and available for use in producing the mutations of interest in the RSV antigenome or genome cDNA. Mutations can vary from single nucleotide changes to replacement of large cDNA pieces containing one or more genes or genome regions.

Thus, in one illustrative embodiment mutations are introduced by using the Muta-gene phagemid in vitro mutagenesis kit available from Bio-Rad. In brief, cDNA encoding a portion of an RSV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome fragment is then amplified, its sequence is confirmed, and the mutated piece is then reintroduced into the full-length genome or antigenome clone.

The ability to introduce defined mutations into infectious RSV has many applications, including the analyses of RSV molecular biology and pathogenesis. For example, the functions of RSV proteins can be investigated and manipulated by introducing mutations which ablate or reduce their level of expression, or which yield mutant protein. In one exemplary embodiment hereinbelow, recombinant RSV is constructed in which expression of a viral gene, namely the SH gene, is ablated by deletion of the mRNA coding sequence and flanking transcription signals. Surprisingly, not only could this virus be recovered, but it grew efficiently in tissue culture. In fact, its growth was substantially increased over that of the wild-type, based on both yield of infectious virus and on plaque size. This improved growth in tissue culture from the SH deletion and other RSV derivatives of the invention provides useful tools for developing RSV vaccines, which overcome the problem of RSV's poor yield in tissue culture that had complicated production of vaccine virus in other systems. These deletions are highly stable against genetic reversion, rendering the RSV clones derived therefrom particularly useful as vaccine agents.

The invention also provides methods for producing infectious M2 ORF2 deletion and knock out mutant RSV from one or more isolated polynucleotides, e.g., one or more cDNAs. According to the present invention cDNA encoding a RSV genome or antigenome is constructed for intracellular or in vitro coexpression with the necessary viral proteins to form infectious RSV. By "RSV antigenome" is meant an isolated positive-sense polynucleotide molecule which serves as the template for the synthesis of progeny RSV genome. Preferably a cDNA is constructed which is a positive-sense version of the RSV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, L and M2(ORF1) protein. In an RSV minigenome system, genome and antigenome were equally active in rescue, whether complemented by RSV or by plasmids, indicating that either genome or antigenome can be used and thus the choice can be made on methodologic or other grounds.

A native RSV genome typically comprises a negative-sense polynucleotide molecule which, through complementary viral mRNAs, encodes eleven known species of viral proteins, i.e., the nonstructural species NS1 and NS2, N, P, matrix (M), small hydrophobic (SH), glycoprotein (G), fusion (F), M2(ORF1), M2(ORF2), and L, substantially as described in (Mink et al., *Virology* 185:615–624, 1991; Stec et al., *Virology* 183:273–287, 1991; and Connors et al., *Virol.* 208:478–484, 1995; Collins et al., *Proc. Nat. Acad. Sci. USA* 93:81–85, 1996), each incorporated herein by reference. It is recognized that one or more of these 11 proteins may be expressed in structural-distinct forms which might have functional differences, and one or more distinct protein species may remain to be identified.

For purposes of the present invention the genome or antigenome of the recombinant RSV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule, or can be expressed directly from the genome or antigenome cDNA.

By recombinant RSV is meant a RSV or RSV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in RSV gene expression, for example, a promoter, a structural or coding sequence which is transcribed into RSV RNA, and appropriate transcription initiation and termination sequences.

To produce infectious RSV from cDNA-expressed genome or antigenome, the genome or antigenome is coexpressed with those RSV proteins necessary to (i) produce a nucleocapsid capable of RNA replication, and (ii) render progeny nucleocapsids competent for both RNA replication and transcription. Transcription by the genome nucleocapsid provides the other RSV proteins and initiates a productive infection. Alternatively, additional RSV proteins needed for a productive infection can be supplied by coexpression.

An RSV antigenome may be constructed for use in the present invention by assembling cloned cDNA segments, representing in aggregate the complete antigenome, by polymerase chain reaction (PCR; described in, e.g., U.S. Pat. Nos. 4,683,195 and 4,683,202, and *PCR Protocols: A Guide to Methods and Applications,* Innis et al., eds., Academic Press, San Diego, 1990, incorporated herein by reference) of reverse-transcribed copies of RSV mRNA or genome RNA.

For example, cDNAs containing the lefthand end of the antigenome, spanning from an appropriate promoter (e.g., T7 RNA polymerase promoter) and the leader region complement to the SH gene, are assembled in an appropriate expression vector, such as a plasmid (e.g., pBR322) or various available cosmid, phage, or DNA virus vectors. The vector may be modified by mutagenesis and/or insertion of synthetic polylinker containing unique restriction sites designed to facilitate assembly. For example, a plasmid vector described herein was derived from pBR322 by replacement of the PstI-EcoRI fragment with a synthetic DNA containing convenient restriction enzyme sites. Use of pBR322 as a vector stabilized nucleotides 3716–3732 of the RSV sequence, which otherwise sustained nucleotide deletions or insertions, and propagation of the plasmid was in bacterial strain DH10B to avoid an artifactual duplication and insertion which otherwise occurred in the vicinity of nt 4499. For ease of preparation the G, F and M2 genes can be assembled in a separate vector, as can be the L and trailer sequences. The right-hand end (e.g., L and trailer sequences) of the antigenome plasmid may contain additional sequences as desired, such as a flanking ribozyme and tandem T7 transcriptional terminators. The ribozyme can be hammerhead type (e.g., Grosfeld et al., J. Virol. 69:5677–5686, 1995), which would yield a 3' end containing a single nonviral nucleotide, or can any of the other suitable ribozymes such as that of hepatitis delta virus (Perrotta et al., Nature 350:434–436, 1991) which would yield a 3' end free of non-RSV nucleotides. A middle segment (e.g., G-to-M2 piece) is inserted into an appropriate restriction site of the leader-to-SH plasmid, which in turn is the recipient for the L-trailer-ribozyme-terminator piece, yielding a complete antigenome. In an illustrative example described herein, the leader end was constructed to abut the promoter for T7 RNA polymerase which included three transcribed G residues for optimal activity; transcription donates these three nonviral G's to the 5' end of the antigenome. These three nonviral G residues can be omitted to yield a 5' end free of nonviral nucleotides. To generate a nearly correct 3' end, the trailer end was constructed to be adjacent to a hammerhead ribozyme, which upon cleavage would donate a single 3'-phosphorylated U residue to the 3' end of the encoded RNA.

In certain embodiments of the invention, complementing sequences encoding proteins necessary to generate a transcribing, replicating RSV nucleocapsid are provided by one or more helper viruses. Such helper viruses can be wild-type or mutant. Preferably, the helper virus can be distinguished phenotypically from the virus encoded by the RSV cDNA. For example, it is desirable to provide monoclonal antibodies which react immunologically with the helper virus but not the virus encoded by the RSV cDNA. Such antibodies can be neutralizing antibodies. In some embodiments, the antibodies can be used to neutralize the helper virus background to facilitate identification and recovery of the recombinant virus, or in affinity chromatography to separate the helper virus from the recombinant virus. Mutations can be introduced into the RSV cDNA which render the recombinant RSV nonreactive or resistant to neutralization with such antibodies.

A variety of nucleotide insertions and deletions can be made in the M2 ORF2 deletion and knock out mutant RSV genome or antigenome to generate a properly attenuated clone. The nucleotide length of the genome of wild-type human RSV (15,222 nucleotides) is a multiple of six, and members of the Paramyxovirus and Morbillivirus genera typically abide by a "rule of six," i.e., genomes (or minigenomes) replicate efficiently only when their nucleotide length is a multiple of six (thought to be a requirement for precise spacing of nucleotide residues relative to encapsulating NP protein). Alteration of RSV genome length by single residue increments had no effect on the efficiency of replication, and sequence analysis of several different minigenome mutants following passage showed that the length differences were maintained without compensatory changes. Thus, RSV lacks the strict requirement of genome length being a multiple of six, and nucleotide insertions and deletions can be made in the RSV genome or antigenome without defeating replication of the recombinant RSV of the present invention.

Alternative means to construct cDNA encoding an M2 ORF2 deletion and knock out mutant RSV genome or antigenome include by reverse transcription-PCR using improved PCR conditions (e.g., as described in Cheng et al., Proc. Natl. Acad. Sci. USA 91:5695–5699, 1994; Samal et al., J. Virol 70:5075–5082, 1996, each incorporated herein by reference) to reduce the number of subunit cDNA components to as few as one or two pieces. In other embodiments different promoters can be used (e.g., T3, SP6) or different ribozymes (e.g., that of hepatitis delta virus. Different DNA vectors (e.g., cosmids) can be used for propagation to better accommodate the large size genome or antigenome.

The N, P and L proteins, necessary for RNA replication, require an RNA polymerase elongation factor such as the M2(ORF1) protein for processive transcription. Thus M2(ORF1) or a substantially equivalent transcription elongation factor for negative strand RNA viruses is required for the production of infectious RSV and is a necessary component of functional nucleocapsids during productive infection. The need for the M2(ORF1) protein is consistent with its role as a transcription elongation factor. The need for expression of the RNA polymerase elongation factor protein for negative strand RNA viruses is a feature of the present invention. M2(ORF1) can be supplied by expression of the complete M2-gene, either by the genome or antigenome or by coexpression therewith, although in this form the second ORF2 may also be expressed and can have an inhibitory effect on virus recovery. Therefore, for production of infectious virus using the complete M2 gene the activities of the two ORFs should be balanced to permit sufficient expression of M(ORF1) to provide transcription elongation activity yet not so much of M(ORF2) to inhibit RNA replication. Alternatively, the ORF1 protein is provided from a cDNA engineered to lack ORF2 or which encodes a defective ORF2. Efficiency of virus production may also be improved by co-expression of additional viral protein genes, such as those encoding envelope constituents (i.e., SH, M, G, F proteins).

The invention also provides novel compositions and methods for producing purified RSV proteins. The enhanced protein synthesis of M2-ORF 2 deletion and knock out mutant RSV renders these viruses particularly useful as a source of purified RSV proteins, for example to provide purified RSV antigens for preparation of subunit vaccines. In accordance with the teachings herein, cells that are amenable to productive infection by RSV are infected with a M2-ORF2 deletion or knock out mutant RSV of the invention and the cells are cultured under conditions that allow for propagation of the mutant virus. The virus is then removed from the cell culture and isolated from cellular components, for example by well known clarification methods. Thereafter one or more desired viral proteins, e.g., an RSV F and/or G antigen, can be purified using conventional chromatographic or other purification methods. By "purified RSV protein" is meant protein that is substantially free of cellular or viral protein and other contaminants that may render the protein non-suitable for clinical use. In other aspects, the subject protein, including a specific RSV protein or a combined sample of one or more and up to a complete assemblage of RSV proteins, are purified to about 85–90% purity, preferably 95% purity up to 98% purity or greater.

For both the characterization and control of RSV disease, there is a clear need for purified and partially-purified RSV antigen. In particular, there is a need for an enriched source of the RSV G and F glycoproteins, since these are the major protective and neutralization antigens. RSV antigens find a number of uses. One exemplary use is to administer the RSV antigen as an noninfectious subunitvaccine. Another use is as an antigen to monitor antibody responses in humans and experimental animals, such as in an enzyme-linked immunoadsorbant assay (ELISA). The need for purified antigens in diagnostic assays is well recognized. These exemplary uses of purified protein, namely as a vaccine and for diagnostic tests, is provided for means of illustration, not limitation.

A surprising aspect of the M2-2 knock out and deletion mutations is that they confer increased expression of RSV proteins, particularly RSV antigens. The use of a nonreplicating subunit vaccine is an attractive strategy for certain groups of potential vaccinees, such as immunocompromised individuals, older children who are seropositive for RSV, health care providers, and the elderly. One obvious advantage is the safety factor associated with the lack of infectivity. As another potential advantage, a noninfectious subunit vaccine would be more stable in storage and handling than an infectious viral vaccine. Although purified subunit vaccines have been associated with immunopathologic complications in experimental animals (Murphy et al., *Vaccine* 8:497–502,1990, incorporated herein by reference), this appears to occur only in situations where there has not been prior exposure to RSV antigen (Graham et al., *J. Immun.* 151:2032–2040, 1993, incorporated herein by reference). Thus, a subunit vaccine would be considered appropriate for seropositive individuals. Furthermore, there is some controversy as to whether purified subunit vaccines actually cause immunopathologic complications in seronegative individuals (Corvaia et al., *J. Infec. Dis.* 176:560–9,1997; Plotnicky-Gilquin et al., *Virology* 258:128–40, 1999, each incorporated herein by reference). In addition, general advances in vaccine technology, such as improved adjuvants and new modes of immunization, offer the possibility to modulate immune responses to reduce adverse reactions (Oien et al., *Vaccine* 12:731–5, 1994; Tebby et al., *Viral Immunol.* 12:41–5,1999; Siegrist et al., *J. Infect. Dis.* 179:1326–33, 1999, each incorporated herein by reference). Although it is generally thought that a parenteral route of immunization would be particularly sensitive to immunosuppression due to maternally derived antibodies and hence limit the effectiveness of a subunit vaccine, there is evidence in rodents that this is not the case, and also that a parenteral immunization in the very young rodent can be highly effective (Brandt et al., *J. Infect. Dis.* 176:884–91, 1997, incorporated herein by reference). Thus, while a live attenuated RSV vaccine continues to seem to be the strategy of choice for the pediatric population, the primary target for RSV immunopropylaxis, a noninfectious subunit vaccine also likely, will have an important role, such as for immunization of certain populations as noted above.

Several sources of RSV antigens currently exist. One source is the authentic, virus-encoded proteins which are synthesized during RSV infection of tissue culture cells such as HEp-2 or Vero cells (Walsh et al., *J. Gen. Virol.* 65:761–7, 1984, and ibid, 66:409–425, 1985, incorporated herein by reference). Another source is the expression of RSV protein by recombinant vectors, of which there are numerous examples. One example is expression of individual RSV proteins in mammalian cells by recombinant vaccinia virus vectors (Elango et al., *Proc. Natl. Acad. Sci. USA* 83:1906–1910, 1986; Olmsted et al., *Proc. Natl. Acad. Sci. USA* 83:7462–7466, 1986, each incorporated herein by reference). Another example is infection of insect cells with recombinant baculovirus expressing RSV antigen, such as been described for a novel fusion protein of the F and G proteins (Wathen et al., *J. Gen. Virol.* 70:2625–35, 1989, incorporated herein by reference) as well as for complete or truncated versions of the F protein (Wathen et al., *J. Infect. Dis.* 159:255–264, 1989, incorporated herein by reference). Yet another example is expression from a recombinant vector in yeast cells (Ding et al., *Virology,* 159:450–3, 1987, incorporated herein by reference). Similarly, RSV antigens have been expressed in whole or in part in bacteria (Martin-Gallardo et al., *J. Gen. Virol.* 74:453–8, 1993; Power et al., *Virology* 230:155–66, 1997, each incorporated herein by reference). Another source of RSV antigen has been synthetic peptides, such as ones representing short linear regions of the G or F proteins (Levely et al., *Cell. Immun.* 125:65–78, 1990; Trudel et al., *Virology* 185:749–57, 1991, each incorporated herein by reference).

RSV antigens can be purified from various sources by methods well known to those skilled in the art. As a typical example, a mammalian cell line can be infected with a standard wild type strain of RSV and, at the peak of antigen accumulation, the cells can be lysed with a mild detergent, insoluble debris can be sedimented by centrifugation, and the resultant supernatant can be subjected to chromatography for the purification of viral antigen. For example, the F and G glycoproteins can be selected using immobilized monoclonal antibody against each protein, and subsequently eluted with a low pH buffer (Walsh et al., *J. Gen. Virol.* 65:761–7, 1984, and ibid, 66:409–425, 1985, each incorporated herein by reference). This can be supplemented or substituted with other well known purification procedures, such as ion exchange chromatography, reversed-phase high-performance liquid chromatography, denaturation and protein refolding, etc. (Walsh et al., *J. Gen. Virol.* 65:7617, 1984, and ibid, 66:409–425, 1985; Wells et al., *Protein Expr. Purif.* 5:391–40,1994; Falsey and Walsh, *Vaccine* 1 5:1130–1132, 1997, each incorporated herein by reference). Indeed, candidate subunit RSV vaccines have been produced by these methods using RSV-infected cells as the starting material: namely, PFP-1, an immunoaffinity-purified vaccine consisting of approximately 90–95% F protein (Tristram et al., *Vaccine* 12:551–556, 1994, incorporated herein by reference), and PFP-2, and ion exchange chromatography-purified vaccine consisting of 98% F protein (Tristram et al., *J. Infect. Dis.* 170:425–8, 1994, incorporated herein by reference).

While PFP-1 and PFP-2 are derived from cells infected with wild type RSV, the alternative approach of expression of proteins from a recombinant source has several potential advantages. A number of these advantages are listed here: the protein can be truncated to include only the portions deemed relevant or the protein can be fused to sequences which might aid in its purification, stability or immunogenicity (Power et al., *Virology* 230:155–66, 1997, incorporated herein by reference); proteins can be engineered to facilitate recovery (Wathen et al., *J. Infect. Dis.* 159:255–264, 1989, incorporated herein by reference); the protein sequence itself can be altered to improve various characteristics, such as to increase solubility (Murby et al., *Eur. J. Biochem.* 230:38–44, 1995, incorporated herein by reference) or to ablate immunopathologic reactions (Tebbey et al., *J. Exp. Med.* 188:1967–72, 1998, incorporated herein by reference); chimeric proteins can be designed for the purpose of broadening the immune response (Wathen et al., *J. Gen. Virol.* 70:2625–35, 1989, incorporated herein by reference); expression of one or more viral proteins from one or more vectors in the absence of other viral genes ensures an absence of contamination by the other viral proteins; recombinant vectors frees the experimenter from the limitations of working with RSV and offers the potential of improved expression. These are offered by means of examples and do not encompass the full range of benefits of recombinant vectors. The use of synthetic peptides includes many of these benefits and also has the potential for greater purity.

Despite the many potential benefits, the use of heterologous vectors such as baculovirus, vaccinia virus, or bacterial systems also poses complications. For example, each method introduces heterologous antigens which must be removed, especially in the case of insect or bacterial cells. Expression in insect cells can provide altered glycosylation, and expression in bacteria can yield malfolded protein lacking disulfide bonds, phosphorylation and glycosylation (Bialy, Biotechnology 5:883–890, 1987, incorporated herein by reference). Also, the promise of increased levels of expression and purity have proven to be elusive. For example, the amounts of protein expressed in cells infected with recombinant baculovirus or vaccinia virus have not been greater than that expressed in cells infected with wild type RSV. Indeed, the most promising subunit vaccines are PFP-1 and PFP-2, which are derived from mammalian cells infected with standard RSV.

A completely unanticipated aspect of the invention is that it provides an M2-2 knock out or deletion virus which can be used directly in cell culture to provide improved yield of RSV protein for isolation and purification. The M2-2 knock out and deletion viruses of the invention express levels of viral protein, including viral antigen (e.g., F and/or G protein(s)), which are increased approximately 2-fold, preferably 2 to 3-fold, up to 5-fold, 10-fold or greater compared to protein expression in wild-type or parental mutant strains, and thus provide materials for purification that are enriched in RSV protein(s). It is well known that even a modest increases in protein expression can be highly advantageous in large scale production, yielding a product of improved quantity and quality. Thus, M2-2 knock out and deletion viruses can be used directly to infect cells permissive to RSV infection and propagation, such as cultured HEp-2 or Vero cells, which can then be subjected to protein purification procedures to yield F, G or other viral proteins. Furthermore, the greater yield observed in the examples hereinbelow represents results under conditions which have not been optimized for protein expression. In other aspects of the invention, permissive cells are screened to select cells that yield the highest level of protein, and experimental conditions are further modified according to known methods to maximize the viability of the over-expressing cells and thus further improve the yield.

Furthermore, the fact that the M2-2 knock out and deletion viruses are recombinant offers further possibilities of improvement, and combines the benefits of recombinant expression with the authenticity or protein products associated with expression by RSV in permissive cells. For example, amino acids 184–198 in the G protein have been shown to be associated with priming for enhanced immunopathology in the mouse model, and has been confirmed in part with T cells from human donors (Tebbey et al., *J. Exp. Med.* 188:1967 72, 1998, incorporated herein by reference). In a second study, deletion of the overlapping domain of amino acids 193–200 ablated the capacity of G protein to induce immunopathology (Sparer et al., *J. Exp. Med.* 187:1921–6, 1998, incorporated herein by reference), confirming that this region of the G protein contains one or more epitopes associated with priming for enhanced disease. Thus, recombinant RSV has been prepared in which amino acids 187–197 are deleted (mutant 187/197) or in which this same region was deleted and amino acids 198–200 altered by amino acid substitution (mutant 187/200). Each virus replicates as efficiently in vitro as wild type RSV. Thus, the 187/197 or 187/200 mutations can be incorporated within a M2-2 knock out or deletion mutation to prepare recombinant virus which expressing increased amounts of viral proteins, and expressing a G protein which has been engineered to remove a domain associated with enhanced immunopathology.

Also within the invention, the M2-ORF 2 deletion and knock out mutant RSV can be further modified to delete the G protein gene altogether from recombinant RSV. The resulting G deletion virus replicates to low titer on HEp-2 cells, but on Vero cells replication is comparable to that of wild type virus and the G deletion virus forms plaques. Since G is not required for virus growth under these conditions, the G protein can be engineered without regard for whether or not this affects its function. Thus, it is possible to make changes to improve or alter immunogenicity, solubility, reactogenicity, or any other feature. The resulting recombinant virus can then be used to infect cells for the expression of viral antigen. In addition, it has been found that other attenuated RSV mutants, for example the cpts248/404 mutant also exhibit increased levels of protein synthesis. Thus, incorporation of one or more additional attenuating mutations that specify increased protein synthesis, for example a mutation adopted from cpts248/404, into an M2-2 knock out or deletion mutant of the invention will provide additional advantages in terms of increased protein expression.

To generate infectious RSV incorporating M2-ORF 2 deletion or knock out mutations, isolated polynucleotides (e.g., cDNA) encoding the M2 ORF2 deletion and knock out mutant RSV genome or antigenome are expressed, separately, or in cis, including expression from the antigenome or genome cDNA, with the N, P, L and M2(ORF1) proteins. These polynucleotides are inserted by transfection, electroporation, mechanical insertion, transduction or the like, into cells which are capable of supporting a productive RSV infection, e.g., HEp-2, FRhL-DBS2, MRC, and Vero cells. Transfection of isolated polynucleotide sequences may be introduced into cultured cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), DEAE-dextran mediated transfection (Ausubel et al., (ed.) *Current Protocols in Molecular Biology,* John Wiley and Sons, Inc., NY, 1987, cationic lipid-mediated transfection (Hawley-Nelson et al., *Focus* 15:73–79, 1993) or a commercially available transfection regent, e.g., LipofectACE® (Life Technologies) (each of the foregoing references are incorporated herein by reference).

The N, P, L and M2(ORF1) proteins are encoded by one or more cDNAs and expression vectors which can be the same or separate from that which encodes the genome or antigenome, and various combinations thereof. Furthermore, one or more proteins, and particularly the M2-1 protein, can be supplied directly from the antigenome or genome (Collins et al., *Virology* 259:251–258, 1999, incorporated herein by reference). Additional proteins may be included as desired, encoded by its own vector or by a vector encoding a N, P, L, or M2(ORF1) protein and/or the complete genome or anti genome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., *Virology,* 210:202–205, 1995, incorporated herein by reference). The viral proteins, and/or T7 RNA polymerase, can also be provided from transformed mammalian cells, or by transfection of preformed mRNA or protein.

Alternatively, synthesis of antigenome or genome can be conducted in vitro (cell-free) in a combined transcription-translation reaction, followed by transfection into cells. Or, antigenome or genome RNA can be synthesized in vitro and transfected into cells expressing RSV proteins.

To select candidate vaccine viruses according to the invention, the criteria of viability, attenuation and immunogenicity are determined according to well known methods. Viruses which will be most desired in vaccines of the invention must maintain viability, have a stable attenuation phenotype, exhibit replication in an immunized host (albeit at lower levels), and effectively elicit production of an immune response in a vaccinee sufficient to confer protection against serious disease caused by subsequent infection from wild-type virus. Clearly, the heretofore known and reported RS virus mutants do not meet all of these criteria. Indeed, contrary to expectations based on the results reported for known attenuated RSV, viruses of the invention are not only viable and more appropriately attenuated than previous mutants, but are more stable genetically in vivo than those previously studied mutants—retaining the ability to stimulate a protective immune response and in some instances to expand the protection afforded by multiple modifications, e.g., induce protection against different viral strains or subgroups, or protection by a different immunologic basis, e.g., secretory versus serum immunoglobulins, cellular immunity, and the like. Prior to the invention, genetic instability of the ts phenotype following replication in vivo has been common for ts viruses (Murphy et al., *Infect. Immun.* 37:235–242, 1982).

To propagate an M2 ORF2 deletion and knock out mutants RSV virus for vaccine use and other purposes, a number of cell lines which allow for RSV growth may be used. RSV grows in a variety of human and animal cells. Preferred cell lines for propagating attenuated RS virus for vaccine use include DBS-FRhL-2, MRC-5, and Vero cells. Highest virus yields are usually achieved with epithelial cell lines such as Vero cells. Cells are typically inoculated with virus at a multiplicity of infection ranging from about 0.001 to 1.0 or more, and are cultivated under conditions permissive for replication of the virus, e.g., at about 30–37° C. and for about 3–5 days, or as long as necessary for virus to reach an adequate titer. Virus is removed from cell culture and separated from cellular components, typically by well known clarification procedures, e.g., centrifugation, and may be further purified as desired using procedures well known to those skilled in the art.

M2 ORF2 deletion and knock out RSV mutants which has been satisfactorily attenuated and otherwise modified as described herein can be tested in various well known and generally accepted in vitro and in vivo models to confirm adequate attenuation, resistance to phenotypic reversion, and immunogenicity for vaccine use. In in vitro assays, the modified virus (e.g., a multiply attenuated, biologically derived or recombinant RSV) is tested for temperature sensitivity of virus replication, i.e. ts phenotype, and for the small plaque phenotype. Modified viruses are further tested in animal models of RSV infection. A variety of animal models have been described and are summarized in (Meignier et al., eds., Animal Models of Respiratory Syncytial Virus Infection, Merieux Foundation Publication, 1991, which is incorporated herein by reference). A cotton rat model of RSV infection is described in (U.S. Pat. No. 4,800,078 and Prince et al., *Virus Res.* 3:193–206, 1985), which are incorporated herein by reference, and is considered predictive of attenuation and efficacy in humans and non-human primates. In addition, a primate model of RSV infection using the chimpanzee is predictive of attenuation and efficacy in humans, as is described in detail in (Richardson et al., *J. Med. Virol.* 3:91–100, 1978; Wright et al., *Infect. Immun.* 37:397–400, 1982; Crowe et al., *Vaccine* 11:1395–1404, 1993, each incorporated herein by reference).

RSV model systems, including rodents and chimpanzees for evaluating attenuation and infectivity of RSV vaccine candidates are widely accepted in the art and the data obtained therefrom correlate well with RSV infection and attenuation. The mouse and cotton rat models are especially useful in those instances in which candidate RSV viruses display inadequate growth in chimpanzees, for example in the case of RSV subgroup B viruses.

In accordance with the foregoing description and based on the Examples below, the invention also provides isolated, infectious M2 ORF2 deletion and knock out mutant RSV compositions for vaccine use. The attenuated virus which is a component of a vaccine is in an isolated and typically purified form. By isolated is meant to refer to RSV which is in other than a native environment of a wild-type virus, such as the nasopharynx of an infected individual. More generally, isolated is meant to include the attenuated virus as a component of a cell culture or other artificial medium where it can be propagated and characterized in a controlled setting. For example, attenuated RSV of the invention may be produced by an infected cell culture, separated from the cell culture and added to a stabilizer.

RSV vaccines of the invention contain as an active ingredient an immunogenically effective amount of RSV produced as described herein. Biologically derived or recombinant RSV can be used directly in vaccine formulations, or lyophilized. Lyophilized virus will typically be maintained at about 4° C. When ready for use the lyophilized virus is reconstituted in a stabilizing solution, e.g., saline, SPG, Mg++ and HEPES, with or without adjuvant, as further described below. The recombinantly modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

Acceptable adjuvants include incomplete Freund's adjuvant, aluminum phosphate, aluminum hydroxide, or alum, which are materials well known in the art. Preferred adjuvants also include Stimulon® QS-21 (Aquila Biopharmaceuticals, Inc., Farmingham, Mass.), MPL® (3-0-deacylated monophosphoryl lipid A; RIBI ImmunoChem Research, Inc., Hamilton, Mont.), and interleukin-12 (Genetics Institute, Cambridge, Mass.).

Upon immunization with an M2 ORF2 deletion and knock out mutant RSV vaccine composition as described herein, via aerosol, droplet, oral, topical or other route, the immune system of the host responds to the vaccine by producing antibodies specific for one or more RSV virus proteins, e.g., F and/or G glycoproteins. As a result of the vaccination the host becomes at least partially or completely immune to RSV infection, or resistant to developing moderate or severe RSV disease, particularly of the lower respiratory tract.

M2 ORF2 deletion and knock out mutant RSV vaccines of the invention may comprise attenuated virus that elicits an immune response against a single RSV strain or antigenic subgroup, e.g. A or B, or against multiple RSV strains or subgroups. In this context, the RSV can elicit a monospecific immune response or a polyspecific immune response against multiple RSV strains or subgroups. Alternatively, RSV having different immunogenic characteristics can be combined in a vaccine mixture or administered separately in a coordinated treatment protocol to elicit more effective protection against one RSV strain, or against multiple RSV strains or subgroups.

The host to which the vaccine is administered can be any mammal susceptible to infection by RSV or a closely related virus and capable of generating a protective immune response to antigens of the vaccinizing virus. Thus, suitable hosts include humans, non-human primates, bovine, equine, swine, ovine, caprine, lagamorph, rodents, etc. Accordingly, the invention provides methods for creating vaccines for a variety of human and veterinary uses.

The vaccine compositions containing the attenuated M2 ORF2 deletion and knock out mutant RSV of the invention are administered to a patient susceptible to or otherwise at risk of RSV infection in an "immunogenically effective dose" which is sufficient to induce or enhance the individual's immune response capabilities against RSV. In the case of human subjects, the attenuated virus of the invention is administered according to well established human RSV vaccine protocols, as described in, e.g., (Wright et al., *Infect. Immun.* 37:397–400, 1982; Kim et al., *Pediatrics* 52:56–63, 1973; and Wright et al., *J. Pediatr.* 88:931–936, 1976), which are each incorporated herein by reference. Briefly, adults or children are inoculated intranasally via droplet with an immunogenically effective dose of RSV vaccine, typically in a volume of 0.5 ml of a physiologically acceptable diluent or carrier. This has the advantage of simplicity and safety compared to parenteral immunization with a non-replicating vaccine. It also provides direct stimulation of local respiratory tract immunity, which plays a major role in resistance to RSV. Further, this mode of vaccination effectively bypasses the immunosuppressive effects of RSV-specific maternally-derived serum antibodies, which typically are found in the very young. Also, while the parenteral administration of RSV antigens can sometimes be associated with immunopathologic complications, this has never been observed with a live virus.

In all subjects, the precise amount of M2 ORF2 deletion and knock out mutant RSV vaccine administered and the timing and repetition of administration will be determined based on the patient's state of health and weight, the mode of administration, the nature of the formulation, etc. Dosages will generally range from about $10^3$ to about $10^6$ plaque forming units (PFU) or more, e.g., $10^7$ to $10^8$ PFU of virus per patient, more commonly from about $10^4$ to $10^5$ PFU virus per patient. In any event, the vaccine formulations should provide a quantity of attenuated RSV of the invention sufficient to effectively stimulate or induce an anti-RSV immune response, e.g., as can be determined by complement fixation, plaque neutralization, and/or enzyme-linked immunosorbent assay, among other methods. In this regard, individuals are also monitored for signs and symptoms of upper respiratory illness. As with administration to chimpanzees, the attenuated virus of the vaccine grows in the nasopharynx of vaccinees at levels approximately 10-fold or more lower than wild-type virus, or approximately 10-fold or more lower when compared to levels of incompletely attenuated RSV.

In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) RSV infection. Similarly, adults who are particularly susceptible to repeated or serious RSV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered RSV strain expressing a cytokine or an additional protein rich in T cell epitopes may be particularly advantageous for adults rather than for infants. Alternatively, a lower level of attenuation may be selected for older vaccinees. RSV vaccines produced in accordance with the present invention can be combined with viruses expressing antigens of another subgroup or strain of RSV to achieve protection against multiple RSV subgroups or strains. Alternatively, the vaccine virus may incorporate protective epitopes of multiple RSV strains or subgroups engineered into one RSV clone as described herein.

Typically when different vaccine viruses are used they will be administered in an admixture simultaneously, but they may also be administered separately. For example, as the F glycoproteins of the two RSV subgroups differ by only about 10% in amino acid sequence, this similarity is the basis for a cross-protective immune response as observed in animals immunized with RSV or F antigen and challenged with a heterologous strain. Thus, immunization with one strain may protect against different strains of the same or different subgroup. However, optimal protection probably will require immunization against both subgroups.

The M2 ORF2 deletion and knock out mutant RSV vaccines of the invention elicit production of an immune response that is protective against serious lower respiratory tract disease, such as pneumonia and bronchiolitis when the individual is subsequently infected with wild-type RSV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

Preferred M2 ORF2 deletion and knock out mutants of the present invention exhibit a very substantial diminution of virulence when compared to wild-type virus that is circulating naturally in humans. The virus is sufficiently attenuated so that symptoms of infection will not occur in most immunized individuals. In some instances the attenuated virus may still be capable of dissemination to unvaccinated individuals. However, its virulence is sufficiently abrogated such that severe lower respiratory tract infections in the vaccinated or incidental host do not occur.

The level of attenuation of M2 ORF2 deletion and knock out mutants may be determined by, for example, quantifying the amount of virus present in the respiratory tract of an immunized host and comparing the amount to that produced by wild-type RSV or other attenuated RSV which have been evaluated as candidate vaccine strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold or more less. Also, the level of replication of the attenuated RSV vaccine strain in the upper respiratory tract of the chimpanzee should be less than that of the RSV A2 ts-1 mutant, which was demonstrated previously to be incompletely attenuated in seronegative human infants. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of RSV in the nasopharynx of an infected host are well known in the literature. Specimens are obtained by aspiration or washing out of nasopharyngeal secretions and virus quantified in tissue culture or other by laboratory procedure. See, for example, (Belshe et al., *J. Med. Virology* 1:1 57–162, 1977; Friedewald et al., *J. Amer. Med. Assoc.* 204:690–694, 1968; Gharpure et al., *J. Virol.* 3:414–421, 1969; and Wright et al., *Arch. Ges. Virusforsch.* 41:238–247, 1973), each incorporated herein by reference. The virus can conveniently be measured in the nasopharynx of host animals, such as chimpanzees.

In some instances it may be desirable to combine the M2 ORF2 deletion and knock out mutant RSV vaccines of the invention with vaccines which induce protective responses to other agents, particularly other childhood viruses. For example, a chimeric RSV vaccine of the present invention can be administered simultaneously with PIV vaccine, such as described in Clements et al., *J. Clin. Microbiol.* 29:1175–1182, 1991, incorporated herein by reference. In another aspect of the invention the chimeric RSV can be employed as a vector for protective antigens of other respiratory tract pathogens, such as PIV, by incorporating the sequences encoding those protective antigens into the RSV genome or antigenome which is used to produce infectious RSV, as described herein.

In yet another aspect of the invention an M2 ORF2 deletion or knock out mutant RSV is employed as a vector for transient gene therapy of the respiratory tract. According to this embodiment the M2 ORF2 deletion and knock out mutant RSV genome or antigenome incorporates a sequence which is capable of encoding a gene product of interest. The gene product of interest is under control of the same or a different promoter from that which controls RSV expression. The infectious RSV produced by coexpressing the recombinant RSV genome or antigenome with the N, P, L and M2(ORF1) proteins and containing a sequence encoding the gene product of interest is administered to a patient. This can involve a recombinant RSV which is fully infectious (i.e., competent to infect cultured cells and produce infectious progeny), or can be a recombinant RSV which, for example, lacks one or more of the G, F and SH surface glycoprotein genes and is propagated in cells which provide one or more of these proteins in trans by stable or transient expression. In such a case, the recombinant virus produced would be competent for efficient infection, but would be highly inefficient in producing infectious particles. The lack of expressed cell surface glycoproteins also would reduce the efficiency of the host immune system in eliminating the infected cells. These features would increase the durability and safety of expression of the foreign gene.

With regard to gene therapy, administration is typically by aerosol, nebulizer, or other topical application to the respiratory tract of the patient being treated. M2 ORF2 deletion and knock out mutant RSV is administered in an amount sufficient to result in the expression of therapeutic or prophylactic levels of the desired gene product. Examples of representative gene products which are administered in this method include those which encode, for example, those particularly suitable for transient expression, e.g., interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

The following examples are provided by way of illustration, not limitation. In brief, these examples describe a surprising transcription/replication "switch" function of the 90-amino acid M2-2 protein, whose function was heretofore unknown. Viable recombinant RSV was recovered in which expression of M2-2 was ablated, identifying it as an accessory factor dispensable for growth in cell culture. Virus lacking a functional M2-2 protein grew less efficiently than did the wild type parent in cell culture, with titers that were reduced 1000-fold during the initial 2–5 days and 10-fold by days 7–8. In cells infected with M2-2 knock-out virus, the accumulation of genomic RNA, was approximately 15–18% that of wild type, while the accumulation of mRNA was approximately 175 to 300% that of wild type. Synthesis of the F and G glycoproteins, the major RSV neutralization and protective antigens, was increased in proportion with the mRNA increase. In cells infected with wild type RSV, mRNA accumulation increased dramatically up to approximately 12–15 hours post-infection and then leveled off, whereas accumulation continued to increase in cells infected with the M2-2 knock-out viruses. These findings suggest that M2-2 mediates a regulatory from transcription to RNA replication, one which provides an initial high level of mRNA synthesis followed by a shift in the RNA synthetic program in favor of genomic RNA for virion assembly. For the purpose of vaccine development within the present invention, this represents a highly desirable phenotype in which virus growth is attenuated while gene expression is undiminished or, more typically, concomitantly increased. This is an unexpected and highly desirable phenotype for vaccine development, since attenuating mutations described to date typically are associated with a decrease in antigen expression and a concomitant decrease in immunogenicity.

EXAMPLE I

M2-2 Mutant Plasmid Constructions

All recombinant RSV viruses and cDNA clones were based on RSV strain A2 of antigenic subgroup A. An 805 bp MscI-BamHI fragment (nt 7696–8501 in the complete recombinant antigenomic sequence) containing most of M2 ORF1 and all of ORF2 was subcloned and subjected to mutagenesis. A unique NdeI site in ORF2 was opened, filled-in, and relegated, creating a frame-shift mutation hereafter called the NdeI mutation (FIG. 1B). The NdeI restriction enzyme site within ORF2 was identified at genome position 8299, and the frame-shift mutation (2 nts added) was at codon 47 of the predicted 90 amino acid protein (FIG. 1B). Thus the NdeI mutant encoded the N-terminal 46 amino acids of M2-2 fused to the 18 heterologous amino acids encoded by the frame-shift.

To create a second M2-2 knock-out mutant, hereafter called the K5 mutant (rA2-K5, also referred to as rA2ΔM2-2), PCR mutagenesis (Byrappa et al., *Genome Research* 5:404–407, 1995, incorporated herein by reference) was carried out on the subcloned MscI-BamHI fragment. This mutagenesis was designed to completely ablate expression of ORF2, by mutation of each of the three potential initiation codons for ORF2 (FIGS. 1A and 1C) into ACG codons. To minimize the possibility of reversion or non-AUG initiation (Curran et al., *Embo J.* 7:245–51, 1988; *Mol. Cell. Biol.* 18:5021–31, 1998, each incorporated herein by reference), a stop codon was also added in each register following the ORF1 termination codon, terminating M2 ORF2 at codon 13 (FIG. 1C). The M2-1 amino acid sequence was not affected in either mutant.

The mutagenic oligonucleotides, which were 5'-phosphorylated, were as follows:

forward primer 5'-TAATTAATTAAGTATAACTTCCATAC-
TAATAACAAG-3' (nt 8195–8231)        (SEQ ID NO. 1)

reverse primer 5'-TCAGGTAGTATCGTTATTTTGGCGTG-
GTCGTTTGT-3' (nt 8156–8191)         (SEQ ID NO. 2)

The presence of the NdeI and K5 mutations in their respective cDNAs was confirmed by sequencing, and each was sub-cloned into the AflII/BamHI sites of the support plasmid pTM-M2, which encodes both M2 ORFs and was used previously to supply both M2-1 and M2-2 proteins in a model minigenome system (Collins et al., *Proc. Nat. Acad. Sci. USA* 93:81–5, 1996, incorporated herein by reference). The same fragment was also cloned into the AflII/BamHI sites of pUC118-FM2, which contained the F and M2 genes, and the StuI/BamHI fragment of this plasmid was subsequently transferred to the full-length antigenomic cDNA (D53) to create NdeI and K5 antigenomic cDNAs.

EXAMPLE II

Effects of M2-2 Knock-out Mutations on Minireplicon Transcription and Replication The function(s) of the M2-2 protein was not known, but it had previously been shown to strongly inhibit minigenome RNA synthesis (Collins et al., *Proc. Nat. Acad. Sci. USA* 93:81–5, 1996; Grosfeld et al., *J. Virol.* 69:5677–86, 1995 Hardy et al., *J. Virol.* 72:520–6, 1998, each incorporated herein by reference). Therefore this highly sensitive assay was used to verify that the NdeI and K5 mutations ablated this inhibitory effect. RSV transcription and replication were studied using a negative-sense RSV-CAT minigenome C2, which contains the CAT ORF under the control of RSV GS and GE signals flanked by the 3'-leader and 5'-trailer regions of the RSV genome (Collins et al., *Proc. Nat. Acad. Sci. USA* 93:81–5, 1996; Grosfeld et al., *J. Virol.* 69:5677–86, 1995). Intracellular synthesis of the C2 minigenome was driven from the transfected plasmid by T7 RNA polymerase supplied from the recombinant vaccinia virus vTF7-3 (Fuerst et al., *Proc. Nat. Acad. Sci. USA* 83:8122–8126, 1986), and RSV proteins were expressed from cotransfected support plasmids.

Figure 2:
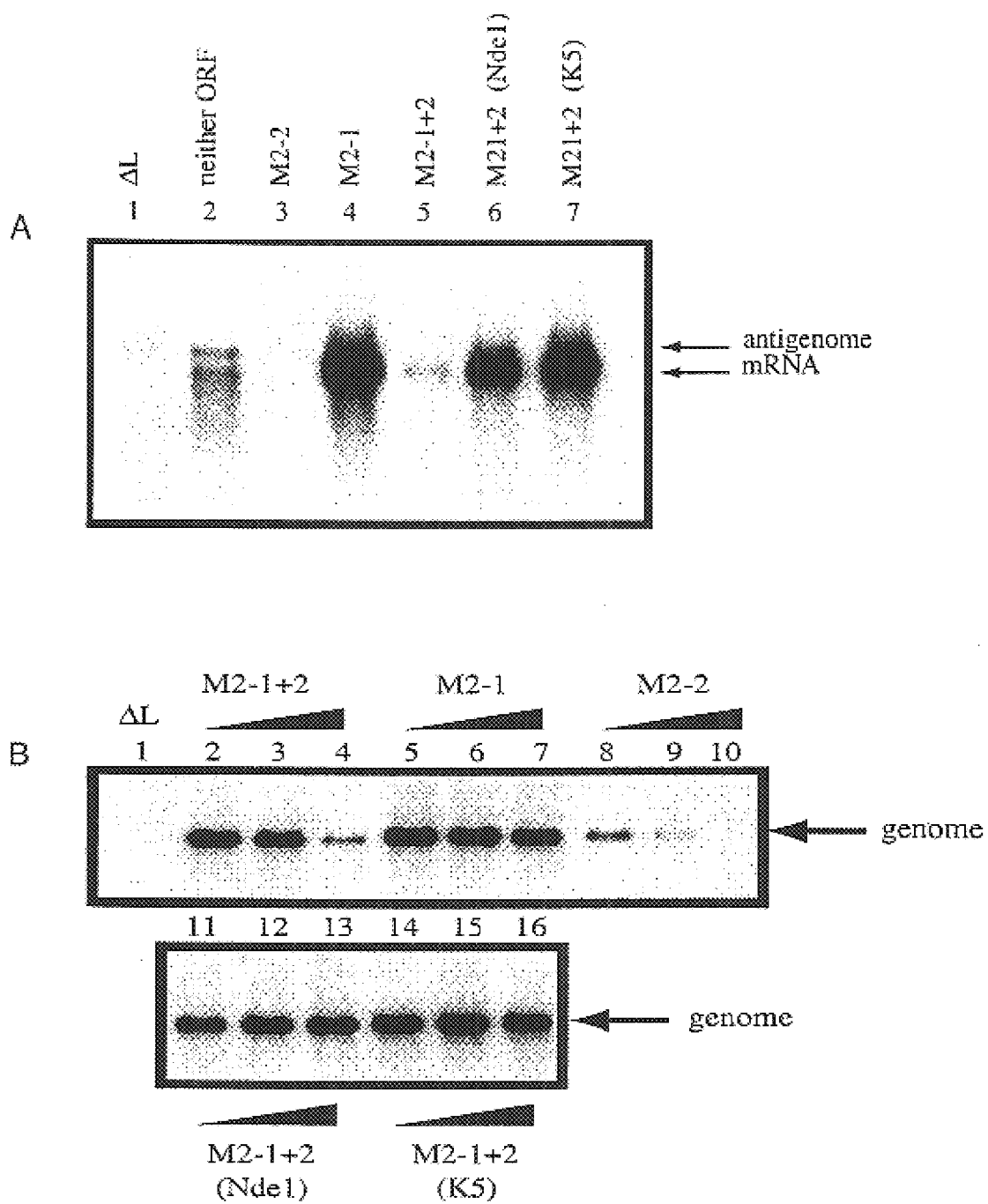
FIG. 2 demonstrates that the NdeI and K5 mutations each ablate the inhibitory function of M2-2 in a reconstituted minigenome system. In panel A, HEp-2 cells were simultaneously infected with vTF7-3 (5 plaque forming units per cell) and transfected with plasmid encoding the negative-sense C2 minigenome cDNA (200 ng) and support plasmids (N, 400 ng; P, 200 ng; L, 100 ng) per well of a 6-well dish and supplemented with pTM constructs (80 ng) containing no insert (lane 2), M2 ORF 1 (lane 4), M2 ORF 2 (lane 3), M2 ORFs 1+2 (lane 5) or the M2 ORFs 1+2 containing the NdeI (lane 6) or K5 (lane 7) mutations. Lane 1 is a negative control lacking L. Cells were exposed to 2 μg actinomycin D per ml from 24–26 h post-infection (Feams et al., *Virology* 236, 188–201, 1997, incorporated herein by reference). At 48 h post-infection, total intracellular RNA was isolated and electrophoresed on formaldehyde gels for Northern blot analysis (Grosfeld et al., *J. Virol.* 69:5677–86, 1995, incorporated herein by reference). Blots were hybridized to a negative-sense CAT specific riboprobe to detect both mRNA and antigenome. In panel B: HEp-2 cells were transfected as described below with plasmid encoding positive-sense C4 mini-antigenome complemented by the N, P and L plasmids as in Panel A. The transfection mixtures were supplemented with increasing amounts (0.008, 0.04 and 0.2 times the relative molar ratio of transfected pTM-N) of pTM constructs encoding M2 ORFs 1+2 (lanes 2, 3 and 4), M2 ORF 1 (lanes 4, 5 and 6), M2 ORF 2 (lanes 8, 9 and 10) or ORFs 1+2 containing the NdeI (lanes 11, 12 and 13) or K5 (lanes 14, 15 and 16) mutation. Total intracellular RNA was analyzed by Northern blots hybridized with a positive-sense CAT specific riboprobe to detect genomic RNA.

When minigenome C2 was complemented by N, P and L alone, it directed the synthesis of antigenome and CAT mRNA (FIG. 2A, lane 2), with the latter being mostly prematurely terminated as observed previously (Collins et al., *Proc. Nat. Acad. Sci. USA* 93:81–5, 1996; Grosfeld et al., *J. Virol.* 69:5677–86, 1995). When plasmid expressing M2-1 was added in addition, CAT mRNA was synthesized as full-length molecules (FIG. 2A, lane 4). Coexpression of M2-2 instead of M2-1 strongly inhibited the synthesis of antigenome and mRNA (FIG. 2A, compare lanes 1 and 3). When the M2 plasmid contained both ORF1 and ORF2 in their native configuration, M2-1+2, there was a significant reduction in transcription and replication products compared to that seen with M2-1, showing that the inhibitory activity of M2-2 predominated at this particular plasmid concentration (compare FIG. 2A, lanes 4 and 5). In contrast, M2-1+2 containing the NdeI or the K5 mutation behaved similarly to M2-1 alone, indicating that the inhibitory activity of M2-2 had been ablated without affecting M2-1 (compare FIG. 2A, lanes 6 and 7 with lane 4).

Comparable results were obtained when the C2 plasmid was replaced by the C4 plasmid, which expresses a positive-sense RNA representing the antigenomic replicative intermediate of the C2 minigenome (Collins et al., *Proc. Nat. Acad. Sci. USA* 93:81–5, 1996; Grosfeld et al., *J. Virol.* 69:5677–86, 1995). In this case, Northern blots were analyzed with a positive-sense riboprobe to detect the synthesis of minigenome. Cotransfection of increasing amounts of M2-1 plasmid (0.008, 0.04 and 0.2 times the relative molar amount of N plasmid) had no effect on the synthesis of minigenome (FIG. 2B, lanes 5, 6 and 7) consistent with previous findings that it does not affect replication (Collins et al., *Proc. Nat. Acad. Sci. USA* 93:81–5, 1996). However, increasing amounts of M2-2 alone or M2-1+2 led to a progressive reduction in the amounts of minigenome (FIG. 2B, lanes 8, 9 and 10 and lanes 2, 3 and 4), reflecting the inhibitory activity of M2-2. In contrast, increasing amounts of M2-1+2 containing either the NdeI and the K5 mutant did not detectably inhibit minigenome synthesis (FIG. 2B, lanes 11, 12 and 13 for the NdeI mutant, and lanes 14, 15 and 16 for the K5 mutant), indicating that neither mutant expressed an M2-2 protein active in this function.

EXAMPLE III

Recovery and Growth In vitro of M2 ORF 2 Mutant RSV

The NdeI and K5 mutations were individually incorporated into a full length antigenomic cDNA and recovery of infectious rRSV was performed as described previously (Collins et al., *Proc. Natl. Acad. Sci. USA* 92:11563–11567, 1995, incorporated herein by reference). Viruses containing either the NdeI or K5 mutations (rA2-NdeI and rA2-K5 respectively) were recovered successfully, and the presence of the mutations was confirmed by sequencing RT-PCR product generated from infected cell RNA. Thus, M2-2 is an accessory protein that is not required for RSV growth in cell culture.

Figure 3:
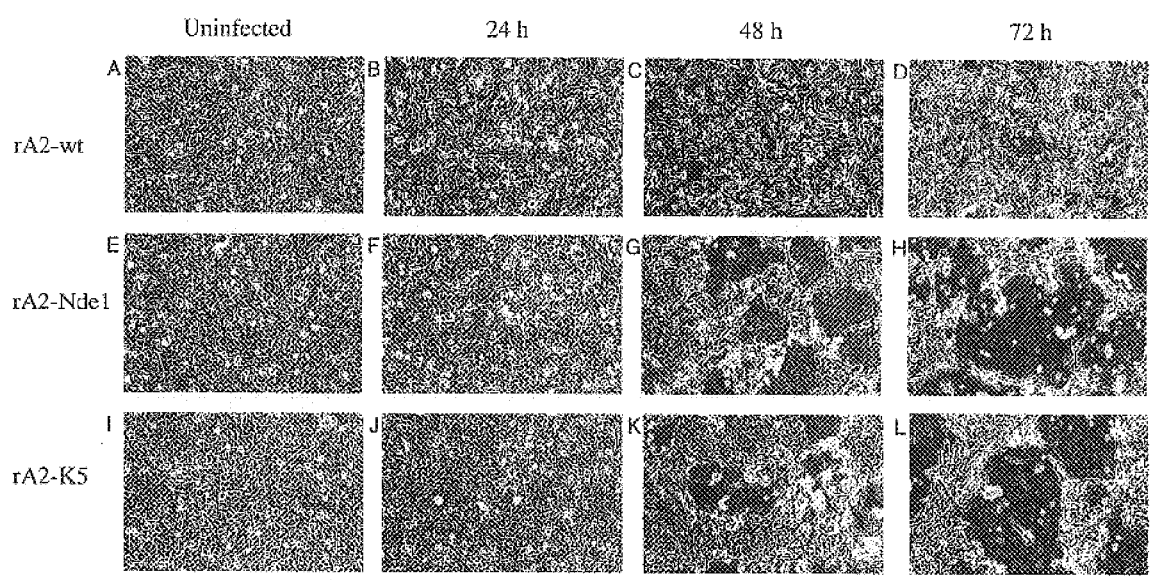
FIG. 3 illustrates cytopathogenicity of the rA2-NdeI and rA2-K5 (also referred to as rA2ΔM2-2), viruses compared to rA2-wt. HEp-2 cells were infected at a moi of 1 with the indicated virus, or mock-infected, incubated for the indicated time, and photographed at 10× magnification. The 48 h micrographs are darker due to a difference in exposure. Large syncytia are obvious in the two mutant viruses at 48 and 72 h, and smaller ones are evident at 24 h and in rA2-wt-infected cells at the same three time points.

The rA2-NdeI and rA2-K5 viruses displayed a large plaque phenotype and accelerated syncytium formation. Specifically, the plaques which formed after 3 days were large and syncytial and resembled those formed by the wt virus at day 6 post-infection (not shown). When cell monolayers were infected at an moi of 1 pfu per cell, syncytium formation was evident by 24 h and was extensive by 48 h (FIG. 3), resembling those formed by the wt virus at day 4 post-infection. These phenotypic changes suggest that the mutant viruses are either more fusogenic or have altered kinetics of growth or gene expression, or a combination of these phenotypic changes, compared to the parental strain.

Figure 4:
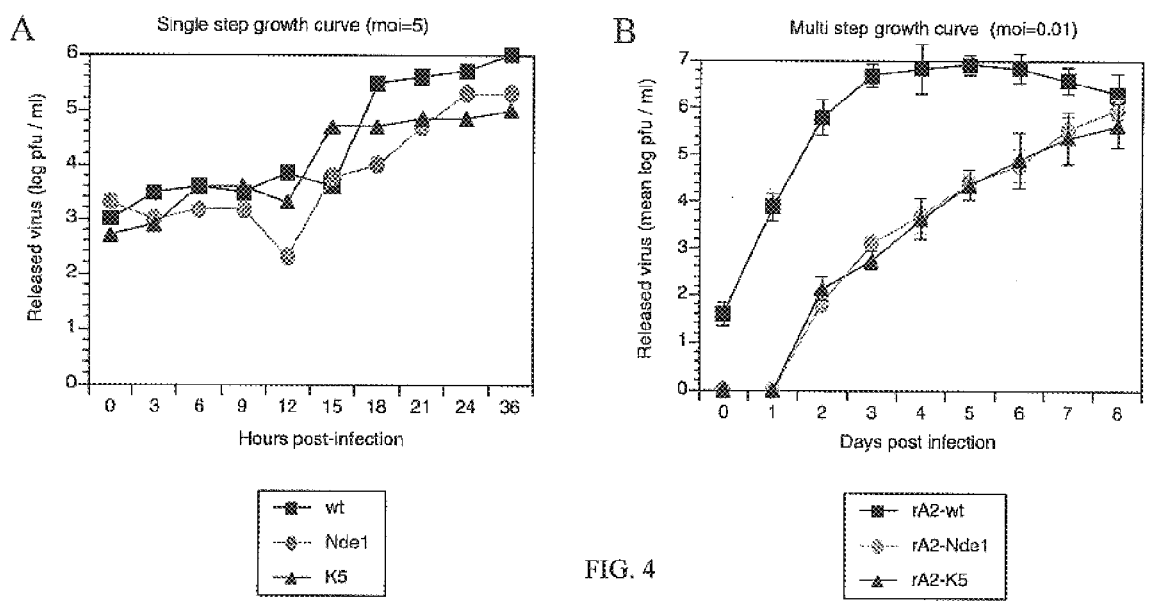
FIG. 4 illustrates kinetics of growth of rA2-wt, rA2-NdeI and rA2-KS in cell culture. Panel A shows single step growth kinetics. HEp-2 cells were infected with rA2-wt, rA2-NdeI or rA2-K5 at an moi of 5 pfu per cell and the entire medium overlay was harvested at the indicated times post-infection and flash-frozen. Viral titers were determined by plaque assay. Panel B shows multi-cycle growth kinetics. HEp-2 cells were infected in triplicate at an moi of 0.01 pfu per cell with the above viruses. At the indicated times post-infection, the entire medium overlay was removed, flash-frozen, and replaced with fresh medium. Mean virus titers determined by plaque assay (with error bars) are shown.

To examine single-cycle growth kinetics, monolayers of HEp-2 cells were infected with rA2-wt, rA2-NdeI or rA2-K5 at an moi of 5 pfu per cell (FIG. 4A). Both the rA2-NdeI and rA2-K5 recombinant viruses displayed slightly reduced growth kinetics compared to wt, with the final virus titers being approximately 10-fold less. To accentuate any potential differences, multi-step growth cycles were evaluated in HEp-2 cells infected in triplicate at an moi of 0.01 pfu per cell (FIG. 4B). In cells infected with rA2-wt virus, peak virus titers were reached at 4–5 days post infection whereupon they leveled and began to decline. This might be due to increased cytopathogenicity, which became evident for the wt after day 6 and was more pronounced than for the mutants. Both of the mutant viruses had markedly delayed and reduced growth kinetics during the first few days of incubation (1000-fold less mutant virus released compared to wt at days 2, 3 and 4 post-infection), but by day 8 post-infection the titers approached those of the parental strain. However, the maximum titers of the two mutants were consistently 10-fold lower than that of wt. These results show that the large plaque morphology exhibited by the mutant viruses was not associated with increased virus release when compared to the parental strain.

Northern Blot Analysis of Viral RNAs

Figure 5:
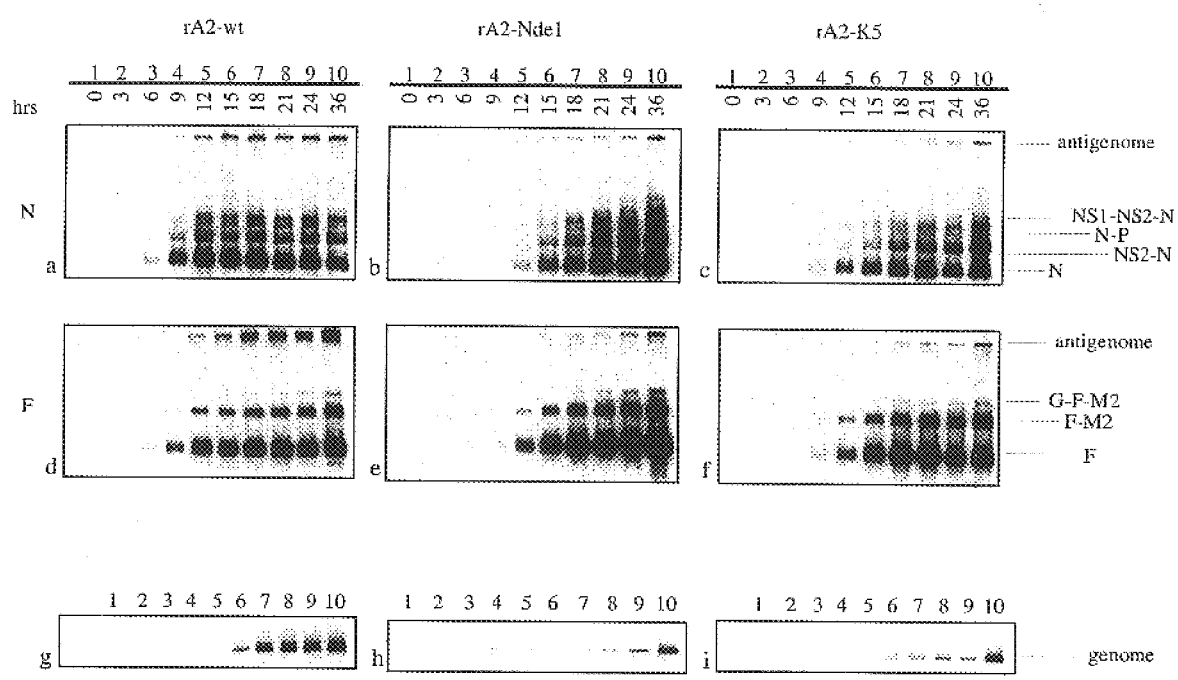
FIG. 5 provides a Northern blot analysis of RNA replication and transcription. HEp-2 cells infected with rA2-wt (a, d and g), rA2-NdeI (b, e and h) and rA2-K5 (c, f and i) were harvested at 3 h intervals (lanes 1–10) from the single cycle growth curve described in FIG. 4A, and total intracellular RNA was isolated and subjected to Northern blot analysis. Blots were hybridized with a negative-sense N specific riboprobe (a, b and c), a negative-sense F specific riboprobe (d, e and f) or a positive-sense F specific riboprobe (g, h and i). Monocistronic mRNA (i.e. N or F), polycistronic read through mRNAs (i.e. NS 1-NS2-N and G-F-M2), antigenome and genome are indicated.

RNA replication and transcription by the M2-2 mutant viruses were examined. In the single step growth experiment described above, cell monolayers from replicate plates were harvested at 3 h intervals, and total intracellular RNA was analyzed by Northern blot hybridization. The accumulation of antigenome and mRNAs was monitored by hybridization with negative-sense riboprobes against the N gene (FIG. 5 Panels a, b and c) or the F gene (Panels d, e and f). The pattern of monocistronic, dicistronic and tricistronic mRNAs produced by the mutant viruses was qualitatively similar to that of the wt strain. This suggests that ablation of the expression of M2-2 did not grossly alter the transcription antitermination effect of M2-1. The accumulation of mRNA and antigenome in the cells infected with the rA2-wt virus was first detected at 6 h post-infection (FIG. 5, panels a and d, lane 3) and increased rapidly to approximately 12–15 h post-infection, and thereafter increased more slowly or plateaued (FIG. 5, panels a and d, lanes 5–10). In contrast, both the rA2-NdeI and rA2-K5 viruses displayed a marked delay in the synthesis of mRNA and antigenome, such that these RNAs became detectable at 9–12 hours post-infection (FIG. 5, panels b and e, lanes 4 and 5 for rA2-NdeI, panels c and f, lanes 4–5 for rA2-KS). The mRNA levels then increased to levels surpassing those of wt. In contrast the accumulation of antigenome was considerably reduced compared to wt (FIG. 5, panels b and e, lanes 7–10 for rA2-NdeI, and panels c and f, lanes 7–10 for rA2-K5). For example, phosphorimager analysis of the blots probed with the negative-sense F riboprobe (FIG. 5, panels d, e and f) revealed a 1.3- to 2.0-fold increase in accumulated mRNA by 24 h post-infection, with a simultaneous three-fold reduction in the accumulation of antigenomic RNA.

RNA replication was further examined by hybridization of replicate blots with a positive-sense F riboprobe, which detected the accumulation of genomic RNA (FIG. 5, Panels g, h and i). Phosphoimager analysis indicated that the accumulation of genome by the mutant viruses was 15–18% that of the parental virus at 24 h. This reduction in genomic RNA template was unexpected given the increase the accumulation of MRNA mentioned above. Overall, the molar ratio of mRNA to genome was approximately 7- to 18-fold greater in the mutant viruses. This provides evidence for a regulatory balance between transcription and RNA replication, one which swings in favor of transcription when expression of the M2-2 protein is ablated.

Increased Expression of Major Viral Antigens

Figure 6:
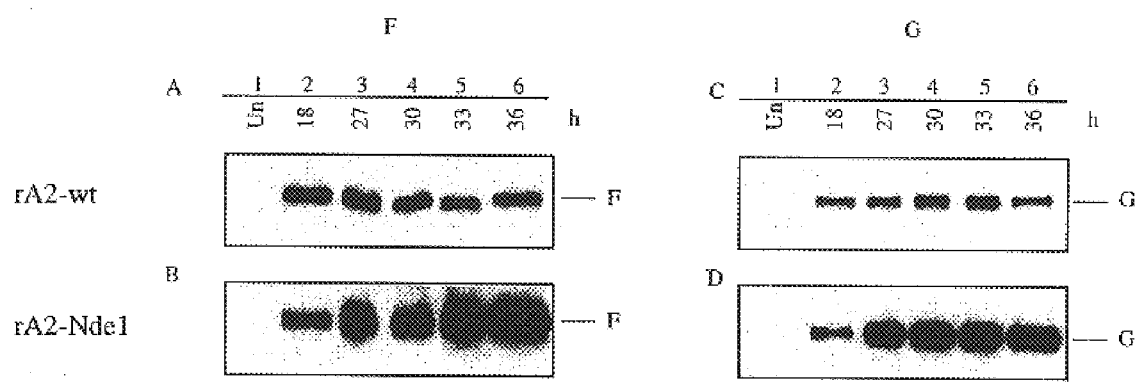
FIG. 6 provides a Western blot analysis of the accumulation of F and G glycoproteins in HEp-2 cells infected at an moi of 5 with rA2-wt (A, C) or rA2-K5 (B, D). Cells were harvested at the indicated time and total cellular protein was subjected to polyacrylamide gel electrophoresis under denaturing and reducing conditions, transferred to nitrocellulose (Teng et al., *J. Virol.* 73:466–473, 1999), and reacted with rabbit anti-peptide. serum against the cytoplasmic domain of the F (A, B) or G (C, D) protein. Bound antibodies were detected with horseradish peroxidase-conjugated goat anti-rabbit IgG and visualized by enhanced chemiluminescence (Amersham).

The increase in the accumulation of mRNA in cells infected with the rA2-NdeI and rA2-K5 viruses was mirrored by an increase in the accumulation of viral protein. FIG. 6 shows a Western blot analysis of the F (panels A and B) and G (Panels C and D) proteins synthesized in cells infected with rA2-wt virus or rA2-K5 virus. The amount of F or G protein present in the harvested cells at 36 h post-infection (panels A, B, C, and D, lane 6) was 3-fold greater for rA2-NdeI than for rA2-wt.

Summarizing the above results, M2 ORF2 can be interrupted in rRSV of the invention without loss of viability in cell culture. However, there were significant alterations in the viral RNA synthetic program, cell culture pathogenicity, and growth characteristics. These findings demonstrate that M2 ORF2 is an eleventh RSV gene, which is somewhat unexpected since the ORF is located in the downstream half of the M2 mRNA, is preceded by 11 methionyl codons, and thus would not be expected to be efficiently translated. Since ORF2 is expressed as a separate protein (Collins et al., *J. Gen. Virol.* 71:3015–20, 1990), one possibility is that it is accessed by a ribosomal stop-restart mechanism, such as described for the second ORF of the M gene of influenza virus B (Horvath et al., *Embo J.* 9:2639–47, 1990). The activity described for M2-2 identifies an RNA regulatory protein in a negative strand RNA virus.

The absence of M2-2 in recombinant RSV of the invention is associated with a reduction in the accumulation of genomic and antigenomic RNA, the products of RNA replication, and an increase in the accumulation of mRNA, the product of transcription. This indicates two activities for M2-2. The first is to increase RNA replication. The second activity is to regulate transcription. In cells infected with rA2-wt, the accumulation of mRNA increased rapidly up to approximately 12 h and more slowly thereafter, suggesting that transcription is down-regulated after that time. One of the effects of ablating M2-2 expression is to delay the appearance of mRNA. Although this may mean that M2-2 mediates positive regulation early in infection, the simpler explanation is that the delayed, reduced synthesis of mRNA is a consequence of delayed, reduced synthesis of its genomic RNA template. Although the accumulation of mRNA by the mutant viruses was delayed, it reached wt levels by approximately 12–15 h and continued to increase thereafter. This suggests that M2-2 mediates negative regulation of transcription late in infection, which is alleviated in its absence. Since the proteins of nonsegmented negative strand RNA viruses typically increase in abundance during the course of infection, this negative regulatory effect likely is concentration-dependent. Thus, RSV transcription is subject to negative autoregulation, and RNA regulation is subject to positive regulation.

It is generally thought that there is a dynamic, reversible "switch" between transcription and RNA replication by nonsegmented negative strand RNA viruses. For example, the synthesis of mRNA and antigenome ostensively involves the same promoter and genomic nucleocapsid template and, for most viruses, the same protein components, N, P and L. RSV is an exception in having the additional transcription-specific factor M2-1. One widely accepted model is that RNA synthesis switches from transcription to RNA replication when sufficient N protein accumulates to mediate cosynthetic encapsidation of the nascent RNA. This somehow switches the polymerase to read through gene junctions and synthesize a complete antigenome (Lamb et al., In Fields Virology (B. N. Fields et al., Eds., Vol. 1, pp. 1177–1204. Lippincott-Raven, Philadelphia, 1996). However, in earlier work we were unable to reconstitute this switch in a model minireplicon system by overexpression of N protein (Feams et al., Virology 236, 188–201, 1997). Unexpectedly, the present study implicates the M2-2 protein in this switch. It remains to be determined whether the observed effects on transcription and replication are linked rather than independent events. In terms of a single-step growth cycle, the present results suggest that the M2-2 protein functions around 12–15 h post infection to reduce transcription (after which the already-made mRNAs continue to drive protein synthesis) and turn on RNA replication, shifting the RNA synthetic program into virion production.

It is possible that M2-2 also has other functions. However, the other phenotypic differences observed to date for the M2-2 knock-out viruses probably can be explained by the changes in the RNA synthetic program described above. For example, the delay and reduction of virus production might simply be a consequence of the delay and reduction in synthesis of progeny genome, and the initial delay in the accumulation of mRNA. The other phenotypic difference, accelerated plaque formation, could be a consequence of increased synthesis of surface glycoproteins and accelerated cell-to-cell fusion. Nonetheless, this does not preclude other activities for M2-2.

Previous studies showed that the M2-2 protein inhibited RNA replication and transcription by RSV model minireplicons (Collins et al., Proc. Nat. Acad. Sci. USA 93:81–5, 1996; Hardy et al., J. Virol. 72:520–6, 1998). M2-2-mediated inhibition of minigenome transcription is consistent with the findings disclosed herein. However, the previously-observed M2-2-mediated inhibition of minireplicon RNA replication contrasts with the present findings, where the absence rather than the presence of M2-2 is associated with reduced RNA replication by rRSV. Thus, certain results from the minireplicon system may be incomplete. This distinction may be attributable to differences between the minireplicon system and an authentic virus infection, for example: (i) the supply of proteins would be greatly affected by regulation in an authentic infection but not in a reconstituted minireplicon system where proteins are supplied by transfected plasmids, (ii) the effects of M2-2 observed to date have been in minireplicon systems in which only a subset of viral proteins was supplied, and (iii) the relative level of M2-2 expressed in an authentic infection has not been determined but seems to be very low, and the minireplicon studies to date might have used levels that were too high.

The finding that M2-2 is not essential for growth defines this species as an accessory protein. Other paramyxovirus accessory proteins include the RSV SH, NS1 and NS2 proteins, the V and C proteins of Sendai virus, measles virus and parainfluenza virus type 3 (PIV3) and the D protein of PIV3 (Bukreyev et al., J. Virol. 71: 8973–82, 1997; Delenda et al., Virology 228: 55–62, 1997; He et al., Virology 250:30–40, 1998; Kato et al., EMBO J. 16:578–587, 1997; Kurotani et al., Genes to Cells 3:111–24, 1998; Latorre et al., J. Virol. 72:5984–93, 1998; Radecke et al., Virology 217:418–21, 1996; Schneider et al., Virology 227:314–22, 1997; Teng et al., J. Virol. 72:5707–16, 1998; Whitehead et al., J. Virol. 73:3438–42, 1999; and U.S. patent application Ser. No. 09/350,821; each incorporated herein by reference). Among these, the Sendai virus C protein has been studied the most extensively. Ablation of the expression of the V protein in recombinant Sendai virus was associated with increases in transcription, RNA replication and virus growth in vitro (Kato et al., Embo J. 16:578–587, 1997), although these differences were not apparent in a separate study (Delenda et al., Virology 228:55–62, 1997). Growth of V-minus Sendai virus in vivo was attenuated, suggesting that the V protein augments pathogenicity (Delenda et al., Virology 228:55–62, 1997).

The Sendai virus C protein is expressed as four proteins, namely C', C, Y1 and Y2, which arise from translational initiation at the first through fourth translational start sites in the C ORF, respectively. Deletion of these proteins individually and in groups has complex effects which are not completely defined and which are complicated because deletion of one species can alter expression of the another. Deletion of the C' and C proteins individually resulted in increased synthesis of mRNA and genomic RNA, whereas production of infectious virus was slightly reduced (Latorre et al., J. Virol. 72:5984–93, 1998). Inexplicably, the C'-minus virus retained virulence in vivo whereas the C-minus virus was attenuated. This result is particularly surprising since C' and C differ only buy the presence of 11 additional N-terminal amino acids in C'. Deletion of both C' and C delayed the appearance of genome and mRNA, after which these species were overproduced, and greatly reduced the production of infectious virus (Kurotani et al., Genes Cells 3:111–24, 1998; Latorre et al., J. Virol. 72:5984–93, 1998). Elimination of all four C-related proteins in Sendai virus resulted in a virus that was extremely debilitated for RNA synthesis and growth in vitro (Kurotani et al., Genes Cells 3:111–24, 1998). The complexity of these effects indicates that the functions of the V and various C proteins cannot be explained solely with respect to regulation of RNA synthesis and remain to be defined.

M2 ORF2 knock out mutants of the invention are particularly useful as candidates for development of RSV vaccines. Ablation of expression of the M2-2 gene in the above examples yielded attenuated virus growth in cell culture by at least 1000-fold during the initial days of a multi-cycle growth curve in vitro, with the final yield of infectious virus being reduced approximately 10-fold. This level of attenuation is highly desirable for construction of recombinant vaccine viruses of the invention. The similarity in final yield between the wt and M2-2 knock-out viruses in cell culture indicates that this modification in recombinant RSV is amenable to production of vaccine virus. Surprisingly, although virus growth is attenuated in M2-2 knock out mutants, gene expression is enhanced. Typically, RSV gene expression is roughly proportional to virus growth, and attenuating mutations which reduce growth reduce antigen production. Thus, one of the long-standing problems in RSV vaccine development has been to provide a level of attenuation which minimizes disease, yet retains sufficient immunogenicity. The M2-2 knock out mutation provides an important tool to resolve this problem by conferring significant attenuation in a recombinant RSV that also exhibits a concomitant increase, rather than decrease, in antigen expression. Although these examples describe the effects of ablating expression of M2-2, it is clear that intermediate effects can be achieved by reducing rather than ablating expression. Also, expression of M2-2 can be increased to achieve other effects on virus growth and gene expression. Alteration of the level of gene expression can be achieved by altering the M2-2 translational start site, or by placing the ORF under control of gene start and gene end signals and expressing it as a separate mRNA. The level of mRNA expression could be varied by the placement of the gene in a different gene order than the natural gene order position; or by mutations in cis-acting transcription elements, such as the mutation in position 9 of the gene start signal which was identified in cpts248/404 RSV (Whitehead et al., *Virology* 247:232–239, 1998, incorporated herein by reference).

EXAMPLE IV

Attenuation and Immunogenicity of NS1 or M2-2 Mutant RSV in Chimpanzees

In the present example, recombinant RSV which cannot express the NS1 or M2-2 protein, designated rA2ΔNS1 and rA2ΔM2-2, respectively, were evaluated as live-attenuated RSV vaccines. The rA2≢NS1 virus, described above, contains a large deletion that confers genetic stability during replication in vitro and in vivo and specifies attenuated replication in vitro that is approximately 10-fold reduced compared to that of wild-type recombinant RSV (rA2). The M2-2 mutant RSV, designated rA2ΔM2-2, exhibited delayed in vitro growth kinetics but reached final titers similar to those of rA2. In the present example, each virus was administered to the respiratory tract of RSV-seronegative chimpanzees to assess replication, immunogenicity, and protective efficacy in this model host.

As described in further detail below, the rA2ΔNS1 and rA2ΔM2-2 viruses were 2,200- to 55,000-fold restricted in replication in the upper and lower respiratory tracts of chimpanzees and induced a level of RSV-neutralizing serum antibody that was only slightly reduced compared to that of wild-type RSV. The replication of wild-type RSV after challenge was reduced more than 10,000-fold at each site. Importantly, rA2ΔNS1 and rA2ΔM2-2 were 10-fold more restricted in replication in the upper respiratory tract than was the cpts248/404 virus, a vaccine candidate that retains mild reactogenicity in the upper respiratory tract of the 1 month-old infant. Thus, either virus might be appropriately attenuated for this age group, which is a target population for a RSV vaccine. In addition, these results confirm that neither NS1 nor M2-2 is essential for RSV replication in vivo, although each is important for efficient replication.

The rA2ΔM2-2 and rA2ΔNS1 viruses were evaluated for replication, immunogenicity, and protective efficacy in the upper and lower respiratory tracts of chimpanzees. The rA2ΔM2-2 and rA2ΔNS1 viruses were constructed using the antigenomic cDNA described above (see also, Collins, et al. (Collins et al., *Proc. Natl. Acad. Sci. USA* 92:11563–11567, 1995; incorporated herein by reference), and the recombinant viruses also contained two types of modifications described above: (i) the introduction of a set of six translationally silent restriction site markers in the L gene, called the "sites" mutations, and (ii) two amino acid substitutions in the F protein, called the "HEK" mutations, which make the recombinant virus identical at the amino acid level to the wild-type RSV A2 parent from which the cpts248/404 series of biological vaccine candidates was derived (see also, Juhasz et al., *J. Virol.* 71:5814–5819, 1997; Whitehead et al., *Virology* 247:232–39, 1998, each incorporated herein by reference). These mutations were shown to be phenotypically silent in the chimpanzee (Whitehead et al., *J. Virol.* 72:4467–4471, 1998; incorporated herein by reference). The rA2ΔNS1 virus used in this study was reconstructed in a sites/HEK background, in preparation for clinical evaluation, whereas the rA2ΔM2-2 virus is in the original genetic background, a difference that is irrelevant for the present study (Bermingham et al., *Proc. Natl. Acad. Sci. USA* 96:11259–11264, 1999; Whitehead et al., *Virology* 247:232–39, 1998, each incorporated herein by reference).

The rA2ΔNS1 and rA2ΔM2-2 viruses were administered individually to juvenile RSV-seronegative chimpanzees by combined intranasal and intratracheal inoculation, as described previously (Crowe et al., *Vaccine* 12:783–790, 1994; incorporated herein by reference). Since both viruses were attenuated in vitro, animals were inoculated with a relatively high dose of $10^5$ PFU per ml per site. To monitor virus replication in the upper and lower respiratory tracts, respectively, nasopharyngeal swabs and tracheal lavage samples were collected at intervals over ten days post-infection and subsequently assayed for virus titer. The mean peak virus titer was determined for each group (Table I). The chimpanzees were monitored daily for rhinorrhea, a symptom of upper respiratory tract illness, and the mean peak score was determined for each group (Table I). Due to the limited availability of RSV-seronegative chimpanzees, the number of animals per group was small, necessitating comparisons with previous studies in which we had evaluated biologically-derived RSV strain A2 (wt RSV A2), recombinant wild-type strain A2 (rA2), rA2ΔSH, rA2ΔNS2, and a recombinant version of the above-mentioned cpts248/404 vaccine candidate (rA2cp248/404) (Table I).

Replication of both rA2ΔNS1 and rA2ΔM2-2 was reduced more than 2200-fold and 2800-fold, respectively, in the upper respiratory tract compared to rA2 (Table I). Shedding of rA2ΔNS1 or rA2ΔM2-2 was detected sporadically and at a low level beginning 2 to 7 days post-inoculation and each animal shed virus over a period of 3 to 8 days. Thus, the recovered virus was not carried over from the initial inoculum, but represented replication near the level of detection over a period of several days. In the lower respiratory tract, rA2ΔNS1 was reduced more than 17,000-fold in replication compared to rA2, while rA2ΔM2-2 was undetectable at all time points (greater than 55,000-fold reduction). It is important to note that the dose of rA2ΔNS1 and rA2ΔM2-2 used was 10-fold greater than that of rA2. Furthermore, both viruses were more attenuated than rA2cp248/404 which was given at the same dose, particularly in the case of rA2ΔM2-2 which was not recovered from the lungs of infected chimps. In addition, both rA2ΔNS1 and rA2ΔM2-2 were unusual in being highly restricted in the upper as well as the lower respiratory tract. In the upper respiratory tract, each virus was approximately 10-fold more restricted than cpts248/404, and 175-fold more restricted than rA2ΔNS2. Since upper respiratory tract congestion was observed during clinical evaluation of the cpts248/404 virus in 1–2 month old infants (Wright, P. F., R. A. Karron, R. B.

Belshe, J. Thompson, J. E. Crowe Jr., T. G. Boyce, L. L. Halburnt, G. W. Reed, S. S. Whitehead, E. L. Anderson, A. E. Wittek, R. Casey, M. Eichelberger, B. Thumar, V. B. Randolph, S. A. Udem, R. M. Chanock, and B. R. Murphy "Evaluation of a live, cold-passaged, temperature-sensitive, respiratory syncytial virus (RSV) vaccine candidate in infancy," submitted; incorporated herein by reference) and since infants of that age are obligate nose-breathers, mutations that confer a level of restriction of replication in the upper respiratory tract greater than that of cpts248/404 will be desirable for inclusion in a live-attenuated vaccine virus. Animals receiving rA2ΔNS1 or rA2ΔM2-2 had slightly more rhinorrhea than those infected with rA2cp248/404, though still less than animals infected with a ten-fold smaller dose of rA2. Although it is possible that the absence of NS1 or M2-2 resulted in a virus that retained a moderate level of virulence but replicated poorly, this appears unlikely. It is expected that further evaluation, including clinical studies, will show that the amount of residual virulence associated with rA2ΔNS1 and rA2ΔM2-2 is attributed to their greatly reduced replication.

Despite the highly-restricted replication of the rA2ΔNS1 and rA2ΔM2-2 viruses, immunization with either recombinant induced a level of RSV-neutralizing serum antibody that was within 2-fold of that induced by rA2cp248/404 (Table I). Furthermore, animals previously infected with either rA2ΔNS1 or rA2ΔM2-2 were highly resistant to the replication of wt RSV administered intranasally and intratracheally 56 days post-immunization (Table II). The level of protection in both cases was similar in the upper respiratory tract and somewhat less in the lower respiratory tract to that seen with cpts248/404, both in mean peak titer and in mean days of shedding.

TABLE I rA2ΔNS1 and rA2ΔM2-2 are highly attenuated and immunogenic in both the upper and lower respiratory tracts of chimpanzees

| Virus used to infect chimpanzees[a] | No. of animals | Dose[b] (per site, $\log_{10}$ pfu) | Mean peak virus titer[c] ($\log_{10}$ pfu/ml ± SE) (Duncan grouping) | | Rhinorrhea score[d] (range = 0–4) Mean peak | Mean serum neutralizing antibody titer[e] (reciprocal $\log_2$) | |
|---|---|---|---|---|---|---|---|
| | | | Nasopharyngeal swab | Tracheal lavage | | Day 0 | Day 28 |
| wt RSV A2[f] | 2 | 4.0 | 5.0 ± 0.35 (A) | 5.5 ± 0.40 (A) | 3.0 | <3.3 | 11.2 |
| rA2[g] | 2 | 4.0 | 4.9 ± 0.15 (A) | 5.4 ± 0.05 (A) | 2.5 | <3.3 | 10.5 |
| rA2ΔSH[g] | 3 | 4.0 | 4.6 ± 0.10 (A) | 3.8 ± 0.31 (B) | 1.0 | <3.3 | 10.2 |
| rA2ΔNS2[g] | 4 | 4.0 | 3.8 ± 0.41 (B) | 1.4 ± 0.29 (C) | 1.0 | 3.4 | 10.6 |
| rA2cp248/404[g] | 4 | 5.0 | 2.5 ± 0.25 (C) | 1.4 ± 0.37 (C) | 0.8 | 3.4 | 10.6 |
| rA2ΔNS1 | 4 | 5.0 | 1.6 ± 0.12 (D) | 1.2 ± 0.43 (C) | 2.0 | <3.3 | 9.8 |
| rA2ΔM2-2 | 4 | 5.0 | 1.5 ± 0.09 (D) | <0.7 | 1.8 | <3.3 | 9.1 |

[a]All recombinant-derived viruses (r) contain the sites and HEK mutations (see text), except for rA2ΔM2-2.
[b]Chimpanzees were inoculated by the intranasal and intratracheal routes with the indicated amount of virus in a 1 ml inoculum per site.
[c]Nasopharyngeal swab samples were collected daily for ten days and tracheal lavage samples were collected on days 2, 5, 6, 8 and 10. Mean peak titers were calculated and assigned to statistically similar groups by Duncan's Multiple Range test ($\alpha = 0.05$). Means in each column with different letters are significantly different.
[d]The amount of rhinorrhea was estimated daily and assigned a score (0 to 4) that indicated extent and severity. Scores indicate severe [4], moderate [3], mild [2], trace [1], or no [0] rhinorrhea. Shown are the man peak scores.
[e]Serum RSV-neutralizing antibody titers were determined by a complement-enhanced 60% plaque-reduction assay using wt RSV A2 and HEp-2 cell monolayer cultures incubated at 37° C.. RSV-seronegative chimpanzee serum used as a negative control had a neutralizing antibody titer .3 $\log_2$. Adult human serum used as a positive control had a neutralizing antibody titer of 11.4 $\log_2$.
[f]Historic controls from the study of Crowe, et al., (Vaccine 13:847–855, 1995; incorporated herein by reference).
[g]Data from the study of Whitehead, et al. (J. Virol. 73:3438–3442, 1999; incorporated herein by reference).

TABLE II rA2ΔNS1 and rA2ΔM2-2 are highly protective against challenge with wt RSV A2 in the upper and lower respiratory tracts or chimpanzees.

| | | | Replication of RSV challenge virus at the indicated site[b] | | | | |
|---|---|---|---|---|---|---|---|
| | | | Nasopharynx | | Trachea | | |
| Immunizing virus | Inoculum dose[a] ($\log_{10}$ PFU/ml) | No. of animals | Mean days of shedding | Mean peak titer[c] | Mean days of shedding | Mean peak titer[c] | Mean peak rhinorrhea score |
| rA2ΔNS1 | 5.0 | 4 | 2.8 ± 0.75 | 1.7 ± 0.46 | 1.0 ± 0.41 | 1.8 ± 0.73 | 1.0 |
| rA2ΔM2-2 | 5.0 | 4 | 3.5 ± 0.87 | 2.3 ± 0.71 | 1.0 ± 0.71 | 1.7 ± 0.63 | 1.0 |
| rA2ΔNS2[d] | 4.0 | 4 | ND[f] | 1.9 ± 0.30 | ND[f] | 2.2 ± 0.77 | 1.0 |
| cpts248/404[e] | 4.7 | 2 | 3.5 ± 0.50 | 2.3 ± 0.25 | 0 | <0.7 | 1.0 |
| none[e] | | 2 | 8.5 ± 0.50 | 5.0 ± 0.35 | 6.0 ± 1.0 | 4.8 ± 0.30 | 3.0 |

[a]Each virus was initially administered at the indicated dose in a 1.0 ml inoculum given intranasally and intratracheally.
[b]On day 56, chimpanzees were challenged with wt RSV A2 administered at a dose of $10^4$ PFU/ml in a 1.0 ml inoculum given intranasally and intratracheally. Nasopharyngeal swab samples were collected daily for twelve days and tracheal lavage samples were collected on days 2, 5, 6, 8, and 12.
[c]Mean peak titers ($\log_{10}$ PFU/ml) were calculated using the peak virus titer achieved in each animal.
[d]Data from the study of Whitehead, et al. (J. Virol. 73:3438–3442, 1999; incorporated herein by reference).
[e]Historic controls from the study of Crowe, et al., (Vaccine 13:847–855, 1995; incorporated herein by reference).
[f]ND, not determined As noted above, deletion of NS2 and other modifications to RSV genes yields desired phenotypic effects, including attenuation via non-ts mutations (Whitehead et al., *J. Virol.* 73:3438–3442, 1999; incorporated herein by reference). Compared to rA2ΔNS2, rA2ΔNS1 and rA2ΔM2-2 are substantially more attenuated, even at a ten-fold higher dose (Table I), while providing similar levels of protection against challenge with wt RSV (Table II). Deletion mutants are extremely stable both in vitro and in vivo, thus making them attractive candidates for vaccine development. This property will be important in certain aspects of the invention. A low level of genetic instability in a RSV vaccine likely would not be a problem in normal individuals, particularly considering the high prevalence of fully-virulent wild-type RSV. However, vaccine virus might have prolonged replication in immunocompromised individuals. Thus, it will often be desirable to engineer recombinant vaccine viruses that contain attenuating mutations resistant to reversion.

A principal target for a RSV vaccine is the 1 to 2 month old infant, while a second major target is the elderly. A live-attenuated vaccine for RSV-naive infants will need to be more attenuated than one for use in adults (see, e.g., Gonzalez et al., *Vaccine* 18:1763–1772, 2000; incorporated herein by reference). In this context, the rA2ΔNS1 and rA2ΔM2-2 viruses are similar to cpts248/404 in their level of replication, and therefore will most likely be useful in development of a pediatric RSV vaccine, either as currently constructed or with the inclusion of one or more additional attenuating mutations described herein. As with other RSV recombinants described herein, the rA2ΔNS1 and rA2ΔM2-2 viruses can be rapidly adapted as a RSV subgroup A or subgroup B vaccine virus by replacing the F and G glycoproteins. (Whitehead et al., *J. Virol.* 73:9773–80, 1999; incorporated herein by reference).

Microorganism Deposit Information

The following materials have been deposited with the American Type Culture Collection, 10801 University Boulevard, Manassas, Va. 20110-2209, under the conditions of the Budapest Treaty and designated as follows:

| Plasmid | Accession No. | Deposit Date |
| --- | --- | --- |
| cpts RSV 248 | ATCC VR 2450 | Mar. 22, 1994 |
| cpts RSV 248/404 | ATCC VR 2454 | Mar. 22, 1994 |
| cpts RSV 248/955 | ATCC VR 2453 | Mar. 22, 1994 |
| cpts RSV 530 | ATCC VR 2452 | Mar. 22, 1994 |
| cpts RSV 530/1009 | ATCC VR 2451 | Mar. 22, 1994 |
| cpts RSV 530/1030 | ATCC VR 2455 | Mar. 22, 1994 |
| RSV B-1 cp52/2B5 | ATCC VR 2542 | Sept. 26, 1996 |
| RSV B-1 cp-23 | ATCC VR 2579 | July 15, 1997 |
| p3/7(131) | ATCC 97990 | Apr. 18, 1997 |
| p3/7(131)2G | ATCC 97989 | Apr. 18, 1997 |
| p218(131) | ATCC 97991 | Apr. 18, 1997 |

Although the foregoing invention has been described in detail by way of example for purposes of clarity of understanding, it will be apparent to the artisan that certain changes and modifications may be practice within the scope of the appended claims which are presented by way of illustration not limitation. In this context, various publications and other references have been cited within the foregoing disclosure for economy of description. Each of these references are incorporated herein by reference in its entirety for all purposes.

What is claimed is:

1. An isolated infectious recombinant respiratory syncytial virus (RSV) comprising a RSV genome or antigenome, a major nucleocapsid (N) protein, a nucleocapsid phosphoprotein (P), a large polymerase protein (L), and a M2(ORF1) RNA polymerase elongation factor, wherein a modification is introduced in the genome or antigenome comprising a partial or complete deletion of M2 ORF2 or one or more nucleotide change(s) that reduce or ablate expression of M2 ORF2.

2. The recombinant RSV of claim 1, wherein expression of M2 ORF2 is ablated by introduction of one or more stop codons.

3. The recombinant RSV of claim 2 which is rA2-K5.

4. The recombinant RSV of claim 1, wherein expression of M2 ORF2 is ablated by introduction of a frame shift mutation.

5. The recombinant RSV of claim 4 which is rA2-NdeI.

6. The recombinant RSV of claim 1, wherein M2 ORF2 is deleted in whole or in part.

7. The recombinant RSV of claim 1, wherein the modification in the genome or antigenome specifies one or more desired phenotypic changes in the recombinant RSV selected from (i) a change in mRNA synthesis, (ii) a change in the level of viral protein expression; (iii) a change in genomic or antigenomic RNA replication, (iv) a change in viral growth characteristics, (v), a change in viral plaque size, and/or vi) a change in cytopathogenicity.

8. The recombinant RSV of claim 7, wherein the phenotypic change comprises attenuation of viral growth compared to growth of a corresponding wild-type or mutant parental RSV strain.

9. The recombinant RSV of claim 1, wherein the RSV genome comprises one or more shifted RSV gene(s) or genome segment(s) that is/are positionally shited within genome or antigenome to a more promoter-proximal or promoter-distal position relative to a position of said RSV gene(s) or genome segment(s) within a wild type RSV genome or antigenome.

10. The recombinant RSV of claim 9, wherein said one or more shifted gene(s) or genome segment(s) is/are shifted to a more promoter-proximal or promoter-distal position by deletion or insertion of one or more displacement polynucleotide(s) within said partial or complete genome or antigenome.

11. The recombinant RSV of claim 7, wherein the phenotypic change comprises delayed kinetics of viral mRNA synthesis compared to kinetics of mRNA synthesis of a corresponding wild-type or mutant parental RSV strain.

12. The recombinant RSV of claim 7, wherein the phenotypic change comprises a change in cumulative MRNA synthesis compared to cumulative mRNA synthesis of a corresponding wild-type or mutant parental RSV strain.

13. The recombinant RSV of claim 12, wherein the increase in cumulative viral mRNA synthesis is approximately 1.3 to 2-fold or greater at 24 hours post-infection compared to cumulative mRNA synthesis of the corresponding wild-type or mutant parental RSV strain.

14. The recombinant RSV of claim 7, wherein the phenotypic change comprises increased viral protein accumulation in infected cells compared to viral protein accumulation in cells infected with a corresponding wild-type or mutant parental RSV strain.

15. The recombinant RSV of claim 7, wherein accumulation of one or more viral proteins is increased approximately 2- to 3-fold or greater compared to viral protein accumulation in cells infected with the corresponding wild-type or mutant parental RSV strain.

16. The recombinant RSV of claim 7, wherein the phenotypic change comprises increased expression of one or more viral antigens compared to expression of said one or more viral antigens by the corresponding wild-type or mutant parental RSV strain.

17. The recombinant RSV of claim 7, wherein the phenotypic change comprises a change in viral RNA replication compared to viral RNA replication of a corresponding wild-type or mutant parental RSV strain.

18. The recombinant RSV of claim 17, wherein accumulation of genomic and antigenomic RNA is decreased compared to accumulation of genomic and antigenomic RNA of the corresponding wild-type or mutant parental RSV strain.

19. The recombinant RSV of claim 7, wherein the phenotypic change comprises an increase in cumulative mRNA synthesis and a reduction in viral RNA replication compared to cumulative mRNA synthesis and viral RNA replication of a corresponding wild-type or mutant parental RSV strain.

20. The recombinant RSV of claim 19, wherein a cumulative molar ratio of mRNA to genomic RNA is increased approximately 7- to 18-fold or greater compared to a cumulative molar ratio of mRNA to genomic RNA observed for the corresponding wild-type or mutant parental RSV strain.

21. The recombinant RSV of claim 7, wherein the phenotypic change comprises a larger plaque phenotype compared to plaque phenotype of a corresponding wild-type or mutant parental RSV strain.

22. The recombinant RSV of claim 7, wherein the phenotypic change comprises a change in cytopathogenicity compared to cytopathogenicity of a corresponding wild-type or mutant parental RSV strain.

23. The recombinant RSV of claim 1, wherein the genome or antigenome is further modified by introduction of one or more attenuating mutations identified in a biologically derived mutant human RSV.

24. The recombinant RSV of claim 23, wherein the genome or antigenome incorporates at least one and up to a full complement of attenuating mutations present within a panel of biologically derived mutant human RSV strains, said panel comprising cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579).

25. The recombinant RSV of claim 23, wherein the genome or antigenome incorporates at least one and up to a fall complement of attenuating mutations specifying an amino acid substitution at Val267 in the RSV N gene, Glu218 and/or Thr523 in the RSV F gene, Asn43, Cys319 Phe521, Gln831, Met1169, Tyr1321 and/or His1690 in the RSV polymerase gene L, and a nucleotide substitution in the gene-start sequence of gene M2.

26. The recombinant RSV of claim 23, wherein the genome or antigenome incorporates at least two attenuating mutations.

27. The recombinant RSV of claim 23, wherein the genome or antigenome includes at least one attenuating mutation stabilized by multiple nucleotide changes in a codon specifying the mutation.

28. The recombinant RSV of claim 1, wherein the genome or antigenome comprises an additional nucleotide modification specifying a phenotypic change selected from a change in growth characteristics, attenuation, temperature-sensitivity, cold-adaptation, plaque size, host-range restriction, antigen expression, or a change in immunogenicity.

29. The recombinant RSV of claim 28, wherein the additional nucleotide modification alters a SH, NS1, NS2, or G gene of the recombinant RSV.

30. The recombinant RSV of claim 29, wherein a SH, NS1, NS2, or G gene is deleted in whole or in part or expression of the gene is reduced or ablated by a frame shift or introduction of one or more stop codons in an open reading frame of the gene or a modification of a tranlational start site.

31. The recombinant RSV of claim 28, wherein the nucleotide modification comprises a nucleotide deletion, insertion, substitution, addition or rearrangement of a cis-acting regulatory sequence of a selected gene within the recombinant RSV genome or antigenome.

32. The recombinant RSV of claim 31, wherein a gene end (GE) signal of the NS1 or NS2 gene is modified.

33. The recombinant RSV of claim 28, wherein the nucleotide modification comprises an insertion, deletion, substitution, or rearrangement of a translational start site within the recombinant RSV genome or antigenome.

34. The recombinant RSV of claim 33, wherein the translational start site for a secreted form of the RSV G glycoprotein is ablated.

35. The recombinant RSV of claim 28, wherein the genome or antigenome is modified to encode a non-RSV molecule selected from a cytokine, a T-helper epitope, a restriction site marker, or a protein of a microbial pathogen capable of eliciting a protective immune response in a mammalian host.

36. The recombinant RSV of claim 28, wherein the genome or antigenome incorporates a gene or genome segment from parainfluenza virus (PIV).

37. The recombinant RSV of claim 36, wherein the gene or genome segment encodes a PIV HN or F glycoprotein or immunogenic domain or epitope thereof.

38. The recombinant RSV of claim 37, wherein the genome segment encodes an ectodomain or immunogenic epitope of HN or F of PIV1, PIV2, or PIV3.

39. The recombinant RSV of claim 1, wherein the genome or antigenome comprises a partial or complete RSV background genome or antigenome of a human or bovine RSV combined with a heterologous gene or genome segment of a different RSV to form a human-bovine chimeric RSV genome or antigenome.

40. The recombinant RSV of claim 39, wherein the heterologous gene or genome segment encodes a RSV F, G or SH glycoprotein or an immunogenic domain or epitope thereof.

41. The recombinant RSV of claim 39, wherein the heterologous gene or genome segment is substituted for a counterpart gene or genome segment in a partial RSV background genome or antigenome.

42. The recombinant RSV of claim 39, wherein the heterologous gene or genome segment is added adjacent to or within a noncoding region of the partial or complete RSV background genome or antigenome.

43. The recombinant RSV of claim 39, wherein the chimeric genome or antigenome comprises a partial or complete human RSV background genome or antigenome combined with a heterologous gene or genome segment from a bovine RSV.

44. The recombinant RSV of claim 39, wherein the chimeric genome or antigenome comprises a partial or complete bovine RSV background genome or antigenome combined with a heterologous gene or genome segment from a human RSV.

45. The recombinant RSV of claim 44, wherein one or more human RSV glycoprotein genes F, G and SH or a genome segment encoding a cytoplasmic domain, transmembrane domain, ectodomain or immunogenic epitope thereof is substituted for a counterpart gene or genome segment within the bovine RSV background genome or antigenome.

46. The recombinant RSV of claim 45, wherein one or both human RSV glycoprotein genes F and G is substituted to replace one or both counterpart F and G glycoprotein genes in the bovine RSV background genome or antigenome.

47. The recombinant RSV of claim 46, wherein both human RSV glycoprotein genes F and G are substituted to replace counterpart F and G glycoprotein genes in the bovine RSV background genome or antigenome.

48. The recombinant RSV of claim 45, wherein the heterologous gene or genome segment is from a subgroup A or subgroup B human RSV.

49. The recombinant RSV of claim 45, wherein the human-bovine chimeric genome or antigenome incorporates antigenic determinants from both subgroup A and subgroup B human RSV.

50. The recombinant RSV of claim 1 which is a complete virus.

51. The recombinant RSV of claim 1 which is a subviral particle.

52. A method for stimulating the immune system of an individual to elicit an immune response against RSV which comprises administering to the individual an immunologically sufficient amount of the recombinant RSV of claim 1 combined with a physiologically acceptable carrier.

53. The method of claim 52, wherein the recombinant RSV is administered in a dose of $10^6$ to $10^7$ PFU.

54. The method of claim 52, wherein the recombinant RSV is administered to the upper respiratory tract.

55. The method of claim 52, wherein the recombinant RSV is administered by spray, droplet or aerosol.

56. The method of claim 52, wherein the recombinant RSV is administered to an individual seronegative for antibodies to RSV or possessing transplacentally acquired maternal antibodies to RSV.

57. The method of claim 52, wherein the recombinant RSV is attenuated and exhibits increased antigen expression compared to growth and antigen expression of a corresponding wild-type or mutant parental RSV strain.

58. The method of claim 52, wherein the recombinant RSV elicits an immune response against human RSV A, human RSV B, or both.

59. An immunogenic composition to elicit an immune response against RSV comprising an immunologically sufficient amount of the recombinant RSV of claim 1 in a physiologically acceptable carrier.

60. The immunogenic composition of claim 59 formulated in a dose of $10^3$ to $10^7$ PFU.

61. The immunogenic composition of claim 59, formulated for administration to the upper respiratory tract by spray, droplet or aerosol.

62. The immunogenic composition of claim 59, wherein the recombinant RSV exhibits attenuated growth and increased antigen expression compared to growth and antigen expression of a corresponding wild-type or mutant parental RSV strain.

63. The immunogenic composition of claim 62 which elicits an immune response against human RSV A, human RSV B, or both.

* * * * *

UNITED STATES PATENT AND TRADEMARK OFFICE
CERTIFICATE OF CORRECTION

PATENT NO. : 6,713,066 B1
DATED : March 30, 2004
INVENTOR(S) : Peter L. Collins, Brian R. Murphy and Alison Bermingham It is certified that error appears in the above-identified patent and that said Letters Patent is hereby corrected as shown below:

Column 75,
Line 35, please replace "shited" with -- shifted --.
Line 60, please replace "MRNA" with -- mRNA --.

Column 78,
Line 52, please replaec "$10^6$" with -- $10^3$ --.

Signed and Sealed this

Twenty-ninth Day of June, 2004

JON W. DUDAS
*Acting Director of the United States Patent and Trademark Office*

SEQUENCE LISTING

<160> NUMBER OF SEQ ID NOS: 8

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Forward
      primer for M2 ORF2

<400> SEQUENCE: 1
taattaatta agtataactt ccatactaat aacaag                         36

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Reverse
      primer for M2 ORF2

<400> SEQUENCE: 2
tcaggtagta tcgttatttt tggcgtggtc gtttgt                         36

<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence: Sequence
      spanning M2 ORF1 and M2 ORF 2

```
<400> SEQUENCE: 3
acaaatgacc atgccaaaaa taatgatact acctgacaaa tatccttgta gt           52

<210> SEQ ID NO 4
<211> LENGTH: 61
<212> TYPE: DNA
<213> ORGANISM: Artificial Sequence
<220> FEATURE:
<223> OTHER INFORMATION: Description of Artificial Sequence: Target
      site for M2 ORF2 mutation

<400> SEQUENCE: 4
aaccatatgt actcaccgaa tcaaacattc aatgaaatcc attggacctc tcaagaattg   60
a                                                                   61

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence: Sequence
      incorporating M2 ORF2 mutation

<400> SEQUENCE: 5
aaccatatat gtactcaccg aatcaaacat tcaatgaaat ccattggacc tctcaagaat   60
tga                                                                 63

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Amino acid
      sequence corresponding to  nucleotide sequence
      spanning M2 ORF1 and M2 ORF2

<400> SEQUENCE: 6

Thr Asn Asp His Ala Lys Asn Asn Asp Thr Thr
 1               5                  10

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Amino acid
      sequence corresponding to target site for M2 ORF2
      mutation

<400> SEQUENCE: 7

Asn His Met Tyr Ser Pro Asn Gln Thr Phe Asn Glu Ile His Trp Thr
 1               5                  10                  15

Ser Gln Glu Leu
            20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Amino acid
      sequence incorporating M2 ORF2 mutation
```

-continued

```
<400> SEQUENCE: 8

Asn His Ile Cys Thr His Arg Ile Lys His Ser Met Lys Ser Ile Gly
1               5                   10                  15

Pro Leu Lys Asn
            20
```